US011685767B2

(12) United States Patent
McFadden et al.

(10) Patent No.: US 11,685,767 B2
(45) Date of Patent: Jun. 27, 2023

(54) USE OF AAV-EXPRESSED M013 PROTEIN AS AN ANTI-INFLAMMATORY THERAPEUTIC

(71) Applicant: University of Florida Research Foundation, Incorporated, Gainesville, FL (US)

(72) Inventors: Douglas Grant McFadden, Tempe, AZ (US); Alfred S. Lewin, Gainesville, FL (US); Alexandra Rose Lucas, Tempe, AZ (US); Cristhian J. Ildefonso, Gainesville, FL (US); Mohammed Masmudur Rahman, Chandler, AZ (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 15/261,599

(22) Filed: Sep. 9, 2016

(65) Prior Publication Data
US 2016/0376325 A1 Dec. 29, 2016

Related U.S. Application Data

(63) Continuation of application No. PCT/US2015/020001, filed on Mar. 11, 2015.

(60) Provisional application No. 61/951,294, filed on Mar. 11, 2014.

(51) Int. Cl.
| | |
|---|---|
| A61K 48/00 | (2006.01) |
| C07H 21/04 | (2006.01) |
| C12N 15/86 | (2006.01) |
| C07K 14/005 | (2006.01) |
| A61K 9/00 | (2006.01) |
| A61K 38/16 | (2006.01) |
| C12N 7/00 | (2006.01) |
| A01K 67/00 | (2006.01) |

(52) U.S. Cl.
CPC .......... *C07K 14/005* (2013.01); *A61K 9/0048* (2013.01); *A61K 38/162* (2013.01); *A61K 48/005* (2013.01); *C12N 7/00* (2013.01); *C12N 15/86* (2013.01); *A61K 48/00* (2013.01); *C12N 2710/24022* (2013.01); *C12N 2750/14143* (2013.01)

(58) Field of Classification Search
CPC .... C07K 14/005; A61K 48/00; A61K 48/005; A61K 9/0048; C12N 7/00; C12N 15/86; C12N 2750/14143; C12N 2710/24022
See application file for complete search history.

(56) References Cited

U.S. PATENT DOCUMENTS

| | | | |
|---|---|---|---|
| 5,643,758 A | 7/1997 | Guan et al. | |
| 6,355,618 B1 | 3/2002 | Cai et al. | |
| 6,451,594 B1 | 9/2002 | Chien et al. | |
| 6,482,933 B1 | 11/2002 | Bertin | |
| 6,756,196 B2 | 6/2004 | Bertin | |
| 6,869,775 B2 | 3/2005 | Bertin | |
| 6,953,657 B2 | 10/2005 | Bertin | |
| 7,071,172 B2 | 7/2006 | McCown et al. | |
| 7,306,944 B2* | 12/2007 | Choi et al. | |
| 8,962,567 B2* | 2/2015 | Choi | A61K 38/52 514/20.8 |
| 10,981,961 B2 | 4/2021 | Ildefonso et al. | |
| 11,053,291 B2 | 7/2021 | Ildefonso et al. | |

(Continued)

FOREIGN PATENT DOCUMENTS

| | | |
|---|---|---|
| EP | 2000536 A2 | 12/2008 |
| WO | WO 2001/00826 A1 | 1/2001 |

(Continued)

OTHER PUBLICATIONS

Stockli et al. Molecular cloning, expression and regional distribution of rat ciliary neurotrophic factor. Nature, vol. 342:920-923, (Year: 1989).*
Chen et al. Distribution, markers, and functions of retinal microglia. Ocular Immunology and Inflammation 10:27-39, (Year: 2002).*
Solinis et al. Treatment of ocular disorders by gene therapy. European Journal of Pharmaceutics and Biopharmaceutics 95:331-342, (Year: 2015).*
Negro et al. Cloning and expression of human ciliary neurotrophic factor. Eur. J. Biochem. 201:289-294, (Year: 1991).*
Swiss-Protein Accession No. P26992 (Signal Peptide Database), 4 pages, (Year: 2008).*

(Continued)

*Primary Examiner* — Quang Nguyen
(74) *Attorney, Agent, or Firm* — Wolf, Greenfield & Sacks, P.C.

(57) ABSTRACT

Disclosed are methods and compositions for preventing, treating, and/or ameliorating one or more symptoms of inflammation in a mammal. In particular, viral vectors and medicaments containing them are disclosed, which are useful in the prophylaxis, therapy, or amelioration of symptoms of one or more inflammatory-mediated mammalian diseases, such as age-related macular degeneration (AMD), arthritis, Bechet's disease, Best macular dystrophy, corneal inflammation, diabetic retinopathy, drusen formation, dry AMD, dry eye, geographic atrophy, glaucomaocular neovascularization, Lupus erythematosus, macular degeneration, Mallatia Leventinese and Doyne honeycomb retinal dystrophy, nephritis, ocular hypertension, ocular inflammation, recurrent uveitis, Sorsby fundus dystrophy, vasculitis, vitreoretinopathy, wet AMD, or related disorders. In exemplary methods, administration of a pharmaceutical composition comprising a recombinant viral vector that delivers a secretable and cell-penetrating M013 protein or peptide to a subject in need thereof facilitated treatment of particular human disorders such as AMD, ocular neovascularization, uveitis, and related inflammatory ocular disease.

27 Claims, 16 Drawing Sheets
(10 of 16 Drawing Sheet(s) Filed in Color)
Specification includes a Sequence Listing.

(56) References Cited

U.S. PATENT DOCUMENTS

| | | | |
|---|---|---|---|
| 2003/0045498 | A1* | 3/2003 | Kovesdi et al. |
| 2003/0165488 | A1 | 9/2003 | Kletzien et al. |
| 2003/0171267 | A1 | 9/2003 | Rosen et al. |
| 2003/0236396 | A1 | 12/2003 | Fasel et al. |
| 2004/0063635 | A1 | 4/2004 | Yu et al. |
| 2005/0129685 | A1 | 6/2005 | Cao et al. |
| 2005/0142130 | A1 | 6/2005 | Roks et al. |
| 2007/0031410 | A1 | 2/2007 | Harton et al. |
| 2009/0148894 | A1 | 6/2009 | Broedel et al. |
| 2009/0239259 | A1* | 9/2009 | Hsieh .................. C07K 16/241 435/69.1 |
| 2010/0029012 | A1 | 2/2010 | Kern et al. |
| 2010/0120665 | A1* | 5/2010 | Kaleko et al. |
| 2010/0209447 | A1* | 8/2010 | Kumar-Singh et al. |
| 2011/0130345 | A1 | 6/2011 | Gourdie et al. |
| 2013/0157513 | A1 | 6/2013 | Hagen et al. |
| 2013/0310443 | A1* | 11/2013 | Srivastava et al. |
| 2017/0088593 | A1* | 3/2017 | Ildefonso et al. |
| 2021/0300978 | A1 | 9/2021 | Ildefonso et al. |
| 2021/0371481 | A1 | 12/2021 | Ildefonso et al. |

FOREIGN PATENT DOCUMENTS

| | | |
|---|---|---|
| WO | WO 02/026780 | 4/2002 |
| WO | WO 2003/078648 A2 | 9/2003 |
| WO | WO 2007/014162 A2 | 2/2007 |
| WO | WO 2008/000445 A1 | 1/2008 |
| WO | WO 2008/057434 A2 | 5/2008 |
| WO | WO 2010/005533 A2 | 1/2010 |
| WO | WO 2010/138555 A2 | 12/2010 |
| WO | WO 2011/032981 A1 | 3/2011 |
| WO | WO 2013/012806 * | 1/2013 |
| WO | WO 2013/067036 A1 | 5/2013 |
| WO | WO 2013/090318 | 6/2013 |
| WO | WO 2014/005219 A1 | 1/2014 |
| WO | WO 2014/076702 A1 | 5/2014 |

OTHER PUBLICATIONS

Lindqvist et al. Retinal glial (Muller) cells: Sensing and responding to tissue stretch. IOVS 51:1683-1690, (Year: 2010).*

Kay et al. Targeting photoreceptors via intravitreal delivery using novel, capsid-mutated AAV vectors. PLoS One 8(4):e62097, doi: 10.1371/journal.pone.006297, 12 pages, (Year: 2013).*

Ildefonso, C. J. et al. "Gene Delivery of a Viral Anti-Inflammatory Protein to Combat Ocular Inflammation" *Human Gene Therapy*, Jan. 2015, pp. 59-68, vol. 26, No. 1.

Jacobson, S. G. et al. "Safety of Recombinant Adeno-Associated Virus Type 2-RPE65 Vector Delivered by Ocular Subretinal Injection" *Molecular Therapy*, Jun. 2006, pp. 1074-1084, vol. 13, No. 6.

Johnston, J. B. et al. "A Poxvirus-Encoded Pyrin Domain Protein Interacts with ASC-1 to Inhibit Host Inflammatory and Apoptotic Responses to Infection" *Immunity*, Dec. 2005, pp. 587-598, vol. 23.

Kay, C. N. et al. "Targeting Photoreceptors via Intravitreal Delivery Using Novel, Capsid-Mutated AAV Vectors" *PLoS One*, Apr. 26, 2013, pp. 1-12, vol. 8, No. 4.

Liu, J. et al. "The immunoregulatory properties of oncolytic myxoma virus and their implications in therapeutics" *Microbes and Infection*, Dec. 2010, pp. 1-16, vol. 12, Nos. 14-15.

Lucas, A. et al. "Secreted Immunomodulatory Viral Proteins as Novel Biotherapeutics" *The Journal of Immunology*, 2004, pp. 4765-4774, vol. 173.

Rahman, M. M. et al. "Co-Regulation of NF-κB and Inflammasome-Mediated Inflammatory Responses by Myxoma Virus Pyrin Domain-Containing Protein M013" *PLoS Pathogens*, Oct. 23, 2009, pp. 1-14, vol. 5, No. 10.

Rahman, M. M. et al. "Myxoma Virus Protein M029 Is a Dual Function Immunomodulator that Inhibits PKR and Also Conscripts RHA/DHX9 to Promote Expanded Host Tropism and Viral Replication" *PLoS Pathogens*, Jul. 4, 2013, pp. 1-20, vol. 9, No. 7.

Rahman, M. M. et al. "Myxoma Virus Lacking the Pyrin-Like Protein M013 Is Sensed in Human Myeloid Cells by both NLRP3 and Multiple Toll-Like Receptors, Which Independently Activate the Inflammasome and NF-κB Innate Response Pathways" *Journal of Virology*, Dec. 2011, pp. 12505-12517, vol. 85, No. 23.

Smith, G. L. et al. "Vaccinia virus immune evasion: mechanisms, virulence and immunogenicity" *Journal of General Virology*, 2013, pp. 2367-2392, vol. 94.

Taxman, D. J. et al. "Inflammasome Inhibition as a Pathogenic Stealth Mechanism" *Cell Host & Microbe*, Jul. 22, 2010, pp. 7-11, vol. 8, No. 1.

Le, H. T. ef al. "Pyrin- and CARD-only proteins as regulators of NLR functions" *Frontiers in Immunology*, Sep. 2013, pp. 1-10, vol. 4.

U.S. Appl. No. 15/120,318, filed Aug. 19, 2016, Ildefonso et al.

EP 15752059.4, Jul. 7, 2017, Extended European Search Report.

PCT/US2015/016638, May 18, 2015, International Search Report and Written Opinion.

PCT/US2015/016638, Sep. 1, 2016, International Preliminary Report on Patentability.

Abed et al., Discovery of direct inhibitors of Keap1-Nrf2 protein-protein interaction as potential therapeutic and preventive agents. Acta Pharm Sin B. Jul. 2015;5(4):285-99. doi: 10.1016/j.apsb.2015.05.008. Epub Jul. 2, 2015. Review.

Alhakamy et al., Noncovalently associated cell-penetrating peptides for gene delivery applications. Ther Deliv. Jun. 2013;4(6):741-57. doi: 10.4155/tde.13.44. Review.

Chumanov et al., Expression, purification, and refolding of active Nrf2 transcription factor fused to protein transduction TAT tag. Protein Expr Purif. Dec. 2010;74(2):280-8. doi: 10.1016/j.pep.2010.06.017. Epub Jul. 1, 2010.

Daya et al., Gene therapy using adeno-associated virus vectors. Clin Microbiol Rev. Oct. 2008;21(4):583-93. doi: 10.1128/CMR.00008-08.

Déglon et al., Self-inactivating lentiviral vectors with enhanced transgene expression as potential gene transfer system in Parkinson's disease. Hum Gene Ther. Jan. 1, 2000;11(1):179-90.

Foti et al., Delivering multiple gene products in the brain from a single adeno-associated virus vector. Gene Ther. Nov. 2009;16(11):1314-9. doi: 10.1038/gt.2009.106. Epub Sep. 3, 2009.

Handa et al., How does the macula protect itself from oxidative stress? Mol Aspects Med. Aug. 2012;33(4):418-35. doi: 10.1016/j.mam.2012.03.006. Epub Apr. 5, 2012. Author manuscript.

Kanninen et al., Intrahippocampal injection of a lentiviral vector expressing Nrf2 improves spatial learning in a mouse model of Alzheimer's disease. Proc Natl Acad Sci U S A. Sep. 22, 2009;106(38):16505-10. doi: 10.1073/pnas.0908397106. Epub Sep. 10, 2009.

Koren et al., Cell-penetrating peptides: breaking through to the other side. Trends Mol Med. Jul. 2012;18(7):385-93. doi: 10.1016/j.molmed.2012.04.012. Epub Jun. 7, 2012.

Lee et al., NF-E2-related factor-2 mediates neuroprotection against mitochondrial complex I inhibitors and increased concentrations of intracellular calcium in primary cortical neurons. J Biol Chem. Sep. 26, 2003;278(39):37948-56. Epub Jul. 3, 2003.

Steel et al., Anti-inflammatory Effect of a Cell-Penetrating Peptide Targeting the Nrf2/Keap1 Interaction. ACS Med Chem Lett. May 10, 2012;3(5):407-410. Epub Mar. 12, 2012.

Waehler et al., Engineering targeted viral vectors for gene therapy. Nat Rev Genet. Aug. 2007;8(8):573-87. Epub Jul. 3, 2007.

Zhao et al., A novel strategy to activate cytoprotective genes in the injured brain. Biochem Biophys Res Commun. Apr. 15, 2011;407(3):501-6. doi: 10.1016/j.bbrc.2011.03.046. Epub Mar. 22, 2011.

Chan et al., IL-2/B7.1 (CD80) fusagene transduction of AML blasts by a self-inactivating lentiviral vector stimulates T cell responses in vitro: a strategy to generate whole cell vaccines for AML. Mol Ther. Jan. 2005;11(1):120-31.

Giove et al., Transduction of the inner mouse retina using AAVrh8 and AAVrh10 via intravitreal injection. Exp Eye Res. Nov. 2010;91(5):652-9. doi: 10.1016/j.exer.2010.08.011. Epub Aug. 17, 2010. Author manuscript.

Naso et al., Adeno-Associated Virus (AAV) as a Vector for Gene Therapy. BioDrugs. Aug. 2017;31(4):317-334. doi: 10.1007/s40259-017-0234-5.

(56) References Cited

OTHER PUBLICATIONS

Pang et al., Comparative analysis of in vivo and in vitro AAV vector transduction in the neonatal mouse retina: effects of serotype and site of administration. Vision Res. Feb. 2008;48(3):377-85. Epub Oct. 22, 2007.
Flotte et al., Preclinical characterization of a recombinant adeno-associated virus type 1-pseudotyped vector demonstrates dose-dependent injection site inflammation and dissemination of vector genomes to distant sites. Hum Gene Ther. Mar. 2007;18(3):245-56. doi: 10.1089/hum.2006.113.
Foti, Novel AAV-mediated therapeutic strategies for epilepsy. UNC Chapel Hill Thesis. 2008. 1-180.
Jones et al., Cell entry of cell penetrating peptides: tales of tails wagging dogs. J Control Release. Jul. 20, 2012;161(2):582-91. doi: 10.1016/j.jconrel.2012.04.003. Epub Apr. 10, 2012.
Multhoff, Heat shock protein 70 (Hsp70): membrane location, export and immunological relevance. Methods. Nov. 2007;43(3):229-37. doi: 10.1016/j.ymeth.2007.06.006.
Petrs-Silva et al., High-efficiency transduction of the mouse retina by tyrosine-mutant AAV serotype vectors. Mol Ther. Mar. 2009;17(3):463-71. doi: 10.1038/mt.2008.269. Epub Dec. 16, 2008.
Petrs-Silva et al., Novel properties of tyrosine-mutant AAV2 vectors in the mouse retina. Mol Ther. Feb. 2011;19(2):293-301. doi: 10.1038/mt.2010.234. Epub Nov. 2, 2010.
Tréhin et al., Chances and pitfalls of cell penetrating peptides for cellular drug delivery. Eur J Pharm Biopharm. Sep. 2004;58(2):209-23. doi: 10.1016/j.ejpb.2004.02.018.
Zhao et al., Age-related retinopathy in NRF2-deficient mice. PLoS One. Apr. 29, 2011;6(4):e19456. doi: 10.1371/journal.pone. 0019456.
Koerber et al., "Molecular Evolution of Adeno-Associated Virus for Enhanced Glial Gene Delivery", *The Am. Soc. of Gen. & Cell Ther.*, www.moleculartherapy.org., vol. 17, No. 12, 2088-2095, Dec. 2009.
Extended European Search Report for Application No. EP 14779372.3 dated Sep. 21, 2016.
International Search Report and Written Opinion for Application No. PCT/US2014/023262 dated Aug. 26, 2014.
International Preliminary Report on Patentability for Application No. PCT/US2014/023262 dated Sep. 24, 2015.
[No Author Listed] CARD16, Caspase recruitment domain family member 16. The Human Protein Atlas. https://www.proteinatlas.org/ENSG00000204397-CARD16/tissue#gene_information. Last Accessed Dec. 15, 2016; 3 pages.
[No Author Listed], Chain A, Apoptosis-associated speck-like protein containing a CARD. NCBI 2KN6_A. Nov. 6, 2011; http://www.ncbi.nlm.nih.gov/protein/2KN6_A. Last Accessed Aug. 6, 2016; 2 pages.
[No Author Listed], Diabetic retinopathy.www.mayoclinic.org/diseases-conditions/diabetic-retinopathy/basics/preventions/con-20023311. Last Accessed Jul. 13, 2017; 3 pages.
[No Author Listed], *Homo sapiens* ASC mRNA for apoptosis-associated speck-like protein containing a CARD, complete cds. Genbank Accession No. AB023416.2. Sep. 19, 2008; https://www.ncbi.nlm.nih.gov/nuccore/AB023416.2/. 1 page. Last accessed Apr. 1, 2019.
[No Author Listed], Pycard, Human Protein Atlas. http://www.proteinatals.org/ENSG00000103490-PYCARD/cell/CAB006853. Last Accessed Aug. 5, 2016. 4 pages.
[No Author Listed], Retinitis Pigmentosa? www.mesvision.com/knowledgeCenter/retinitusPigmentosa.htm. Last Accessed Jul. 13, 2017; 2 pages.
An et al., TAT-apoptosis repressor with caspase recruitment domain protein transduction rescues mice from fulminant liver failure. Hepatology. Aug. 2012;56(2):715-26. doi: 10.1002/hep.25697. Epub Jul. 3, 2012.
Baraibar et al., Oxidative proteome modifications target specific cellular pathways during oxidative stress, cellular senescence and aging. Exp Gerontol. Jul. 2013;48(7):620-5. doi: 10.1016/j.exger. 2012.10.007. Epub Nov. 2, 2012.
Barka et al., Production of cell lines secreting TAT fusion proteins. J Histochem Cytochem. Apr. 2004;52(4):469-77.
Bian et al., Regulated expression of caspase-12 gene in human retinal pigment epithelial cells suggests its immunomodulating role. Invest Ophthalmol Vis Sci. Dec. 2008;49(12):5593-601. doi: 10.1167/iovs.08-2116. Epub Sep. 12, 2008. Author Manuscript, 21 pages.
Brooks et al., Tat peptide-mediated cellular delivery: back to basics. Adv Drug Deliv Rev. Feb. 28, 2005;57(4):559-77. doi: 10.1016/i.addr.2004.12.001. Epub Jan. 6, 2005.
Bruewer et al., Evaluation of lateral spread of transgene expression following subretinal AAV-mediated gene delivery in dogs. PLoS One. 2013;8(4):e60218. doi: 10.1371/journal.pone.0060218. Epub Apr. 3, 2013.
Dasuri et al., Oxidative stress, neurodegeneration, and the balance of protein degradation and protein synthesis. Free Radic Biol Med. Sep. 2013;62:170-185. doi: 10.1016/j.freeradbiomed.2012.09.016. Epub Sep. 19, 2012.
Gustafsson et al., TAT protein transduction into isolated perfused hearts: TAT-apoptosis repressor with caspase recruitment domain is cardioprotective. Circulation. Aug. 6, 2002;106(6):735-9.
Ildefonso et al., Gene therapy with the caspase activation and recruitment domain reduces the ocular inflammatory response. Mol Ther. May 2015;23(5):875-84. doi: 10.1038/mt.2015.30. Epub Feb. 20, 2015.
Ildefonso et al., Targeting the Inflammasome with the Caspase Activation Recruitment Domain (CARD) in an In vitro Model of RPE Inflammation. ARVO 2013 Annual Meeting. May 5-9, 2013. Abstract 148. Investigative Opthalmology & Visual Science Jun. 2013, vol. 54, 148.
Johnson et al., Cell penetrating peptide POD mediates delivery of recombinant proteins to retina, cornea and skin. Vision Res. Mar. 31, 2010;50(7):686-97. doi: 10.1016/j.visres.2009.08.028. Epub Sep. 3, 2009. Author Manuscript, 20 pages.
Lee et al., Cop, a caspase recruitment domain-containing protein and inhibitor of caspase-1 activation processing. J Biol Chem. Sep. 14, 2001;276(37):34495-500. doi: 10.1074/jbc.M101415200. Epub Jun. 29, 2001.
Lubell-Snyder et al., Placentophagia: stir-fry, smoothie or raw? Midwifery Today Int Midwife. 2011-2012 Winter;(100):21-3.
Martinon et al., Inflammatory caspases: linking an intracellular innate immune system to autoinflammatory diseases. Cell. May 28, 2004;117(5):561-74. doi: 10.1016/j.cell.2004.05.004.
Neuss et al., The apoptotic regulatory protein ARC (apoptosis repressor with caspase recruitment domain) prevents oxidant stress-mediated cell death by preserving mitochondrial function. J Biol Chem. Sep. 7, 2001;276(36):33915-22. doi: 10.1074/jbc. M104080200. Epub Jul. 3, 2001.
Oduntan et al., A review of the role of oxidative stress in the pathogenesis of eye diseases. S Afr Optom. 2011; 70(4): 191-199.
Olry et al., Renfield's syndrome: a psychiatric illness drawn from Bram Stoker's Dracula. J Hist Neurosci. Oct. 2011;20(4):368-71. doi: 10.1080/0964704X.2011.595655.
Palacios-Rodriguez et al., Polypeptide modulators of caspase recruitment domain (CARD)-CARD-mediated protein-protein interactions. J Biol Chem. Dec. 30, 2011;286(52):44457-66. doi: 10.1074/jbc.M111.255364. Epub Nov. 7, 2011.
Rathinam et al., Regulation of inflammasome signaling. Nat Immunol. Mar. 19, 2012;13(4):333-42. doi: 10.1038/ni.2237. Author Manuscript, 23 pages.
Rosenzweig et al., The NLRP3 inflammasome is active but not essential in endotoxin-induced uveitis. Inflamm Res. Mar. 2012; 61(3): 225-231. Published online Nov. 26, 2011. doi: 10.1007/s00011-011-0404-8. Author Manuscript, 13 pages.
Sakamoto et al., Inhibition of experimental proliferative vitreoretinopathy by retroviral vector-mediated transfer of suicide gene. Can proliferative vitreoretinopathy be a target of gene therapy? Ophthalmology. Oct. 1995;102(10):1417-24. doi: 10.1016/s0161-6420(95)30850-0.
Salminen et al., Endoplasmic reticulum stress in age-related macular degeneration: trigger for neovascularization. Mol Med. Nov.-Dec. 2010;16(11-12):535-42. doi: 10.2119/molmed.2010.00070. Epub Jul. 27, 2010.

(56) References Cited

OTHER PUBLICATIONS

Samardzija et al., Caspase-1 ablation protects photoreceptors in a model of autosomal dominant retinitis pigmentosa. Invest Ophthalmol Vis Sci. Dec. 2006;47(12):5181-90. doi: 10.1167/iovs.06-0556.

Srinivasula et al., The PYRIN-CARD protein ASC is an activating adaptor for caspase-1. J Biol Chem. Jun. 14, 2002;277(24):21119-22. doi: 10.1074/jbc.C200179200. Epub Apr. 19, 2002.

Stehlik et al., Apoptosis-associated speck-like protein containing a caspase recruitment domain is a regulator of procaspase-1 activation. J Immunol. Dec. 1, 2003;171(11):6154-63.

Stehlik et al., COPs and POPs: modulators of inflammasome activity. J Immunol. Dec. 15, 2007;179(12):7993-8. doi: 10.4049/jimmunol.179.12.7993.

Stein, J., Afterbirth: It's What's For Dinner. Time. Jul. 13, 2009; 174(1):60. Last Accessed Jan. 1, 2016. 2 pages.

Tarallo et al., DICER1 loss and Alu RNA induce age-related macular degeneration via the NLRP3 inflammasome and MyD88. Cell. May 11, 2012;149(4):847-59. doi: 10.1016/j.cell.2012.03.036. Epub Apr. 26, 2012. Supplemental Information, S1-10.

Trittibach et al., Lentiviral-vector-mediated expression of murine IL-1 receptor antagonist or IL-10 reduces the severity of endotoxin-induced uveitis. Gene Ther. Nov. 2008;15(22):1478-88. doi: 10.1038/gt.2008.109. Epub Jun. 26, 2008. Author Manuscript, 22 pages.

Tseng et al., NLRP3 inflammasome activation in retinal pigment epithelial cells by lysosomal destabilization: implications for age-related macular degeneration. Invest Ophthalmol Vis Sci. Jan. 7, 2013;54(1): 110-20. doi: 10.1167/iovs.12-10655.

Verma et al., ACE2 and Ang-(1-7) confer protection against development of diabetic retinopathy. Mol Ther. Jan. 2012;20(1):28-36. doi: 10.1038/mt.2011.155. Epub Jul. 26, 2011.

Zapata, G.L., The Role of Oxidative Stress in Ocular Disease. Humana Press. Feb. 4, 2011; 113-131.

U.S. Appl. No. 13/321,104, filed Mar. 5, 2012, Li et al.

PCT/US2010/036153, Mar. 23, 2011, International Search Report and Written Opinion.

PCT/US2010/036153, Dec. 8, 2011, International Preliminary Report on Patentability.

PCT/US2015/020001, Jun. 24, 2015, International Search Report.

PCT/US2015/020001, Sep. 22, 2016, International Preliminary Report on Patentability.

EP 15761543.6, Jul. 28, 2017, Supplementary European Search Report.

* cited by examiner

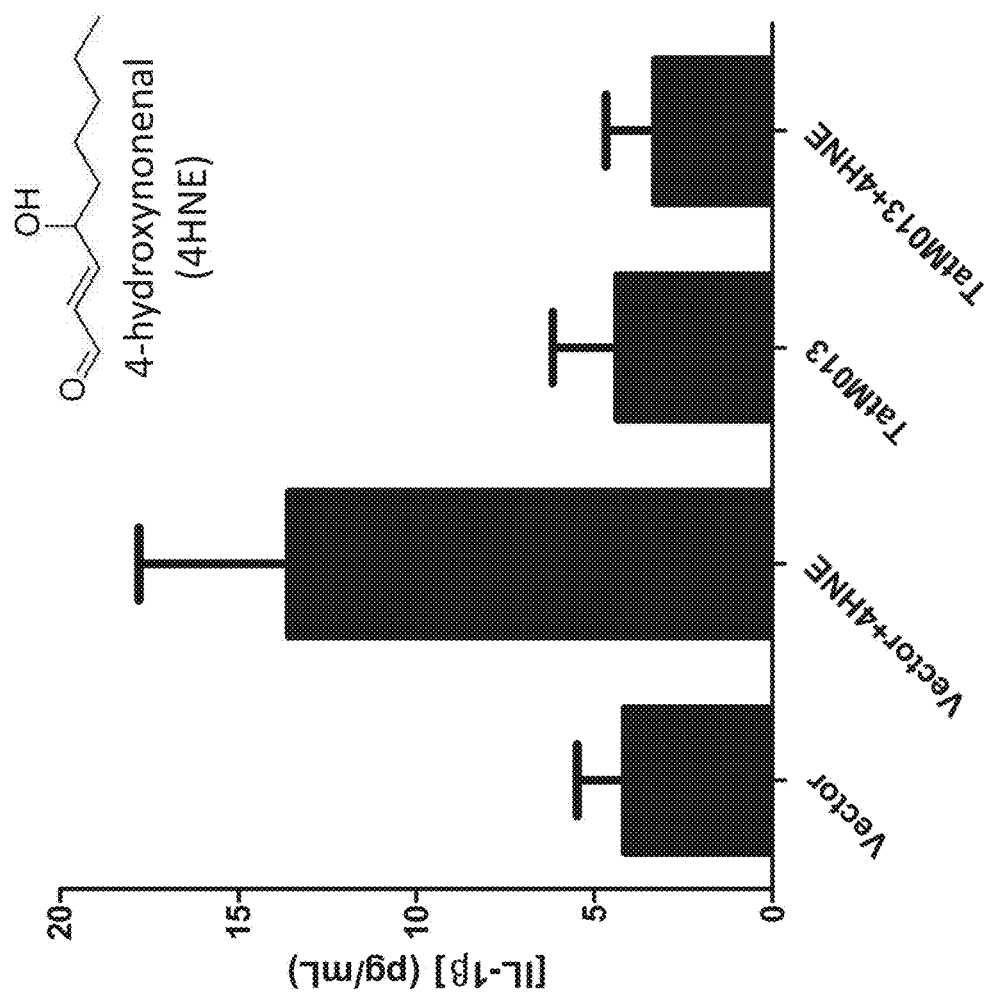

GFP sGFP-FCS-TatM013

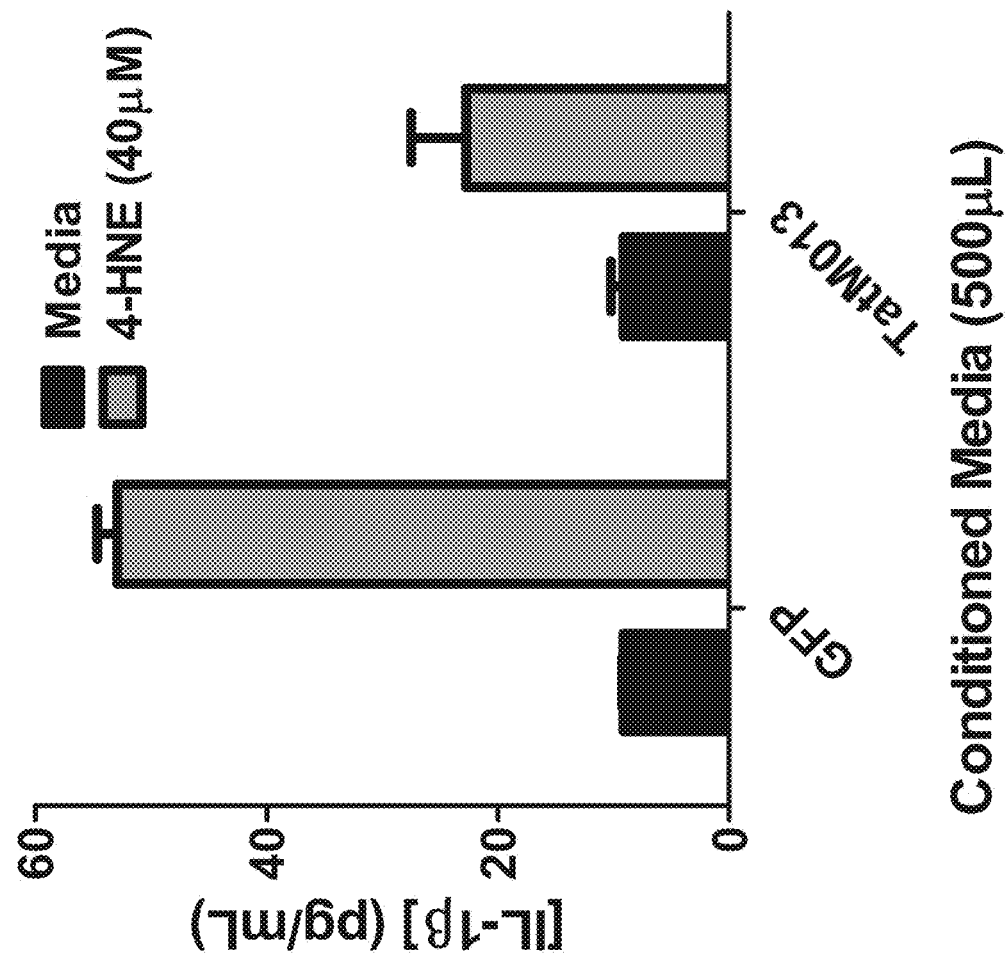

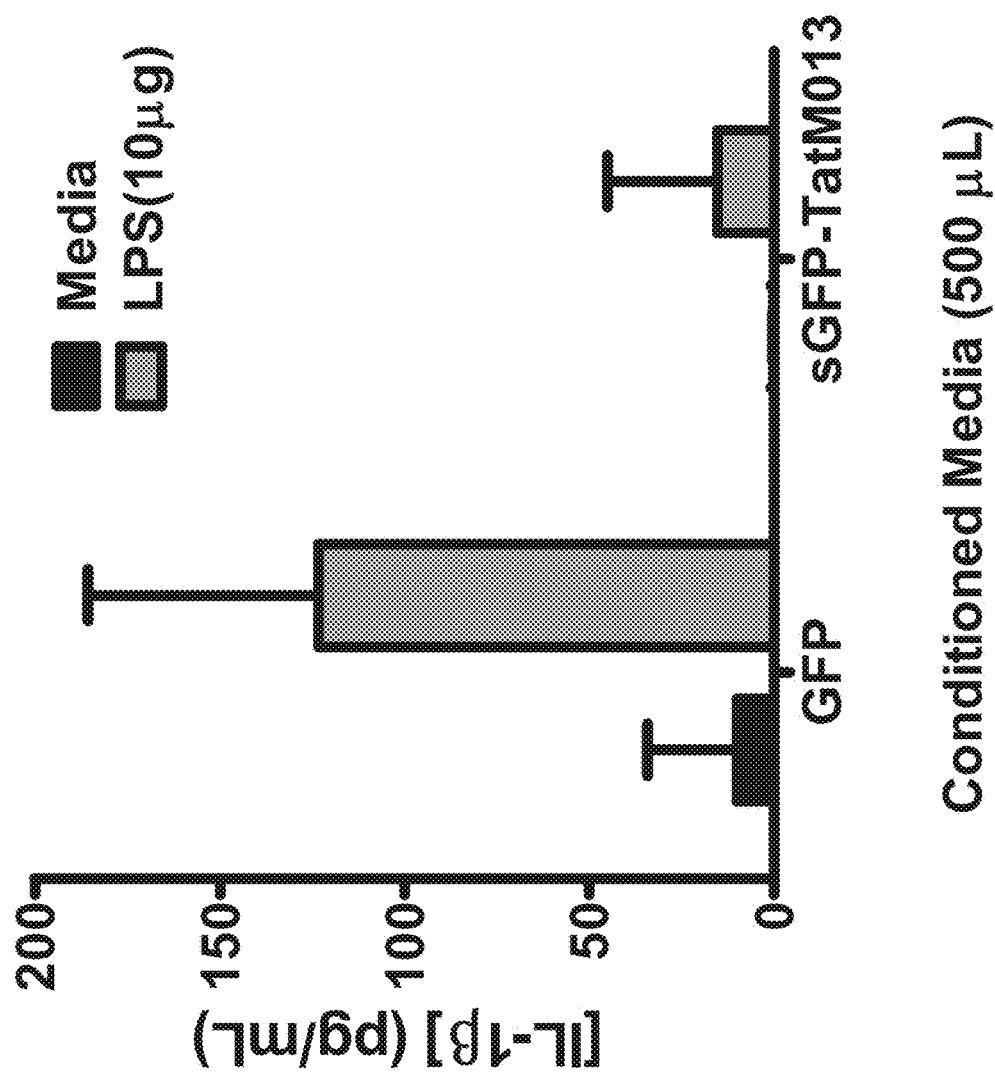

AAV2QUAD-sGFP-TatM013

AAV2QUAD-GFP

AAV2QUAD-sGFP-TatM013

AAV2QUAD-GFP

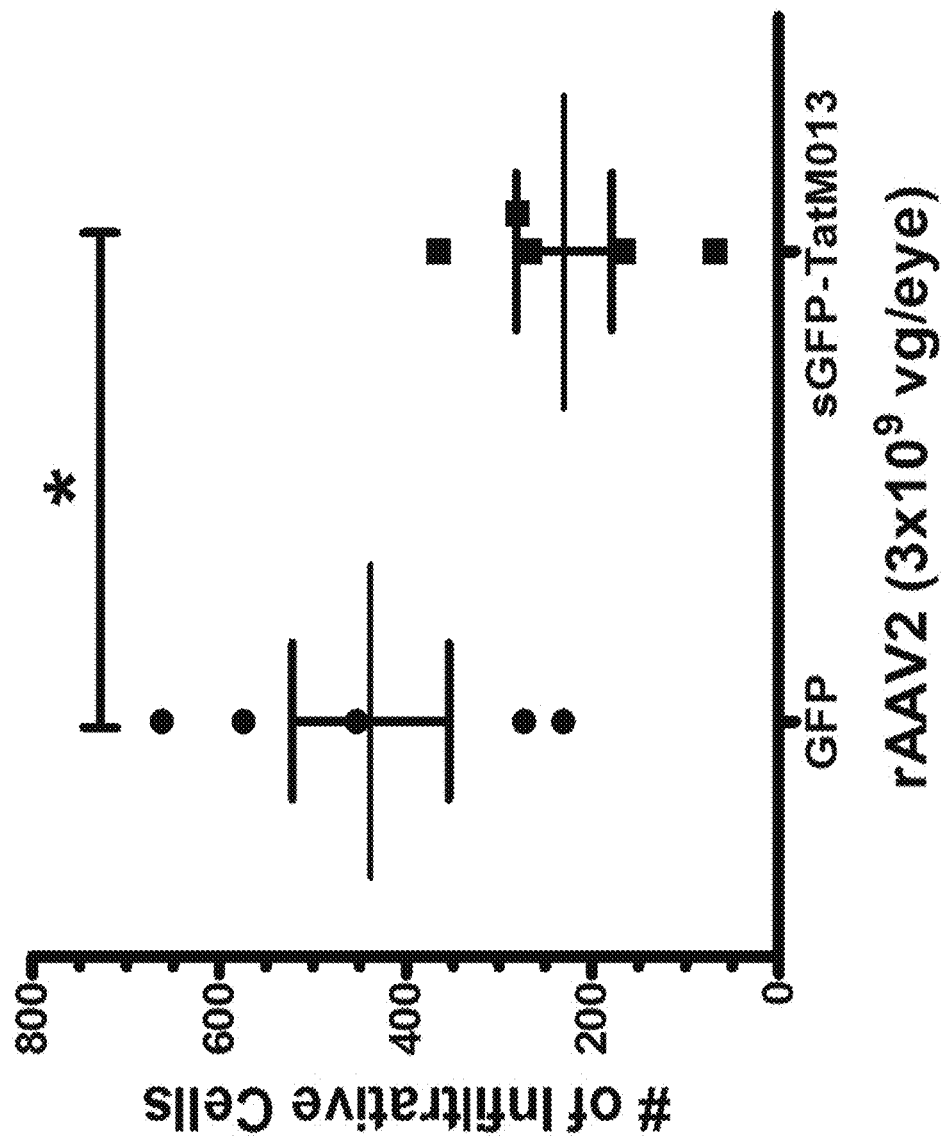

US 11,685,767 B2

USE OF AAV-EXPRESSED M013 PROTEIN AS AN ANTI-INFLAMMATORY THERAPEUTIC

CROSS-REFERENCE TO RELATED APPLICATIONS

The present application claims priority to PCT Intl. Pat. Appl. No. PCT/US2015/020001; filed Mar. 11, 2015, which claims the benefit of U.S. Prov. Pat. Appl. No. 61/951,294; filed Mar. 11, 2014, the contents of each of which is specifically incorporated herein in its entirety by express reference thereto.

STATEMENT REGARDING FEDERALLY SPONSORED RESEARCH OR DEVELOPMENT

This invention was made with government support under Grant Nos. AI100987, EY002025, and EY021721 awarded by the National Institutes of Health. The government has certain rights in the invention.

BACKGROUND OF THE INVENTION

Names of the Parties to a Joint Research Agreement

Not Applicable.

Field of the Invention

The present disclosure relates generally to the fields of molecular biology and virology, and in particular, to the development of gene delivery vehicles. In this application, the use of a modified, cell-permeable version of the viral-specific M013 protein as an anti-inflammatory reagent is described. Methods are also provided for treating tissue-specific inflammation with the disclosed genetic constructs, using inflammatory eye disease as an exemplar disease target and AAV as the delivery vector to express the modified M013 protein in cells within the inflamed eye tissue.

DESCRIPTION OF RELATED ART

Dry age-related macular degeneration (AMD) has been associated with an increase in oxidative stress and inflammatory processes within the retina. Oxidized molecules, like 4-hydroxynonenal (4-HNE) and activated complement components, have been detected in the eyes of dry AMD patients, further evidencing the role of these processes in this disease.

What is lacking in the prior art are viral vectors that can be used to deliver therapeutic constructs to selected cell populations in vitro or in vivo. The development of such vectors, and compositions comprising them would provide a major advancement in human gene therapy, and particularly in the treatment of inflammatory-mediated diseases such as arthritis, diabetic retinopathy, dry AMD, vasculitis, recurrent uveitis, Bechet's disease, Lupus erythematosus, nephritis, and the like.

BRIEF SUMMARY OF THE INVENTION

The present disclosure overcomes these and other limitations inherent in the prior art by providing AAV vector constructs that are capable of, and optimized for, delivering anti-inflammatory peptides, such as those derived from the viral M013 protein, to selected mammalian cells and/or tissues. The invention also provides a robust methodology for the tissue-specific treatment and/or amelioration of one or more symptoms of oxidative stress and/or inflammation in a subject mammal. In particular, the invention provides novel and non-obvious AAV vector-based constructs that deliver a secretable, cell-penetrating, and virally-derived M013 gene product to selected mammalian cells. These genetic constructs encode M013 polypeptides that inhibit one or more proinflammatory cytokines [including, for example, IL-1beta (IL-1β) and IL-18] in a variety of abnormal conditions in mammals, including, for example, ocular diseases such as age-related macular degeneration (AMD), arthritis, diabetic retinopathy, Bechet's disease, vasculitis, nephritis, lupus erythematosus, and recurrent uveitis.

The invention also provides new and useful methods for treating a variety of abnormal conditions, diseases, dysfunctions, and/or disorders that may result from, or be exacerbated by, one or more cellular oxidative stress pathways, and/or one or more steps of the inflammatory response process in mammals.

The present disclosure overcomes limitations in the prior art by providing new AAV-based gene therapy vectors that deliver a secretable, cell-penetrating peptide, such as viral M013 peptide or polypeptide, to one or more target host cells or tissues. When expressed in suitably-transformed mammalian host cells, the expressed gene product inhibits a variety of endogenous proinflammatory cytokines (including, without limitation, interleukins such as IL-1β and IL-18). In an exemplary embodiment, gene therapy constructs of the invention comprising M013-based pepties were useful in inhibiting the inflammatory response process in an established mammalian model of dry AMD.

The constructs described herein provide new and useful treatment strategies for a variety of mammalian diseases, conditions or disorders that are associated with, caused by, or exacerbated due to, one or more cellular oxidative stress responses or one or more steps in the inflammation process.

In exemplary embodiments, a viral-vectored tatM013 fusion peptide was exploited for treating tissue-based inflammatory disorders, using a method in which the vector construct was directly delivered to one or more selected target cell populations. Importantly, the viral-based expression constructs of the present disclosure (and in particular, those packaged in AAV-based virions) have been shown to reduce inflammation in a number of disease processes for which there are currently no effective therapies. The disclosed compositions and methods provide new therapeutic modalities for a host of inflammatory-mediated mammalian diseases, including, for example, those of the eye, the gut, and/or one or more internal organs or target tissues to which such viral vectors, such as rAAV-based expression cassettes can be safely, reliably, and suitably delivered.

Advantageously, the viral vectors and expression constructs of the present disclosure (as well as infectious virions and viral particles containing them) have an improved efficiency in transducing one or more of cells of a mammal, and in particular, one or more cells of a human eye, and facilitating the expression of M013 protein in cells transformed with the virus. In particular embodiments, the use of capsid-protein-modified viral particles to deliver the expression constructs of interest, has resulted in highly-efficient transduction of selected mammalian cells with populations of the therapeutic viral particles.

In an overall and general sense, the invention provides isolated and purified polynucleotides that encode one or more of the disclosed rAAV vectors described herein, as well as pluralities of infectious adeno-associated viral virions that contain such a polynucleotide. Preferably, the vector constructs of the present disclosure include at least one nucleic acid segment that encodes at least one M013-derived peptide or protein operably linked to a promoter that is capable of expressing the nucleic acid segment in suitable mammalian cells that have been transformed with the vector construct.

In the practice of the invention, the disclosed rAAV vectors will preferably include at least one polynucleotide that comprises one or more promoters, one or more enhancers, one or more post-transcriptional regulatory sequences, one or more polyadenylation signals, or any combination thereof, operably linked to the nucleic acid segment that encodes the selected M013-derived therapeutic protein or peptide to permit expression of the construct in selected mammalian host cells.

In certain embodiments, such promoter(s) may include a homologous promoter, a heterologous promoter, an endogenous promoter, an exogenous promoter, a synthetic promoter, a hybrid promoter, a viral promoter, a cell-specific promoter, a tissue-specific promoter, or any combination thereof that is/are capable of expressing the M013-encoding nucleic acid segment in selected cells and/or tissues of a mammalian subject.

rAAV vectors prepared in accordance with the present disclosure may also optionally further include one or more additional nucleic acid sequences that are each operably linked to the therapeutic agent-encoding nucleic acid segment. Exemplary sequences include, but are not limited to, one or more selected from the group consisting of a viral-derived enhancer sequence, a mammalian-derived enhancer sequence, a synthetic enhancer, a cell- or tissue-specific enhancer sequencer, one or more inverted terminal repeats, one or more multiple cloning sites, restriction cleavage sites, polyadenylation signals, post-transcriptional regulatory sequences, secretion signal sequences, or any combination thereof.

Exemplary post-transcriptional regulatory sequences include, but are not limited to, woodchuck hepatitis virus post-transcription regulatory elements, polyadenylation signal sequences, intron/exon junctions/splicing signals, synthetic elements, or any combination thereof.

The viral vectors of the present disclosure may also optionally further include an additional nucleic acid sequence region that comprises, consists essentially of, or consists of, one or more polylinkers, restriction sites, and/or multiple cloning region(s) to facilitate insertion (cloning) of one or more selected genetic elements, genes of interest, or therapeutic or diagnostic constructs into the vector at a pre-determined site.

In further aspects of the present disclosure, the exogenous polynucleotide(s) that may be delivered into suitable host cells by the disclosed viral vectors are preferably of mammalian origin, with polynucleotides encoding one or more polypeptides or peptides of human, non-human primate, porcine, bovine, ovine, feline, canine, equine, epine, caprine, or lupine origin also being preferred for certain uses of the disclosed vector compositions.

In certain embodiments, the disclosed viral vectors will further optionally include a second nucleic acid segment that expresses or encodes one or more diagnostic or therapeutic molecules, including, without limitation, one or more polypeptides, peptides, ribozymes, peptide nucleic acids, siRNA's, RNAi's, antisense oligonucleotides, antisense polynucleotides, antibodies, antigen binding fragments, or any combination thereof. Such additional therapeutic agents may include, without limitation, one or more agonists, antagonists, anti-apoptosis factors, inhibitors, receptors, cytokines, cytotoxins, erythropoietic agents, glycoproteins, growth factors, growth factor receptors, hormones, hormone receptors, interferons, interleukin inhibitors, interleukin receptors, nerve growth factors, neuroactive peptides, neuroactive peptide receptors, proteases, protease inhibitors, protein decarboxylases, protein kinases, protein kinase inhibitors, enzymes, receptor binding proteins, transport proteins or one or more inhibitors thereof, serotonin receptors, or one or more uptake inhibitors thereof, serpins, serpin receptors, tumor suppressors, diagnostic molecules, molecular markers, chemotherapeutic agents, cytotoxins, or any combination thereof.

When combinational gene therapies are desired, two or more different molecules may be produced from a single rAAV expression system, or alternatively, a selected host cell may be transfected with two or more unique rAAV expression systems, each of which may comprise one or more distinct polynucleotides that encode one or more diagnostic and/or therapeutic agents.

The viral vectors of the present disclosure are preferably rAAV vectors, including, without limitation, those derived from, or comprised within a virion having a serotype that is selected from the group consisting of AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), AAV serotype 12 (AAV12), or any other serotype as known to one of ordinary skill in the viral arts.

In related embodiments, the invention further provides populations and pluralities of viral vectors, virions, infectious viral particles, or host cells that include one or more nucleic acid segments that encode a CPP, such as an M013-specific protein or peptide, operably linked to a selected promoter capable of expressing the encoded CPP in at least one mammalian cell of interest.

The invention further provides composition and formulations that include one or more of the proteins, nucleic acid segments, viral vectors, host cells, or viral particles of the present disclosure together with one or more pharmaceutically-acceptable buffers, diluents, or excipients. Such compositions may be included in one or more diagnostic or therapeutic kits, for diagnosing, preventing, treating or ameliorating one or more symptoms of a mammalian disease, injury, disorder, trauma or dysfunction, and in particular, for treatment of oxidative stress and/or inflammation in one or more human cells.

The invention further includes a method for providing a mammal in need thereof with a diagnostically- or therapeutically-effective amount of a selected M013-derived therapeutic agent, the method comprising providing to a cell, tissue or organ of a mammal in need thereof, an amount of one or more of the disclosed CPP-encoding rAAV vectors (such as those expressing M013 peptide; and for a time effective to provide the mammal with a diagnostically- or a therapeutically-effective amount of the encoded peptide.

In another embodiment, the invention also provides a method for diagnosing, preventing, treating, or ameliorating at least one or more symptoms of a disease, a disorder, a dysfunction, an injury, an abnormal condition, or trauma in a mammal. In an overall and general sense, the method includes at least the step of administering to a mammal in need thereof one or more of the disclosed M013-encoding rAAV genetic constructs, in an amount and for a time sufficient to diagnose, prevent, treat or ameliorate the one or more symptoms of the disease, disorder, dysfunction, injury, abnormal condition, or trauma in the mammal.

The invention also provides a method of transducing a population of mammalian cells. In an overall and general sense, the method includes at least the step of introducing into one or more cells of the population, a composition that comprises an effective amount of one or more of the M013-expressing rAAV vector constructs as disclosed herein.

In a further embodiment, the invention also provides isolated nucleic acid segments that encode one or more M013-specific proteins or peptides, as well as recombinant vectors, virus particles, infectious virions, and isolated host cells that comprise one or more of the modified M013-specific protein-encoding nucleic acids as described herein.

Additionally, the present disclosure provides compositions, as well as therapeutic and/or diagnostic kits that include one or more of the disclosed viral vector compositions, formulated with one or more additional ingredients, or prepared with one or more instructions for their use.

The invention also demonstrates methods for making, as well as methods of using the disclosed viral vectors in a variety of ways, including, for example, ex situ, in vitro and in vivo applications, methodologies, diagnostic procedures, and/or gene therapy methods. The disclosed vectors are particularly suited for viral vector-based human gene therapy regimens, and for delivering one or more genetic constructs, including, for example, an M013 peptide, to one or more populations of selected mammalian cells, either in vivo or in vitro.

In one aspect, the invention provides compositions comprising recombinant adeno-associated viral (AAV) vectors, virions, viral particles, and pharmaceutical formulations thereof, useful in methods for delivering genetic material encoding one or more beneficial or therapeutic product(s) to mammalian cells and tissues. In particular, the compositions and methods of the invention provide a significant advancement in the art through their use in the treatment, prevention, and/or amelioration of symptoms of one or more mammalian diseases associated with one or more oxidative stress or inflammatory responses.

In particular, the invention provides rAAV-based expression constructs that encode one or more mammalian therapeutic agent(s) (including, but not limited to, for example, M013-derived protein(s), polypeptide(s), peptide(s), enzyme(s), antibodies, antigen binding fragments, as well as variants, and/or active fragments thereof, for use in the treatment, prophylaxis, and/or amelioration of one or more symptoms of a mammalian disease, dysfunction, injury, and/or disorder.

In other embodiments, the invention also provides viral vectors that are comprised within an infectious viral particle or a virion, as well as pluralities of such virions or infectious particles. Such vectors and virions may be comprised within one or more diluents, buffers, physiological solutions, or pharmaceutical vehicles, or formulated for administration to a mammal in one or more diagnostic, therapeutic, and/or prophylactic regimens. The vectors, virus particles, virions, and pluralities thereof of the present disclosure may also be provided in excipient formulations that are acceptable for veterinary administration to selected livestock, exotics, domesticated animals, and companion animals (including pets and such like), as well as to non-human primates, zoological or otherwise captive specimens, and such like.

Compositions comprising one or more of the disclosed viral vectors, expression systems, infectious viral particles, or host cells also form part of the present disclosure, and particularly those compositions that further comprise at least a first pharmaceutically-acceptable excipient for use in therapy, and for use in the manufacture of medicaments for the treatment of one or more mammalian diseases, disorders, dysfunctions, or trauma, such as oxidative stress and/or inflammation, and/or related cellular processes.

Such pharmaceutical compositions may optionally further comprise one or more diluents, buffers, liposomes, a lipid, a lipid complex. Alternatively, the vectors of the present disclosure may be comprised within a plurality of microspheres, nanoparticles, liposomes, or a combination thereof. Pharmaceutical formulations suitable for administration to one or more cells, tissues, and/or organs of a human are particularly preferred.

Kits comprising one or more of the disclosed viral vectors (as well as one or more virions, viral particles, transformed host cells or pharmaceutical compositions comprising such vectors); and instructions for using such kits in one or more therapeutic, diagnostic, and/or prophylactic clinical embodiments are also provided by the present disclosure. Such kits may further comprise one or more reagents, restriction enzymes, peptides, therapeutics, pharmaceutical compounds, or means for delivery of the composition(s) to host cells, or to an animal (e.g., syringes, injectables, and the like). Exemplary kits include those for treating, preventing, or ameliorating the symptoms of a disease, deficiency, dysfunction, and/or injury, or may include components for the large-scale production of the viral vectors themselves, such as for commercial sale, or for use by others, including e.g., virologists, medical professionals, and the like.

Such kits may also further include one or more rAAV packaging components, such as a) a host cell that expresses at least one rep gene and/or at least one cap gene, b) a helper virus gene product; c) a helper virus, such as adenovirus or herpes virus, or d) any combination thereof to facilitate packaging of the expression vectors into suitable virions or infectious viral particles.

Another important aspect of the present disclosure concerns methods of use of the disclosed rAAV vectors, virions, expression systems, compositions, and host cells described herein in the preparation of medicaments for treating or ameliorating at least one symptom of a disease, a dysfunction, a disorder, an abnormal condition, a deficiency, injury, or trauma in an animal, and in particular, in one or more cells or tissues of a vertebrate mammal. Such methods generally involve direct administration to the mammal in need thereof, one or more of the disclosed CPP (and preferably M013 peptide)-expressing rAAV vectors, virions, viral particles, host cells, compositions, or pluralities thereof, in an amount and for a time sufficient to treat or ameliorate one or more symptoms of such a disease, dysfunction, disorder, abnormal condition, deficiency, injury, or trauma in the affected animal. The compositions of the invention may also be used for the diagnosis, and/or prophylaxis of one or more animals suspected of having such a condition, as well as for administration to one or more animals determined to be at risk for developing one or more such conditions.

BRIEF DESCRIPTION OF THE DRAWINGS

The following drawings form part of the present specification and are included to demonstrate certain aspects of the present disclosure. The patent or application file contains at least one drawing executed in color. Copies of this patent or patent application publication with color drawing(s) will be provided by the Office upon request and payment of the necessary fee.

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates. The invention may be better understood by reference to the following description taken in conjunction with the accompanying drawings, in which like reference numerals identify like elements, and in which.

DESCRIPTION OF ILLUSTRATIVE EMBODIMENTS

Figure 1A:
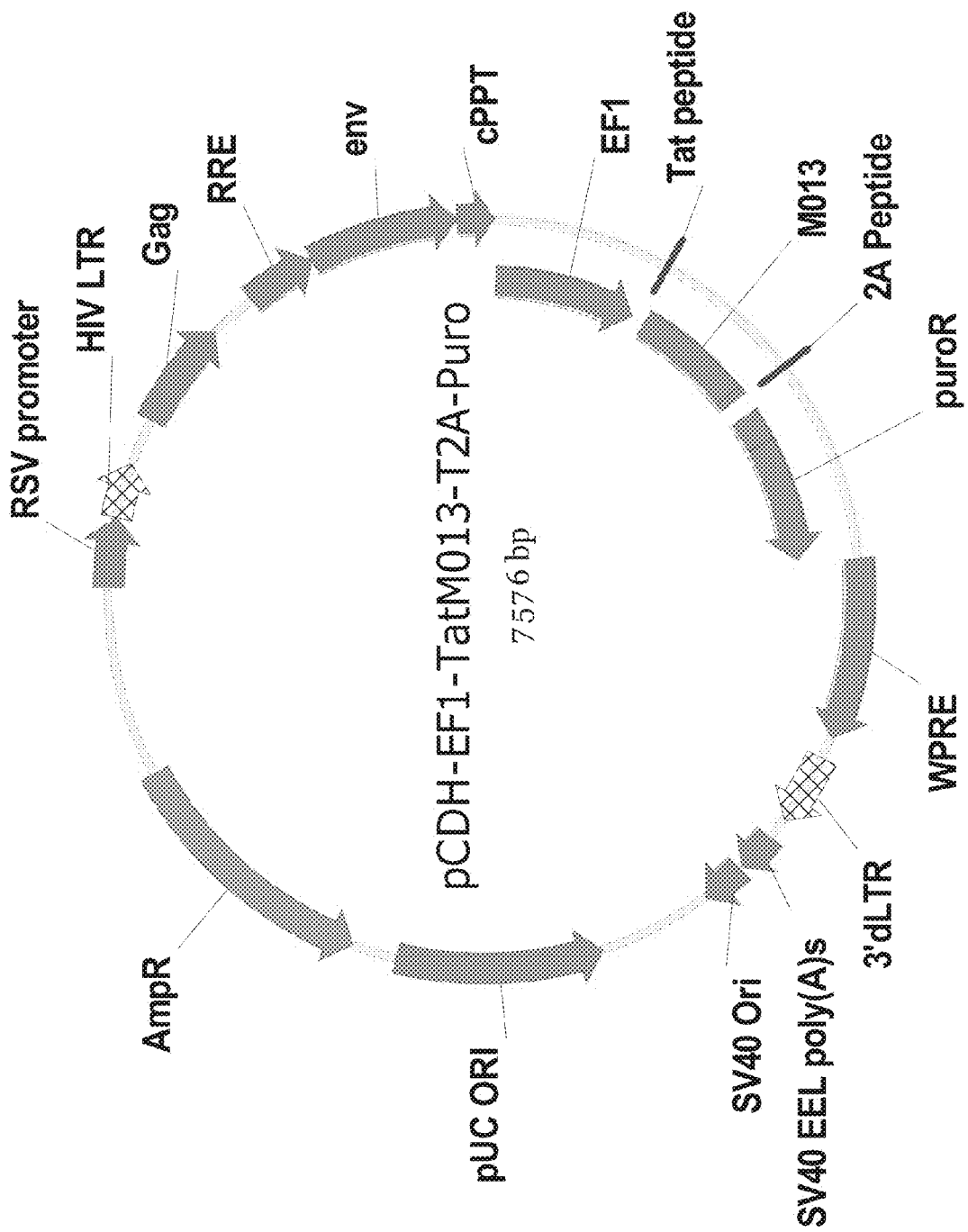
FIG. 1A, FIG. 1B, and FIG. 1C show a myxoma virus M013 fusion protein construct can be used to inhibit interleukin (IL)-1β sec whereas sGFP-TatM013 had a punctate pattern characteristic of proteins within the secretory pathway (Kakihana et al., 2013; Stow and Murray, 2013; Reinhardt et al., 2014) (FIG. 5B). This result suggested that the sGFP-TatM013 gene product could be expressed, and targeted for secretion.
Figure 1B:
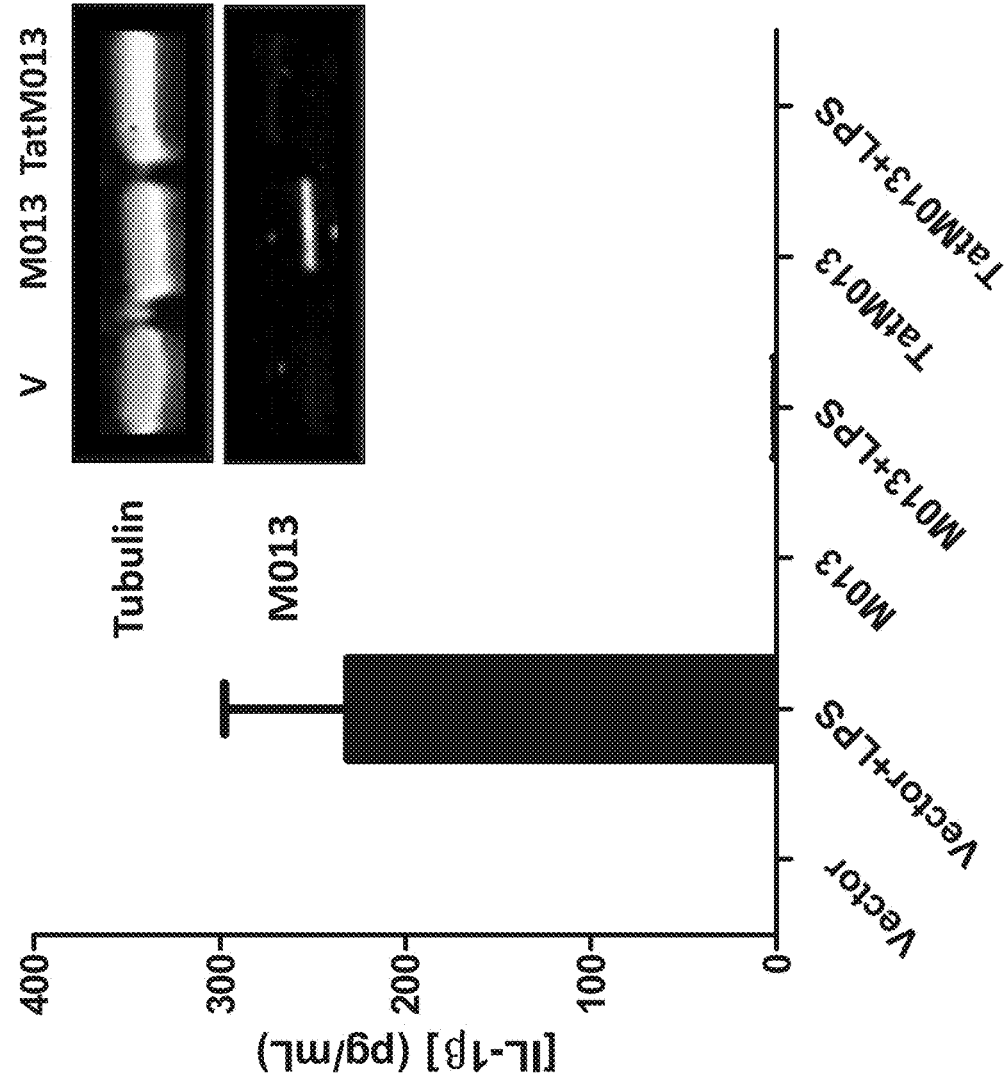

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Inflammation of the retina is a contributing factor in ocular diseases such as uveitis, diabetic retinopathy, and age-related macular degeneration (AMD). The M013 immunomodulatory protein from myxoma virus has been shown to interfere with the proinflammatory signaling pathways involving both the NLRP3 inflammasome and NF-κB. In the present application, the inventors have developed and characterized an adeno-associated viral (AAV) vector that delivers a secretable and cell-penetrating form of the M013 protein (TatM013). The expressed TatM013 protein was secreted and blocked the endotoxin-induced secretion of interleukin (IL)-1β in monocyte-derived cells and the reactive aldehyde-induced secretion of IL-1β in retinal pigment epithelium cells. The local anti-inflammatory effects of AAV-delivered TatM013 were evaluated in an endotoxin-induced uveitis (EIU) mouse model after intravitreal injection of mice with an AAV2-based vector carrying either TatM013 fused to a secreted green fluorescent protein (GFP) tag (sGFP-TatM013) or to GFP itself. Expression of the sGFP-TatM013 transgene was demonstrated by fluorescence funduscopy in living mice. In EIU, the number of infiltrating cells and the concentration of IL-1β in the vitreous body were significantly lower in the eyes injected with AAV-sGFP-TatM013 compared with the eyes injected with control AAV-GFP. These results suggested that a virus-derived inhibitor of the innate immune response, when delivered via AAV, provided an effective and generalized therapy for treatment of various inflammatory diseases of the eye.

Dry age-related macular degeneration (AMD) has been associated with an increase in oxidative stress and inflammatory processes within the retina. Oxidized molecules like 4-hydroxynonenal (4-HNE) and activated complement components have been detected in the eyes of dry AMD patients, supporting the role of these processes in the diseases.

Certain viral proteins encoded by large DNA viruses possess potent anti-inflammatory properties. In this application, the development of a modified cell-permeable version of one specific viral protein called M013 as an anti-inflammatory reagent to treat tissue-specific inflammation is disclosed. Using inflammatory eye disease as an exemplar disease target, AAV delivery vectors were developed that expressed a modified M013 protein in cells within the inflamed eye tissue.

Many drugs and reagents have been developed to treat pro-inflammatory diseases and some of these therapeutic compounds are derived from natural biological organisms, such as secreted anti-inflammatory proteins expressed by larger DNA viruses (reviewed in Lucas and McFadden, 2004). Unlike standard small molecule drugs and typical biological reagents such as monoclonal antibodies against single inflammatory targets, which tend to be mono-functional and act on one specific cellular target or pathway, viral proteins have evolved over millions of years to recognize multiple targets and pathways.

In the present disclosure, the M013 protein of myxoma virus [which is normally expressed as a small cytoplasmic protein that inhibits two distinct cellular inflammatory pathways: the inflammasome and the NFkB signaling pathways, (Rahman, et al., 2013; Rahman et al., 2009)] has been exploited as a therapeutic for treating inflammatory-mediated conditions in mammals.

The M013 protein is relatively small (188 amino acids), contains a single pyrin domain, and physically interacts with two separate host proteins that regulate cellular inflammatory pathways: ASC-1 (a key scaffolding component of cellular inflammasomes) and NFkB1/p105 (a key precursor utilized for NFkB signaling). Thus, the expressed viral M013 protein shuts off two powerful cellular pro-inflammatory signaling cascades: inflammasomes that control the secretion of inflammatory cytokines like IL-1β and IL-18, and NFkB signaling that controls the secretion of another class of pro-inflammatory cytokines such as TNF, interferon, and IL-6.

Unlike secreted viral proteins that can be expressed as recombinant proteins and then used directly in patients as therapeutic anti-inflammatory protein-based drugs (Arsenault et al., 2012), cytoplasmic proteins such as M013 must be delivered genetically—that is, an M013-encoding nucleic acid segment must be introduced into cells using a suitable vector, and that nucleic acid segment must be expressed inside the target cells to produce the encoded cytoplasmic protein. Thus, for proteins such as M013 (or for derivatives based on the M013 peptide) to be useful as a therapeutic agent in a mammal, suitable vectors (such as rAAV) must be engineered, and delivered to cells by an appropriate gene therapy protocol. For their use in the treatment of humans, such vectors must also be FDA-approved. The present disclosure provides enabling technology to meet these essential requirements.

Although a nucleic acid encoding the reporter molecule, GFP, has been utilized in the exemplary experimental results presented in the following Examples, the invention is not limit to constructs employing GFP, or for that matter, constructs employing one or more other "reporter" molecules or other gene products used primarily for visualization of the experimental results using, for example, microscopy. In fact, in many embodiments directed to therapeutic uses of the disclosed constructs, a variety of nucleic acid segments may be employed in place of the GFP reporter molecules exemplified herein. Such nucleic acids segments may include, without limitation, those encoding one or more proteins such as human serum albumin (including, without limitation, PMID:6171778 or PMID:6275391); opticin (including, without limitation, PMID:10636917 or PMID:22669977); a bacterial dihidrofolate reductase (or a destabilization domain thereof) (such as the *E. coli* DHFR destabilization domain, PMID:20851347 or PMID:23029456, etc.), a FK506 bining protein (FKBP) destabilization domain (such as the domain from the FK506 binding protein that allows the stabilization of a fused protein only in the presence of its ligand Shield-1, e.g., PMID:16959577, PMID:18836461); or one or more combinations thereof. Each of these proteins is known to those of ordinary skill in the art, and the amino acid sequences for each are on record in conventional sequence databases and archives (e.g., SwissProt ID's NP_000468, CAB53459, AIW05158, and AAD40379, respectively). The constructs may also be engineered to further include one or more additional diagnostic and/or therapeutic-encoding nucleic acid segments where indicated.

rAAV Vectors

Recombinant adeno-associated virus (AAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, i.e., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009).

EXEMPLARY DEFINITIONS

In accordance with the present disclosure, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs.

The following references provide one of skill with a general definition of many of the terms used in this invention: *Dictionary of Biochemistry and Molecular Biology*, (2$^{nd}$ Ed.) J. Stenesh (Ed.), Wiley-Interscience (1989); *Dictionary of Microbiology and Molecular Biology* (3$^{rd}$ Ed.), P. Singleton and D. Sainsbury (Eds.), Wiley-Interscience (2007); *Chambers Dictionary of Science and Technology* (2$^{nd}$ Ed.), P. Walker (Ed.), Chambers (2007); *Glossary of Genetics* (5$^{th}$ Ed.), R. Rieger et al. (Eds.), Springer-Verlag (1991); and *The HarperCollins Dictionary of Biology*, W. G. Hale and J. P. Margham, (Eds.), HarperCollins (1991).

Although any methods and compositions similar or equivalent to those described herein can be used in the practice or testing of the present disclosure, the preferred methods, and compositions are described herein. For purposes of the present disclosure, the following terms are defined below for sake of clarity and ease of reference:

In accordance with long standing patent law convention, the words "a" and "an," when used in this application, including the claims, denote "one or more."

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "carrier" is intended to include any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

As used herein, the term "DNA segment" refers to a DNA molecule that has been isolated free of total genomic DNA of a particular species. Therefore, a DNA segment obtained from a biological sample using one of the compositions disclosed herein refers to one or more DNA segments that have been isolated away from, or purified free from, total genomic DNA of the particular species from which they are obtained. Included within the term "DNA segment," are DNA segments and smaller fragments of such segments, as well as recombinant vectors, including, for example, plasmids, cosmids, phage, viruses, and the like.

The terms "an effective amount" of an active agent refers to the amount of the active agent sufficient to elicit a desired biological response. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses. For example, an effective amount may be an amount sufficient to achieve one or more of the following: (i) prevent drusen formation; (ii) cause a reduction in drusen number and/or size (drusen regression); (iii) cause a reduction in or prevent lipofuscin deposits; (iv) prevent visual loss or slow the rate of visual loss; (v) prevent or slow the rate of choroidal neovascularization; (vi) cause a reduction in size and/or number of lesions characterized by choroidal neovascularization; (vii) improve visual acuity and/or contrast sensitivity; (viii) prevent or reduce the rate of photoreceptor or RPE cell atrophy or apoptosis; (ix) prevent or slow progression from the wet to the dry form of AMD.

As used herein, the terms "engineered" and "recombinant" cells are intended to refer to a cell into which an exogenous polynucleotide segment (such as DNA segment that leads to the transcription of a biologically active molecule) has been introduced. Therefore, engineered cells are distinguishable from naturally occurring cells, which do not contain a recombinantly introduced exogenous DNA segment. Engineered cells are, therefore, cells that comprise at least one or more heterologous polynucleotide segments introduced through the hand of man.

As used herein, the term "epitope" refers to that portion of a given immunogenic substance that is the target of (i.e., is bound by), an antibody or cell-surface receptor of a host immune system that has mounted an immune response to the given immunogenic substance as determined by any method known in the art. Further, an epitope may be defined as a portion of an immunogenic substance that elicits an antibody response or induces a T-cell response in an animal, as determined by any method available in the art (see, e.g., Geysen et al., 1984). An epitope can be a portion of any immunogenic substance, such as a protein, polynucleotide, polysaccharide, an organic or inorganic chemical, or any combination thereof. The term "epitope" may also be used interchangeably with "antigenic determinant" or "antigenic determinant site."

The term "for example" or "e.g.," as used herein, is used merely by way of example, without limitation intended, and should not be construed as referring only those items explicitly enumerated in the specification.

As used herein, "heterologous" is defined in relation to a predetermined referenced DNA or amino acid sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment is defined as a gene or segment that does not naturally occur adjacent to the referenced promoter and/or enhancer elements.

As used herein, "homologous" means, when referring to polypeptides or polynucleotides, sequences that have the same essential structure, despite arising from different origins. Typically, homologous proteins are derived from closely related genetic sequences, or genes. By contrast, an "analogous" polypeptide is one that shares the same function with a polypeptide from a different species or organism, but has a significantly different form to accomplish that function. Analogous proteins typically derive from genes that are not closely related.

As used herein, the term "homology" refers to a degree of complementarity between two polynucleotide or polypeptide sequences. The word "identity" may substitute for the word "homology" when a first nucleic acid or amino acid sequence has the exact same primary sequence as a second nucleic acid or amino acid sequence. Sequence homology and sequence identity can be determined by analyzing two or more sequences using algorithms and computer programs known in the art. Such methods may be used to assess whether a given sequence is identical or homologous to another selected sequence.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

As used herein, the phrase "in need of treatment" refers to a judgment made by a caregiver such as a physician or veterinarian that a patient requires (or will benefit in one or more ways) from treatment. Such judgment may made based on a variety of factors that are in the realm of a caregiver's expertise, and may include the knowledge that the patient is ill as the result of a disease state that is treatable by one or more compound or pharmaceutical compositions such as those set forth herein.

The phrases "isolated" or "biologically pure" refer to material that is substantially, or essentially, free from components that normally accompany the material as it is found in its native state. Thus, isolated polynucleotides in accordance with the invention preferably do not contain materials normally associated with those polynucleotides in their natural, or in situ, environment.

As used herein, the term "kit" may be used to describe variations of the portable, self-contained enclosure that includes at least one set of reagents, components, or pharmaceutically-formulated compositions to conduct one or more of the assay methods of the present disclosure. Optionally, such kit may include one or more sets of instructions for use of the enclosed reagents, such as, for example, in a laboratory or clinical application.

"Link" or "join" refers to any method known in the art for functionally connecting one or more proteins, peptides, nucleic acids, or polynucleotides, including, without limitation, recombinant fusion, covalent bonding, disulfide bonding, ionic bonding, hydrogen bonding, electrostatic bonding, and the like.

The terms "local administration" or "local delivery," in reference to delivery of a composition, formulation, or device of the invention, refer to delivery that does not rely upon transport of the agent to its intended target tissue via the vascular or lymphatic system from a site of administration that is remote from the intended target tissue. The agent is delivered directly to its intended target tissue or in the vicinity thereof, e.g. by injection or implantation. It will be appreciated that a small amount of the delivered agent may enter the vascular system and may ultimately reach the target tissue via the vascular system.

"Macular degeneration related condition" refers to any of a number of disorders and conditions in which the macula degenerates or loses functional activity. The degeneration or loss of functional activity can arise due to, for example, cell death, decreased cell proliferation, loss of normal biological function, or a combination of one or more of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. AMD is the major macular degeneration related condition, but a number of others are known including, but not limited to, Best macular dystrophy, Sorsby fundus dystrophy, Mallatia Leventinese and Doyne honeycomb retinal dystrophy, and related disorders of the mammalian eye.

As used herein, "mammal" refers to the class of warm-blooded vertebrate animals that have, in the female, milk-secreting organs for feeding the young. Mammals include without limitation humans, apes, many four-legged animals, whales, dolphins, and bats. A human is a preferred mammal for purposes of the invention.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by the hand of man in a laboratory is naturally-occurring. As used herein, laboratory strains of rodents that may have been selectively bred according to classical genetics are considered naturally occurring animals.

As used herein, the term "nucleic acid" includes one or more types of: polydeoxyribonucleotides (containing 2-deoxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (snRNA), small nucleolar RNA (snORNA), small nuclear RNA (snRNA), and small temporal RNA (stRNA), and the like, and any combination thereof.

"Ocular device" refers to a drug delivery device that has appropriate structure, dimensions, shape, and/or configuration and is made of appropriate materials so that it may be placed in or on the surface of the eye without causing unacceptable interference with the physiology or functioning of the eye. Preferably, placement of an ocular device does not significantly disrupt vision. An ocular device is typically a solid or semi-solid article of manufacture and is typically macroscopic, i.e., visible with the naked eye.

"Ocular neovascularization" (ONV) is used herein to refer to choroidal neovascularization or retinal neovascularization, or both.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "patient" (also interchangeably referred to as "host" or "subject"), refers to any host that can serve as a recipient of one or more of the therapeutic or diagnostic formulations as discussed herein. In certain aspects, the patient is a vertebrate animal, which is intended to denote any animal species (and preferably, a mammalian species such as a human being). In certain embodiments, a patient may be any animal host, including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, or any animal under the care of a veterinary or animal medical care practitioner.

The phrase "pharmaceutically acceptable" refers to molecular entities and compositions that preferably do not produce an allergic or similar untoward reaction when administered to a mammal, and in particular, when administered to a human. As used herein, "pharmaceutically acceptable salt" refers to a salt that preferably retains the desired biological activity of the parent compound and does not impart any undesired toxicological effects. Examples of such salts include, without limitation, acid addition salts formed with inorganic acids (e.g., hydrochloric acid, hydrobromic acid, sulfuric acid, phosphoric acid, nitric acid, and the like); and salts formed with organic acids including, without limitation, acetic acid, oxalic acid, tartaric acid, succinic acid, maleic acid, fumaric acid, gluconic acid, citric acid, malic acid, ascorbic acid, benzoic acid, tannic acid, pamoic (embonic) acid, alginic acid, naphthoic acid, polyglutamic acid, naphthalenesulfonic acids, naphthalenedisulfonic acids, polygalacturonic acid; salts with polyvalent metal cations such as zinc, calcium, bismuth, barium, magnesium, aluminum, copper, cobalt, nickel, cadmium, and the like; salts formed with an organic cation formed from N,N' dibenzylethylenediamine or ethylenediamine; and combinations thereof.

The term "pharmaceutically acceptable salt" as used herein refers to a compound of the present disclosure derived from pharmaceutically acceptable bases, inorganic or organic acids. Examples of suitable acids include, but are not limited to, hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, formic, benzoic, malonic, naphthalene-2-sulfonic, trifluoroacetic and benzenesulfonic acids. Salts derived from appropriate bases include, but are not limited to, alkali such as sodium and ammonia.

As used herein, the term "plasmid" or "vector" refers to a genetic construct that is composed of genetic material (i.e., nucleic acids). Typically, a plasmid or a vector contains an origin of replication that is functional in bacterial host cells, e.g., *Escherichia coli*, and selectable markers for detecting bacterial host cells including the plasmid. Plasmids and vectors of the present disclosure may include one or more genetic elements as described herein arranged such that an inserted coding sequence can be transcribed and translated in a suitable expression cells. In addition, the plasmid or vector may include one or more nucleic acid segments, genes, promoters, enhancers, activators, multiple cloning regions, or any combination thereof, including segments that are obtained from or derived from one or more natural and/or artificial sources.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

As used herein, the terms "prevent," "preventing," "prevention," "suppress," "suppressing," and "suppression" as used herein refer to administering a compound either alone or as contained in a pharmaceutical composition prior to the onset of clinical symptoms of a disease state so as to prevent any symptom, aspect or characteristic of the disease state. Such preventing and suppressing need not be absolute to be deemed medically useful.

The term "promoter," as used herein refers to a region or regions of a nucleic acid sequence that regulates transcription.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to any amino acid chain length, including those of short peptides from about two to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules including at least one amino acid polymer. Polypeptides and proteins of the present disclosure also include polypeptides and proteins that are or have been post-translationally modified, and include any sugar or other derivative(s) or conjugate(s) added to the backbone amino acid chain.

"Purified," as used herein, means separated from many other compounds or entities. A compound or entity may be partially purified, substantially purified, or pure. A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found, e.g., cellular material such as cellular proteins and/or nucleic acids.

A compound or entity is considered pure when it is removed from substantially all other compounds or entities, i.e., is preferably at least about 90%, more preferably at least about 91%, 92%, 93%, 94%, 95%, 96%, 97%, 98%, 99%, or greater than 99% pure. A partially or substantially purified compound or entity may be removed from at least 50%, at least 60%, at least 70%, or at least 80% of the material with which it is naturally found (e.g., cellular material such as cellular proteins, peptides, nucleic acids, etc.).

The term "recombinant" indicates that the material (e.g., a polynucleotide or a polypeptide) has been artificially or synthetically (non-naturally) altered by human intervention. The alteration can be performed on the material within or removed from, its natural environment, or native state. Specifically, e.g., a promoter sequence is "recombinant" when it is produced by the expression of a nucleic acid segment engineered by the hand of man. For example, a "recombinant nucleic acid" is one that is made by recombining nucleic acids, e.g., during cloning, DNA shuffling or other procedures, or by chemical or other mutagenesis; a "recombinant polypeptide" or "recombinant protein" is a polypeptide or protein which is produced by expression of a recombinant nucleic acid; and a "recombinant virus," e.g., a recombinant AAV virus, is produced by the expression of a recombinant nucleic acid.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "RNA segment" refers to an RNA molecule that has been isolated free of total cellular RNA of a particular species. Therefore, RNA segments can refer to one or more RNA segments (either of native or synthetic origin) that have been isolated away from, or purified free from, other RNAs. Included within the term "RNA segment," are RNA segments and smaller fragments of such segments.

"Retinal neovascularization" (RNV) refers to the abnormal development, proliferation, and/or growth of retinal blood vessels, e.g., on the retinal surface.

The term "sequence," when referring to amino acids, relates to all or a portion of the linear N-terminal-to-C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5'-to-3' order of nucleotides.

The phrase a "sequence essentially as set forth in SEQ ID NO:X" means that the sequence substantially corresponds to a portion of SEQ ID NO:X and has relatively few nucleotides (or amino acids in the case of polypeptide sequences) that are not identical to, or a biologically functional equivalent of, the nucleotides (or amino acids) of SEQ ID NO:X.

The term "biologically functional equivalent" is well understood in the art, and is further defined in detail herein. Accordingly, sequences that have about 85% to about 90%; or more preferably, about 91% to about 95%; or even more preferably, about 96% to about 99%; of nucleotides that are identical or functionally equivalent to one or more of the nucleotide sequences provided herein are particularly contemplated to be useful in the practice of the invention.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of skill in the art, such as e.g., the FASTA program analysis described by Pearson and Lipman (1988).

"Sequential administration" of two or more agents refers to administration of two or more agents to a subject such that the agents are not present together in the subject's body at greater than de minimis concentrations. Administration of the agents may, but need not, alternate. Each agent may be administered multiple times.

"Significant sequence homology" as applied to an amino acid sequence means that the sequence displays at least approximately 20% identical or conservatively replaced amino acids, preferably at least approximately 30%, at least approximately 40%, at least approximately 50%, at least approximately 60% identical or conservatively replaced amino acids, desirably at least approximately 70% identical or conservatively replaced amino acids, more desirably at least approximately 80% identical or conservatively replaced amino acids, and most desirably at least approximately 90% amino acid identical or conservatively replaced amino acids relative to a reference sequence. When two or more sequences are compared, any of them may be considered the reference sequence. % identity can be calculated using a FASTA or BLASTP algorithm, using default parameters. A PAM250 or BLOSUM62 matrix may be used. For purposes of calculating % identical or conservatively replaced residues, a conservatively replaced residue is considered identical to the residue it replaces. Conservative replacements may be defined in accordance with Stryer, L, *Biochemistry*, 3rd ed., 1988, according to which amino acids in the following groups possess similar features with respect to side chain properties such as charge, hydrophobicity, aromaticity, etc. (1) Aliphatic side chains: G, A, V, L, I; (2) Aromatic side chains: F, Y, W; (3) Sulfur-containing side chains: C, M; (4) Aliphatic hydroxyl side chains: S, T; (5) Basic side chains: K, R, H; (6) Acidic amino acids: D, E, N, Q; and (7) Cyclic aliphatic side chain: P.

The term "subject," as used herein, describes an organism, including mammals such as primates, to which treatment with the compositions according to the present disclosure can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

"Substantial sequence homology" as applied to a sequence means that the sequence displays at least approximately 60% identity, desirably at least approximately 70% identity, more desirably at least approximately 80% identity, and most desirably at least approximately 90% identity relative to a reference sequence. When two or more sequences are compared, any of them may be considered the reference sequence. % identity can be calculated using a FASTA, BLASTN, or BLASTP algorithm, depending on whether amino acid or nucleotide sequences are being compared. Default parameters may be used, and in exemplary embodiments, a PAM250 and/or BLOSUM62 matrix or such like may be employed in the practice of the invention.

A "sustained release formulation" is a composition of matter that comprises a therapeutic agent as one of its components and further comprises one or more additional components, elements, or structures effective to provide sustained release of the therapeutic agent, optionally in part because of the physical structure of the formulation. Sustained release is release or delivery that occurs either continuously or intermittently over an extended period, e.g., at least several days, at least several weeks, at least several months, at least several years, or even longer, depending upon the particular formulation employed.

"Suitable standard hybridization conditions" for the present disclosure include, for example, hybridization in 50% formamide, 5×Denhardt's solution, 5×SSC, 25 mM sodium phosphate, 0.1% SDS and 100 µg/ml of denatured salmon sperm DNA at 42° C. for 16 hr followed by 1 hr sequential washes with 0.1×SSC, 0.1% SDS solution at 60° C. to remove the desired amount of background signal. Lower stringency hybridization conditions for the present disclosure include, for example, hybridization in 35% formamide, 5×Denhardt's solution, 5×SSC, 25 mM sodium phosphate, 0.1% SDS and 100 µg/ml denatured salmon sperm DNA or *E. coli* DNA at 42° C. for 16 h followed by sequential washes with 0.8×SSC, 0.1% SDS at 55° C. Those of skill in the art will recognize that conditions can be readily adjusted to obtain the desired level of stringency.

As used herein, the term "structural gene" is intended to generally describe a polynucleotide, such as a gene, that is expressed to produce an encoded peptide, polypeptide, protein, ribozyme, catalytic RNA molecule, or antisense molecule.

Naturally, the present disclosure also encompasses nucleic acid segments that are complementary, essentially complementary, and/or substantially complementary to at least one or more of the specific nucleotide sequences specifically set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the specific nucleic acid segments disclosed herein under relatively stringent conditions such as those described immediately above.

As described above, the probes and primers of the present disclosure may be of any length. By assigning numeric values to a sequence, for example, the first residue is 1, the second residue is 2, etc., an algorithm defining all probes or primers contained within a given sequence can be proposed:

n to n+y, where n is an integer from 1 to the last number of the sequence, and y is the length of the probe or primer minus one, where n+y does not exceed the last number of the sequence.

Thus, for a 25-basepair probe or primer (i.e., a "25 mer"), the collection of probes or primers correspond to bases 1 to 25, bases 2 to 26, bases 3 to 27, bases 4 to 28, and so on over the entire length of the sequence. Similarly, for a 35-basepair probe or primer (i.e., a "35-mer"), exemplary primer or probe sequence include, without limitation, sequences corresponding to bases 1 to 35, bases 2 to 36, bases 3 to 37, bases 4 to 38, and so on over the entire length of the sequence. Likewise, for 40-mers, such probes or primers may correspond to the nucleotides from the first basepair to by 40, from the second by of the sequence to by 41, from the third by to by 42, and so forth, while for 50-mers, such probes or primers may correspond to a nucleotide sequence extending from by 1 to by 50, from by 2 to by 51, from by 3 to by 52, from by 4 to by 53, and so forth.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the mRNA "target" sequence, and will have no more than about 1, about 2, about 3, about 4, about 5, about 6, about 7, about 8, about 9, or about 10 or so base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary sequences will typically bind quite specifically to the target sequence region of the mRNA and will therefore be highly efficient in reducing, and/or even inhibiting the translation of the target mRNA sequence into polypeptide product.

Substantially complementary nucleic acid sequences will preferably be greater than about 80 percent complementary (or "% exact-match") to a corresponding nucleic acid target sequence to which the nucleic acid specifically binds, and will, more preferably be greater than about 85 percent complementary to the corresponding target sequence to which the nucleic acid specifically binds. In certain aspects, as described above, it will be desirable to have even more substantially complementary nucleic acid sequences for use in the practice of the invention, and in such instances, the nucleic acid sequences will be greater than about 90 percent complementary to the corresponding target sequence to which the nucleic acid specifically binds, and may in certain embodiments be greater than about 95 percent complementary to the corresponding target sequence to which the nucleic acid specifically binds, and even up to and including about 96%, about 97%, about 98%, about 99%, and even about 100% exact match complementary to all or a portion of the target sequence to which the designed nucleic acid specifically binds.

Percent similarity or percent complementary of any of the disclosed nucleic acid or polypeptide sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov and Burgess (1986), (2) a penalty of 3.0 for each gap and an additional 0.10 penalty for each symbol in each gap; and (3) no penalty for end gaps.

The term "therapeutically practical time period" means a time necessary for an active agent to be therapeutically effective. The term "therapeutically-effective" refers to a reduction in the severity and/or frequency of one or more symptoms, an elimination of symptoms, and/or one or more underlying causes, the prevention of an occurrence of one or more symptoms and/or their underlying cause, and/or an improvement or a remediation of damage.

A "therapeutic agent" may be any physiologically or pharmacologically active substance that may produce a desired biological effect in a targeted site in a subject. The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally-occurring, or produced by synthetic or recombinant methods, or any combination thereof. Drugs that are affected by classical multidrug resistance, such as the vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent. Cytokines may be also used as the therapeutic agent. Examples of such cytokines are lymphokines, monokines, and traditional polypeptide hormones. A cancer chemotherapy agent may be a preferred therapeutic agent. For a more detailed description of anticancer agents and other therapeutic agents, those skilled in the art are referred to any number of instructive manuals including, but not limited to, the *Physician's Desk Reference* and to Goodman and Gilman's "*Pharmacological Basis of Therapeutics*" tenth edition, Hardman et al. (Eds.) (2001).

"Transcriptional regulatory element" refers to a polynucleotide sequence that activates transcription alone or in combination with one or more other nucleic acid sequences. A transcriptional regulatory element can, for example, comprise one or more promoters, one or more response elements, one or more negative regulatory elements, and/or one or more enhancers.

As used herein, a "transcription factor recognition site" and a "transcription factor binding site" refer to a polynucleotide sequence(s) or sequence motif(s), which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted based on known consensus sequence motifs, or by other methods known to those of ordinary skill in the art.

"Transcriptional unit" refers to a polynucleotide sequence that comprises at least a first structural gene operably linked to at least a first cis-acting promoter sequence and optionally linked operably to one or more other cis-acting nucleic acid sequences necessary for efficient transcription of the structural gene sequences, and at least a first distal regulatory element as may be required for the appropriate tissue-specific and developmental transcription of the structural gene sequence operably positioned under the control of the promoter and/or enhancer elements, as well as any additional cis sequences that are necessary for efficient transcription and translation (e.g., polyadenylation site(s), mRNA stability controlling sequence(s), etc. As used herein, the term "transformed cell" is intended to mean a host cell whose nucleic acid complement has been altered by the introduction of one or more exogenous polynucleotides into that cell.

As used herein, the term "transformation" is intended to generally describe a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

"Treating" or "treatment of" as used herein, refers to providing any type of medical or surgical management to a subject. Treating can include, but is not limited to, administering a composition comprising a therapeutic agent to a subject. "Treating" includes any administration or application of a compound or composition of the invention to a subject for purposes such as curing, reversing, alleviating, reducing the severity of, inhibiting the progression of, or reducing the likelihood of a disease, disorder, or condition or one or more symptoms or manifestations of a disease, disorder, or condition. A composition of this invention can be administered to a subject who has developed a macular degeneration related condition risk of developing an infection relative to a member of the general population. A composition of this invention can be administered to a subject who has developed an eye disorder such as exudative or non-exudative AMD, diabetic retinopathy, uveitis, Bechet's disease, a localized or a generalized inflammation, or such like, or to a subject that is at increased risk of developing such a disorder (as compared to a member of the general population). In certain aspects, the inventors contemplate that the compositions of the present disclosure may also be administered prophylactically, i.e., before development of any symptom or manifestation of the condition, where such prophylaxis is warranted. Typically, in such cases, the subject will be one that has been diagnosed for being "at risk" of developing such a disease or disorder, either as a result of familial history, medical record, or the completion of one or more diagnostic or prognostic tests indicative of a propensity for subsequently developing such a disease or disorder.

The term "vector," as used herein, refers to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

In certain embodiments, it will be advantageous to employ one or more nucleic acid segments of the present disclosure in combination with an appropriate detectable marker (i.e., a "label,"), such as in the case of employing labeled polynucleotide probes in determining the presence of a given target sequence in a hybridization assay. A wide variety of appropriate indicator compounds and compositions are known in the art for labeling oligonucleotide probes, including, without limitation, fluorescent, radioactive, enzymatic or other ligands, such as avidin/biotin, etc., which are capable of being detected in a suitable assay. In particular embodiments, one may also employ one or more fluorescent labels or an enzyme tag such as urease, alkaline phosphatase or peroxidase, instead of radioactive or other environmentally less-desirable reagents. In the case of enzyme tags, colorimetric, chromogenic, or fluorigenic indicator substrates are known that can be employed to provide a method for detecting the sample that is visible to the human eye, or by analytical methods such as scintigraphy, fluorimetry, spectrophotometry, and the like, to identify specific hybridization with samples containing one or more complementary or substantially complementary nucleic acid sequences. In the case of so-called "multiplexing" assays, where two or more labeled probes are detected either simultaneously or sequentially, it may be desirable to label a first oligonucleotide probe with a first label having a first detection property or parameter (for example, an emission and/or excitation spectral maximum), which also labeled a second oligonucleotide probe with a second label having a second detection property or parameter that is different (i.e., discreet or discernible from the first label. The use of multiplexing assays, particularly in the context of genetic amplification/detection protocols are well-known to those of ordinary skill in the molecular genetic arts.

The section headings used throughout are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 rAAV Vector Constructs

The present example describes the construction of a novel recombinant variant of M013 that is engineered by fusion to a protein transduction domain peptide sequence (in this case, a specific protein domain of the tat protein from HIV has been used). This protein is expressed as a secreted fusion tatM013 protein from a recombinant AAV vector that can deliver the modified tatM013 gene into target tissues in order to inhibit inflammation locally within the transduced tissue. Thus, the therapeutic tatM013 fusion protein inhibits inflammatory signals not only from cells that have taken up the AAV-tatM013 virus vector (and thus express the therapeutic tatM013 protein directly), but also in neighboring cells that take up the secreted version of the expressed tatM013 protein itself. This "dual inhibition" then broadly inhibits multiple key pro-inflammatory pathways within various classes of cells within the AAV vector-transduced tissue, and this suppression will last as long as the AAV-M013 vector is active and expresses the therapeutic tatM013 fusion protein. The inflamed tissue highlighted in this application is designed to mimic various inflammatory diseases of the eye, but it is contemplated that similar anti-inflammatory effects may be forced in other tissues that are suitable for similar AAV-based gene delivery treatment regimens.

A variety of factors including oxidative stress, inflammation with a possible autoimmune component, genetic background (e.g., mutations), and environmental or behavioral features such as smoking and diet may contribute to the pathogenesis of AMD in manners that are as yet poorly understood (Zarbin, 2004). Regardless of the underlying etiology, the clinical hallmark of AMD is the appearance of drusen, localized deposits of lipoproteinaceous material that accumulate in the space between the RPE and Bruch's membrane, which separates the RPE from the choroidal vessels (choriocapillaris). Drusen are typically the earliest clinical finding in AMD. The existence of macular drusen is a strong risk factor for the development of both wet and dry forms of AMD (Ambati et al., 2003).

Ocular inflammation can affect a large number of eye structures including the conjunctiva, cornea, episclera, sclera, uveal tract, retina, vasculature, optic nerve, and orbit. Evidence of ocular inflammation can include the presence of inflammation-associated cells such as white blood cells (e.g., neutrophils, macrophages) in the eye, the presence of endogenous inflammatory mediators known in the art, one or more symptoms such as eye pain, redness, light sensitivity, blurred vision and floaters, etc. Uveitis is a general term that refers to inflammation in the uvea of the eye, e.g., in any of the structures of the uvea, including the iris, ciliary body or choroid. Specific types of uveitis include iritis, iridocyclitis, cyclitis, pars planitis, and choroiditis. Uveitis can arise from a number of different causes and is associated with a number of different diseases, including, but not limited to, rheumatic diseases such as rheumatic diseases (e.g., ankylosing spondylitis and juvenile rheumatoid arthritis), certain infectious diseases such as tuberculosis and syphilis, other conditions such as sarcoidosis, systemic lupus erythematosus, chemical injury, trauma, surgery, etc. Keratis refers to inflammation of the cornea. Keratitis has a diverse array of causes including bacterial, viral, or fungal infection, trauma, and allergic reaction. Amoebic infection of the cornea, e.g., caused by *Acanthamoeba*, is a particular problem for contact lens wearers. Scleritis refers to inflammation of the sclera. Uveitis, keratitis, and scleritis, and methods for their diagnosis are well known in the art. Symptoms of the various inflammatory conditions that affect the eye can include, but are not limited to, eye pain, redness, light sensitivity, tearing, blurred vision, floaters, swelling, discomfort, or a combination of such symptoms. Ocular inflammation of various types is known to occur in association with a variety of local or systemic diseases, some of which are noted above. In some instances, however, the cause of the inflammation may remain unknown.

Materials and Methods:

The myxoma virus M013 coding sequence was fused to the cell-penetrating peptide sequence derived from the HIV Tat protein using PCR, and called tatM013. The chimeric product was then fused either to a puromycin-resistance gene in a lentiviral vector plasmid, or to a secretable form of GFP through a furin cleavage site. The sequence of the TatM013 insert was verified by DNA sequencing and cloned in an AAV plasmid. The monocytic cell line THP-1 and the retina pigmented epithelium like cell line, ARPE-19, were transduced with lentiviral vectors to generate stable cell lines by selecting for puromycin resistant cells. The expression of the recombinant TatM013 protein was verified by western blotting, and the biological effects of this expressed protein on LPS- or 4-HNE-induced secretion of IL-1β were measured by ELISA. The cellular localization of the secretable TatM013 protein was determined by fluorescent microscopy. Detection of secreted TatM013 protein was inferred by western blotting using cell conditioned media. Transfer of biological activity was determined using the ARPE-19 and Raw 264.7 cells. The in vivo anti-inflammatory effects of the TatM013 protein expressed from an AAV vector were determined by using the endotoxin-induced uveitis (EIU) mouse model.

In these in vitro experiments, the conditioned media of three independent cultures were analyzed. Animal studies were conducted in accordance with the guidelines of the Institutional Animal Care and Use Committee (IACUC) of the University of Florida (Gainesville, Fla.). These studies were conducted with the minimal number of mice needed to investigate endpoints that could not be addressed with in vitro experiments. Animal were properly anesthetized with ketamine and xylazine for in-life assessment by funduscopy and humanely euthanized, via $CO_2$ inhalation, for the analysis of tissue.

Cell Culture.

Human HEK293T and mouse RAW 264.7 cell lines were grown in Dulbecco's modified Eagle's medium (DMEM) supplemented with 10% fetal bovine serum (FBS) and 1% penicillin—streptomycin (Pen-Strep) solution. The human ARPE-19 cell line was grown in DMEM/F12 (50/50) medium supplemented with 10% FBS and 1% Pen-Strep. The human THP-1 cell line was grown in RPMI 1640 medium supplemented with 10% FBS and 1% Pen-Strep. All the cell cultures were maintained in an incubator at 37° C. with 5% $CO_2$. All stable cell lines generated by lentiviral vector transduction were grown in the corresponding medium supplemented with puromycin at a dose of 1 μg/mL.

Concentration of Conditioned Medium.

Conditioned M199 low-protein medium (Invitrogen Life Technologies, Grand Island, N.Y., USA) was harvested and placed in a 15-mL conical tube and centrifuged at 2500×g for 5 min to remove any cellular debris. The conditioned medium was then passed through a 50-kDa molecular weight cut off (MWCO) Amicon-Ultra centrifugal filter (EMD Millipore, Billerica, Mass., USA) by centrifugation at 14,000×g for 15 min in a tabletop microcentrifuge. The flow-through was then harvested and passed through a 3-kDa Amicon-Ultra centrifugal filter (EMD Millipore) by centrifugation at 14,000×g for 30 min in a tabletop microcentrifuge. The concentrated medium containing molecules with molecular weights between 50 and 3 kDa was collected by inversion and centrifugation of the filter at 1000×g for 1 min.

Viral Vectors.

All the lentiviral vectors were created with the pCDH-EF1-MCS-T2A-Puro plasmid (Systems Biosciences, Mountain View, Calif., USA). The transgenes were cloned, using the EcoRI and the NotI restriction sites in the multiple cloning sites. Plasmids were propagated in DH5α cells and sequenced by the dideoxy-chain-termination method. To generate viral particles, the plasmids were cotransfected with the pPACKH1 lentiviral vector packaging kit (Systems Biosciences) in HEK293T cells. The lentiviral vector-containing media were harvested 48 hr after the cotransfection and were centrifuged at 2500×g for 5 min at 4° C. The vector-containing media were passed through a 0.22-μm (pore size) syringe filter.

The sGFP-TatM013 vector plasmid was created by subcloning the TatM013 fusion construct downstream of Igκ-GFP (IgG kappa light chain leader sequence fused to the GFP sequence) while maintaining the reading frame of these elements. This gene construct was then excised, using the XbaI (5') and XhoI (3') sites, and cloned in the pTR-smCBA AAV plasmid. The final pTR-smCBA-Igκ-GFP-TatM013 plasmid was grown in SURE 2 cells (Agilent, Santa Clara, Calif., USA) and purified by passage through a CsCl gradient. The DNA was packaged, purified, and titered by the Center for Vision Research Vector Core at the University of Florida according to previously published methods.

Isolation of Vitreous.

Mouse vitreous was isolated using a protocol developed by Skeie and colleagues. Briefly, mice were humanely killed, using $CO_2$. A transverse incision was made in the cornea with a surgical scalpel to allow the aqueous humor to flow. Excess aqueous humor was absorbed with a paper towel. The retina, vitreous, and lens were eviscerated by squeezing the eye from the back. Tissues were collected in a sterile 1.5-mL tube and later transferred into an Amicon Ultra centrifugal filter (cutoff, 50 kDa; EMD Millipore). An additional 100 µL of phosphate-buffered saline (PBS) supplemented with protease inhibitor cocktail (Thermo Fisher Scientific, Rockford, Ill., USA) was added to the tube. Samples were centrifuged at 14,000×g for 15 min, and vitreous flow-through was collected. Protein concentration of the vitreous was determined by DC protein assay (Bio-Rad, Hercules, Calif., USA) according to the manufacturer's protocol and stored at −20° C. until assayed.

ELISA.

The ELISA kit for mouse IL-1β was purchased from Peprotech (Peprotech, Rocky Hill, N.J., USA). The concentration of IL-1β was determined according to the manufacturer's protocol. The concentration of human IL-1β was determined with a RayBiotech human IL-1β ELISA kit (RayBiotech, Norcross, Ga., USA) according to the manufacturer's protocol. In both cases, a total of 100 µL of either tissue homogenate or cell culture medium was analyzed.

Western Blots.

The cells corresponding to the conditioned media were lysed in NP-40 lysis buffer supplemented with protease inhibitor cocktail (Thermo Fisher Scientific) and 2 mM EDTA. The protein concentration of the samples was measured with the DC protein assay (Bio-Rad) according to the manufacturer's protocol. Protein lysates were diluted in Laemmli buffer containing 100 µM dithiothreitol (DTT) and boiled for 5 min. Equal amounts of protein were separated by sodium dodecyl sulfate (SDS)-polyacrylamide gel electrophoresis and transferred onto a polyvinylidene difluoride (PVDF) membrane, using an iBlot system (Invitrogen Life Technologies) as recommended by the manufacturer. This membrane was blocked with a proprietary blocking buffer from Li-Cor Biosciences (Lincoln, Nebr., USA) for 1 hr at room temperature and incubated overnight with the designated primary antibody at 4° C. The membrane was then washed four times with PBS-0.1% Tween 20 and incubated with the corresponding IRDye secondary antibody (1:5000 dilution in blocking buffer; Li-Cor Biosciences). Finally, the membrane was washed as done previously and scanned with an Odyssey infrared imaging system (Li-Cor Biosciences).

Endotoxin-Induced Uveitis Mouse Model.

Mice of the C57BL/6J strain were injected intravitreally with 3×10⁹ vector genomes in each eye. Two weeks after injection the mice were inspected by spectral domain optical coherence tomography, using a Bioptigen high-resolution instrument, to exclude inflammatory infiltrates resulting from injection of vector. One month after injection, green fluorescent protein (GFP) expression was observed by fluorescence funduscopy. The next day mice were injected intravitreally in each eye with 25 ng of lipopolysaccharide (LPS). After 24 hr, these mice were killed, and their eyes were enucleated and placed in 4% paraformaldehyde at 4° C. overnight. The eyes were placed in PBS after fixation and stored at 4° C. until embedding. Eyes were dehydrated and embedded in paraffin in preparation for sectioning. Embedded eyes were sectioned through the cornea-optic nerve axis, at a thickness of 12 µm. Eight step sections were collected in independent slides, with sections on the same slide having a difference of 80 µm. Slides were stained with hematoxylin and eosin to visualize infiltrating cells. These cells were quantified in images of the sections by an individual who was ignorant of the treatment group.

Funduscopy.

A Micron III digital fundus retinal imaging microscope (Phoenix Research Laboratories, Pleasanton, Calif., USA) was used to monitor GFP expression in life. Conscious mice had their eyes dilated with 1% atropine and 2.5% phenylephrine. Mice were then anesthetized with a mixture of ketamine and xylazine in normal saline (0.9% sodium chloride solution USP, pH 5.0; Baxter, Deerfield, Ill., USA). To avoid loss of moisture from the ocular surface during the procedure, mice received a drop of 2.5% hypromellose ophthalmic demulcent solution (Gonak; AKORN, Lake Forest, Ill., USA). Bright-field fundus images were acquired using the same exposure times. GFP fluorescence was measured with the fluorescence filter, using the same exposure times for all the eyes.

Statistical Analysis.

Data from in vitro experiments are reported as averages±standard deviation. Values were compared by analysis of variance followed by a Student Newman-Keuls t-test to determine significant differences between groups. For animal studies, values are reported as averages±standard-error-of-the-mean, and statistical comparison was done by Mann-Whitney U test to avoid potential biases introduced by outliers. P<0.05 was considered significant (*p≤0.05, p≤0.01, *p≤0.001).

Results and Discussion

AAV-Mediated Expression of Myxoma Virus Gene M013 can (FIG. 1D). Together, these results demonstrate that ectopic expression of M013 or TatM013 protein inhibited inflammasome-activated IL-1β secretion in vitro. Furthermore, this fusion of the M013 gene with the cell-penetrating peptide Tat did not seem to compromise the efficiency of this inhibitory function of M013.

Development of an AAV Vector that Expresses Secretable and Cell-Penetrating M013.

Figure 2A:
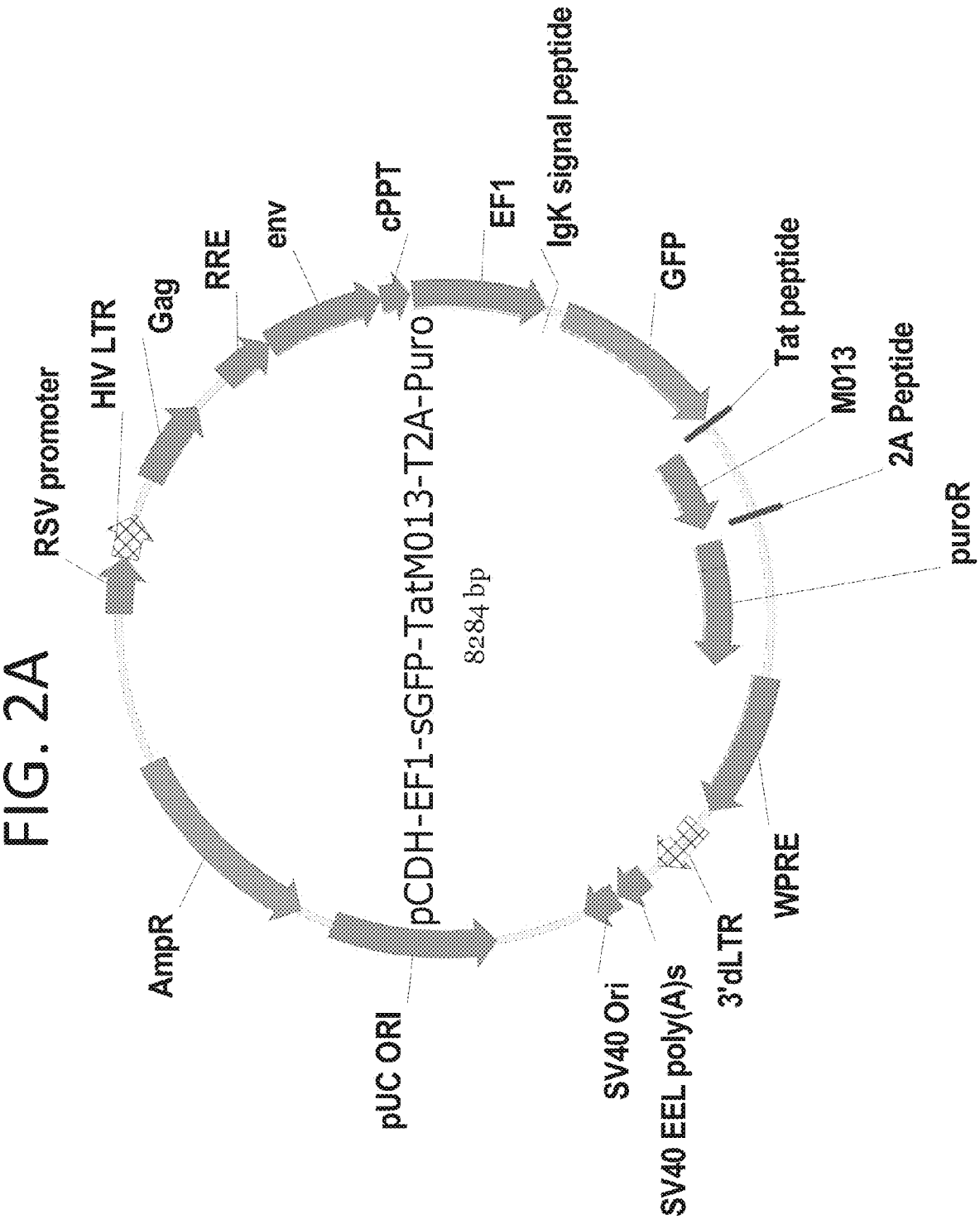
Figure 5A:
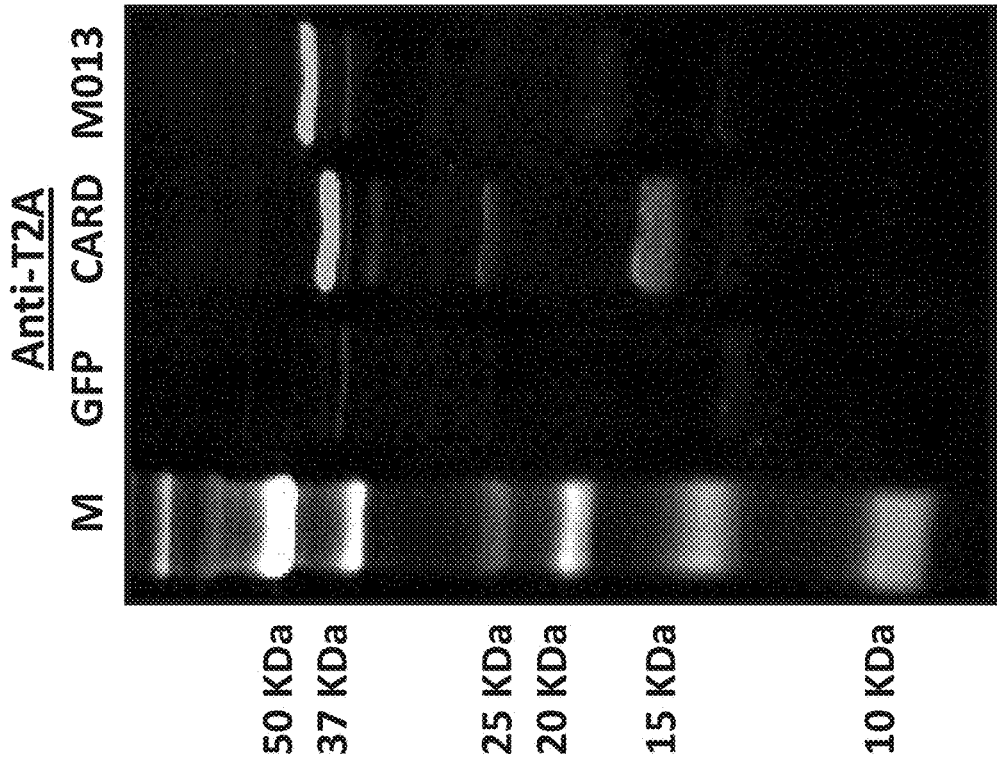
Figure 5B:
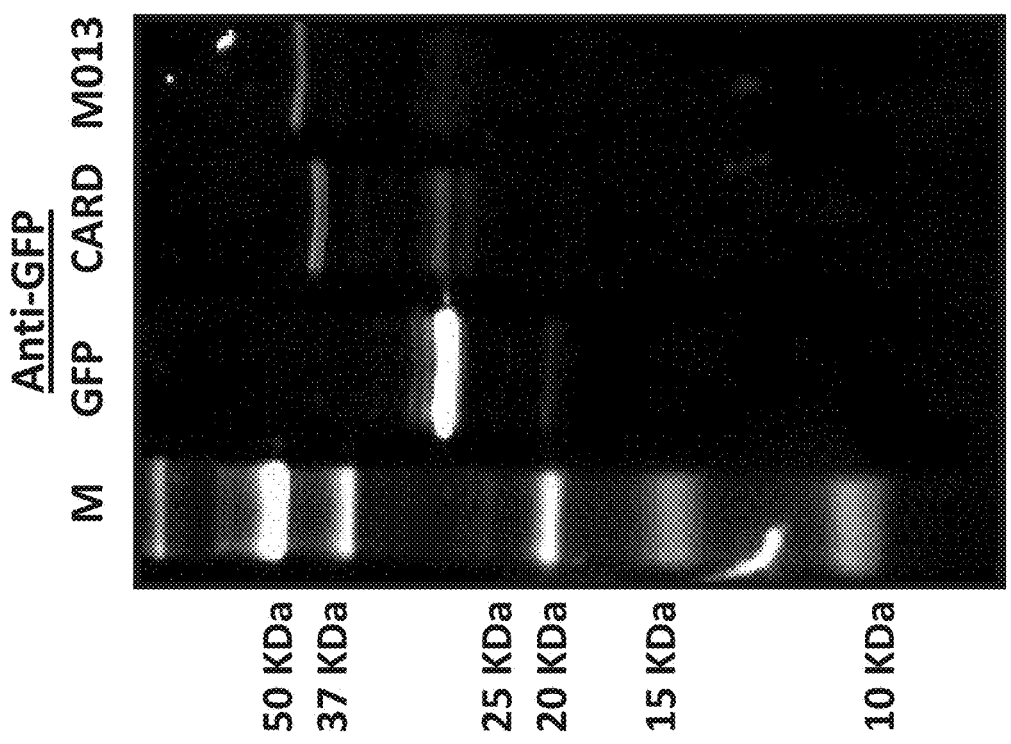

The various cellular sources of IL-1β in the eye make it difficult to prevent its secretion by a gene therapy strategy that blocks IL-1β secretion only from cells transduced with the AAV vector. To permit the visualization of TatM013 protein, which has the potential to impact surrounding cells that may not be directly transduced by the gene therapy vector, the TatM013 coding sequence was fused to a sequence encoding a secretable version of GFP. This fusion construct was expressed as a single recombinant protein containing the N-terminal secretory signal from the Igκ gene fused to GFP and linked at the C terminus to the TatM013 gene and separated by a furin cleavage site sequence (FIG. 2A). This secretion system has been demonstrated to deliver and secrete a small peptide derived from angiotensin (Verma et al., 2012). To study the expression of the novel sGFP-TatM013 fusion construct, it was cloned in a lentiviral plasmid under the control of the elongation factor (EF)-1α promoter and fused to the puromycin resistance (puroR) gene through a self-cleaving 2A peptide (FIG. 2A). Expression of the fused sGFP-TatM013 protein was demonstrated by Western blot, which revealed a band of the predicted size using either an antibody against the 2A peptide (not shown) or against GFP itself (FIG. 5A). By using fluorescence microscopy, it was observed that control GFP had a cytoplasmic distribution, whereas sGFP-TatM013 had a punctate pattern characteristic of proteins within the secretory pathway (Kakihana et al., 2013; Stow and Murray, 2013; Reinhardt et al., 2014) (FIG. 5B). This result suggested that the sGFP-TatM013 gene product could be expressed, and targeted for secretion.

Figure 2B:
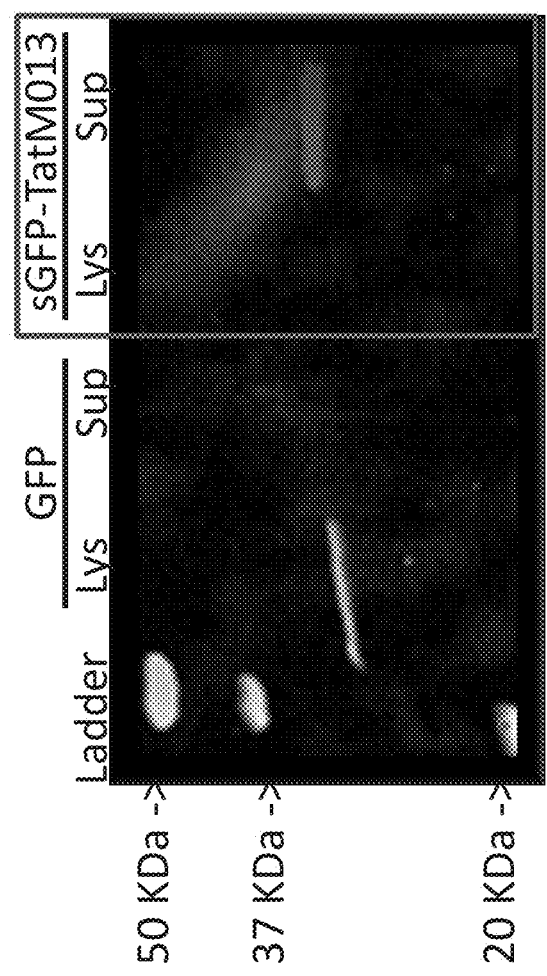
Figure 2C:
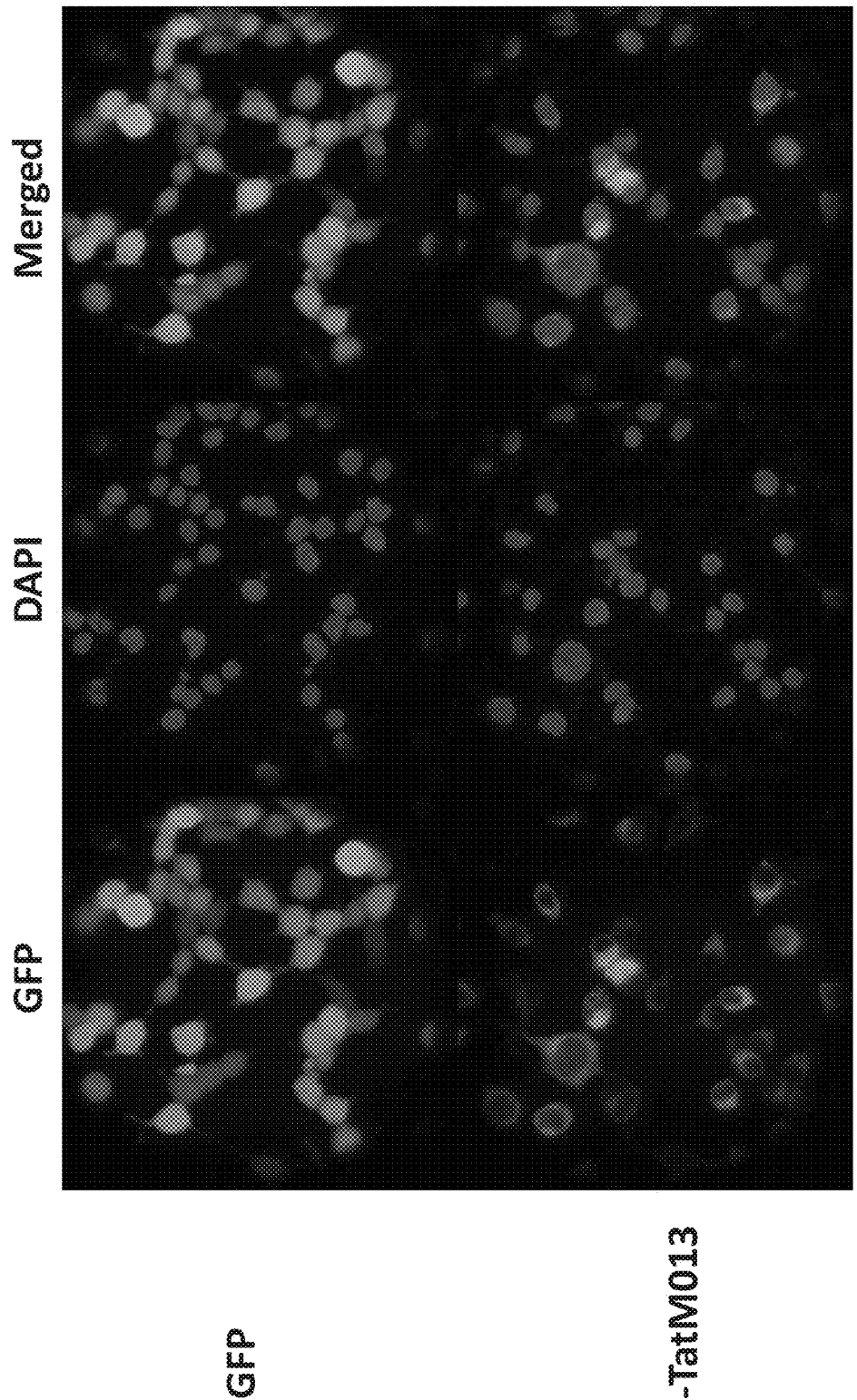
Figure 3A:
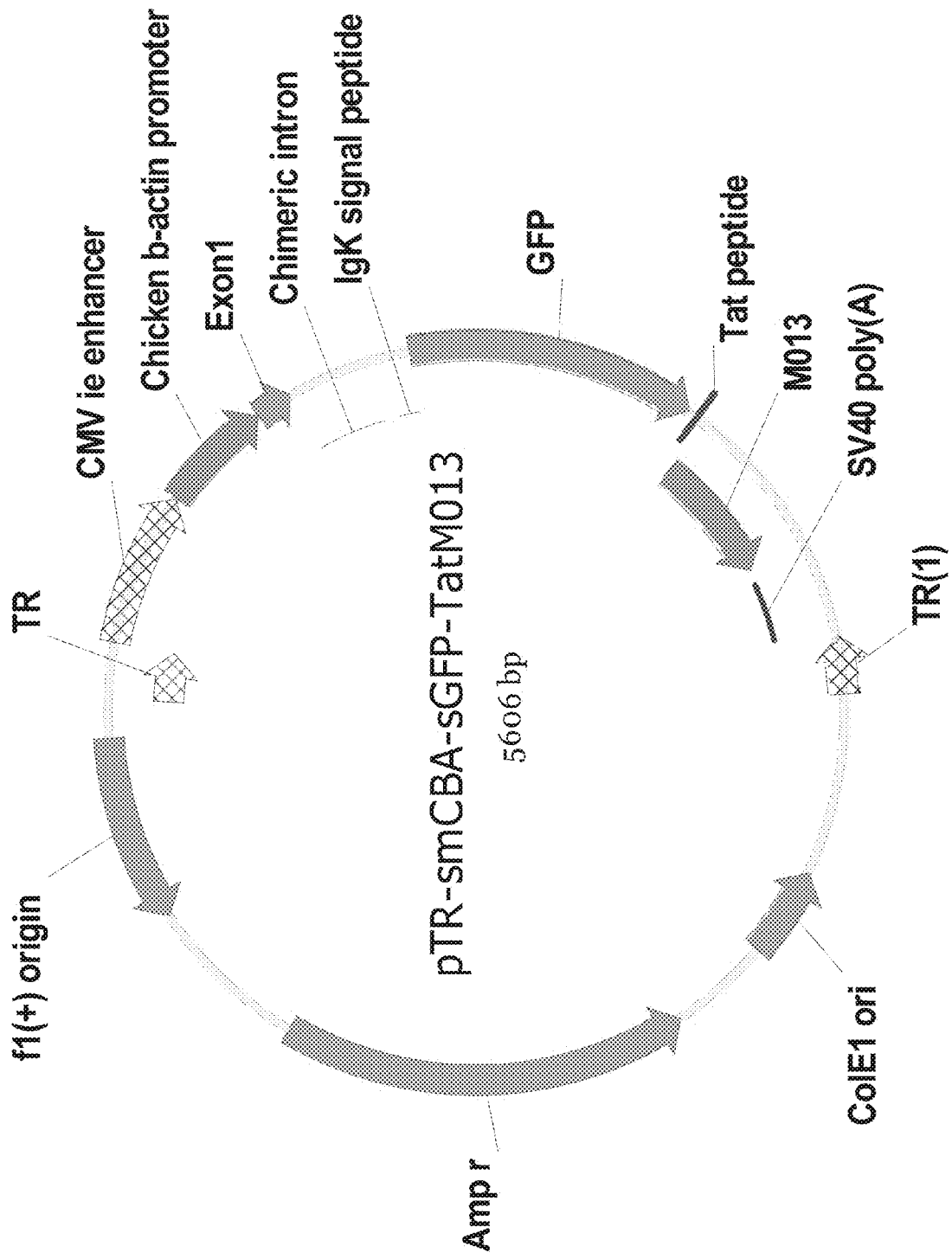
Figures 1, 3B:
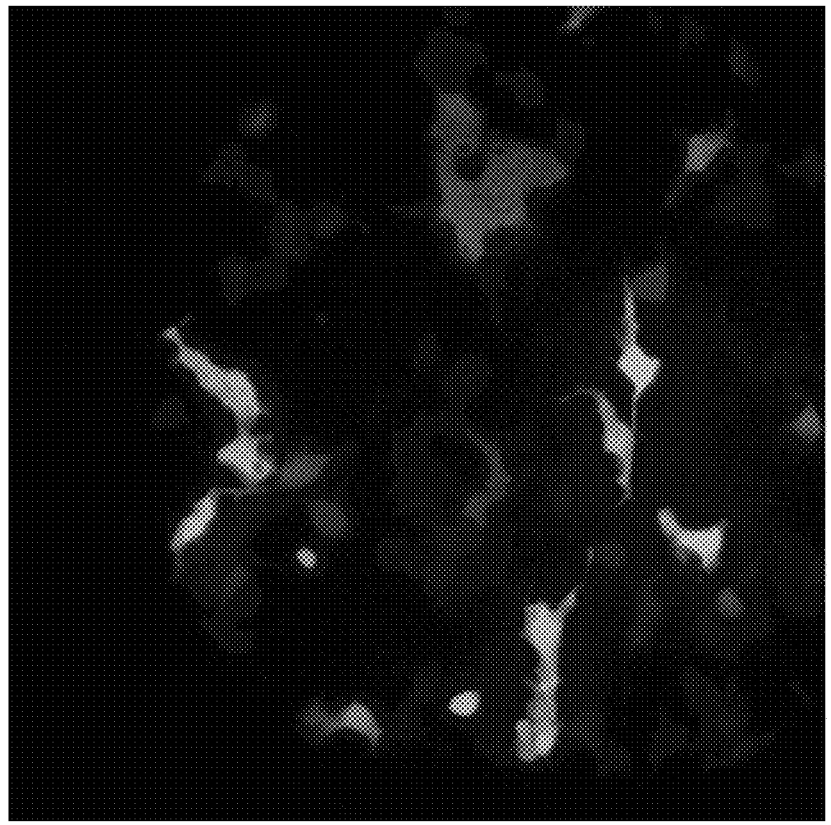

For stable delivery to the eye, an AAV vector was designed to express sGFP-TatM013. AAV has proven to be safe and effective in multiple clinical trials intended to treat retinal disease (Hauswirth et al., 2008; Maguire et al., 2008; Simonelli et al., 2010; Testa et al., 2013; MacLaren et al., 2014). This construct was subcloned in a plasmid containing the inverted terminal repeats (TRs) of AAV2 and a truncated chimeric cytomegalovirus (CMV) β-actin (smCBA) promoter, which is known to be ubiquitously active in the retina (Beltran et al., 2010) (FIG. 3A). HEK293T cells were transfected with the AAV plasmid delivering either control GFP or sGFP-TatM013 to determine the effect of the secretion signal on the distribution of the fused protein. By using fluorescence microscopy, a similar punctate pattern of distribution was observed for GFP only among cells transfected with sGFP-TatM013 (FIG. 3B-1). To demonstrate that the sGFP-TatM013 protein was proteolyzed by furin and secreted, conditioned media was harvested from cells transfected with either control GFP or sGFP-TatM013. Medium was concentrated and a portion of it was fractionated on an SDS-polyacrylamide gel. In a Western blot (FIG. 3B-2), GFP was detected in the conditioned medium of sGFP-TatM013-expressing cells and was absent in the conditioned medium of GFP-expressing cells, suggesting that secretion and proteolysis at the furin cleavage site of the fusion protein did occur. The biological activity of the extracellular proteolyzed TatM013 was demonstrated by its ability to inhibit inflammasome signaling in cells incubated with this conditioned medium. Incubation of cells with TatM013-conditioned medium caused a significant decrease in the amount of IL-1β produced by cells treated with an inflammatory agent (LPS or 4-HNE) when compared with cells that were incubated with control medium (FIG. 2B). Although IL-1β release was repressed by the TatM013 conditioned medium, no cell death was observed after exposure to any of the conditioned media. These results demonstrated that secretable and cell-penetrating TatM013 could be expressed by AAV and that this protein retained its anti-inflammasome activity when exported into the conditioned medium.

AAV Vector-Mediated Expression of sGFP-TatM013 Protein is Biologically Active.

With the goal of treating inflammatory retinal disease, delivery of therapeutic vector to the vitreous compartment of the eye may be clinically advantageous, because intravitreal injections are routinely performed in outpatient office visits. The sGFP-TatM013 plasmid was therefore packaged in an AAV-based vector containing four tyrosine-to-phenylalanine (Y→F) and one threonine-to-valine (T→V) mutation on its capsid surface: AAV2(quadY→F+T→V). Y→F mutations were at amino acid positions 272, 444, 500, and 730 and the T→V mutation was at amino acid position 491 of the AAV2 capsid protein. This pentuple-mutant variant was capable of infecting multiple cell types in the retina after injection into the vitreous compartment (Kay et al., 2013). AAV vector was injected into the vitreous fluid of right eyes ($3 \times 10^9$ vector genomes delivered) of C57B/6J mice. As a control, the left eyes were injected with the same capsid mutant driving only GFP. This vector was chosen to control for the impact of ocular injection on the release of neurotrophic factors such as basic fibroblast growth factor (bFGF) and ciliary neurotrophic factor (CNTF) as reported in the literature (Wen et al., 1995; Qin and Rodrigues, 2010). Two weeks after injection all mice were inspected by spectral domain optical coherence tomography (SD-OCT) to rule out retinal detachments and inflammatory infiltrates in the vitreous. Importantly, neither the GFP-expressing virus nor the sGFP-TatM013-expressing virus led to ocular inflammation. Mice were evaluated by fluorescence funduscopy 4 weeks after vector injection. Fluorescence imaging revealed that the AAV2(quadY-F+T-V)-smCBA-mediated GFP expression was robust and panretinal, with the most intense labeling surrounding retinal blood vessels. In contrast, AAV2 (quadY-F+T-V)-mediated sGFP-TatM013 exhibited a diffuse pattern of fluorescence, suggesting secretion of the fused protein. This diffuse fluorescence, however, was not observed in noninjected control animals, indicating that the signal was caused by the expression of sGFP (FIG. 4A-1, FIG. 4A-2, FIG. 4A-3, and FIG. 4A-4).

Figures 2, 3B:
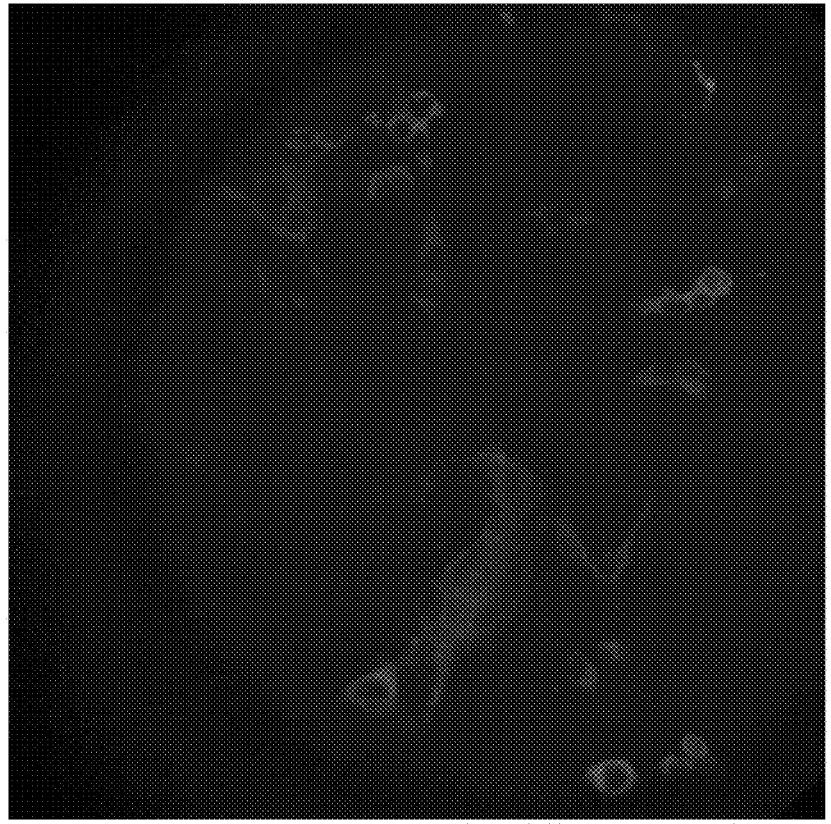
Figures 2, 4A:
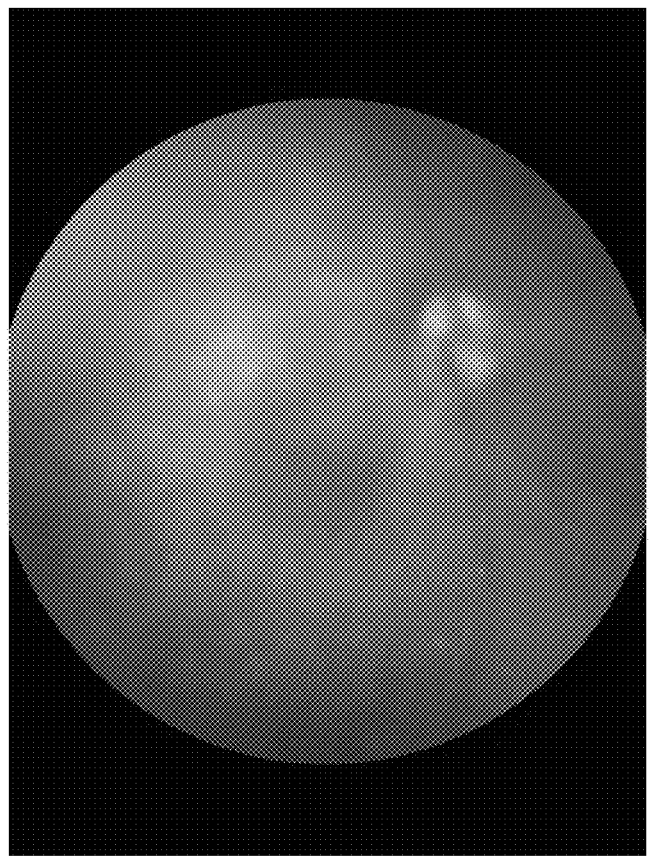
Figures 1, 4A:
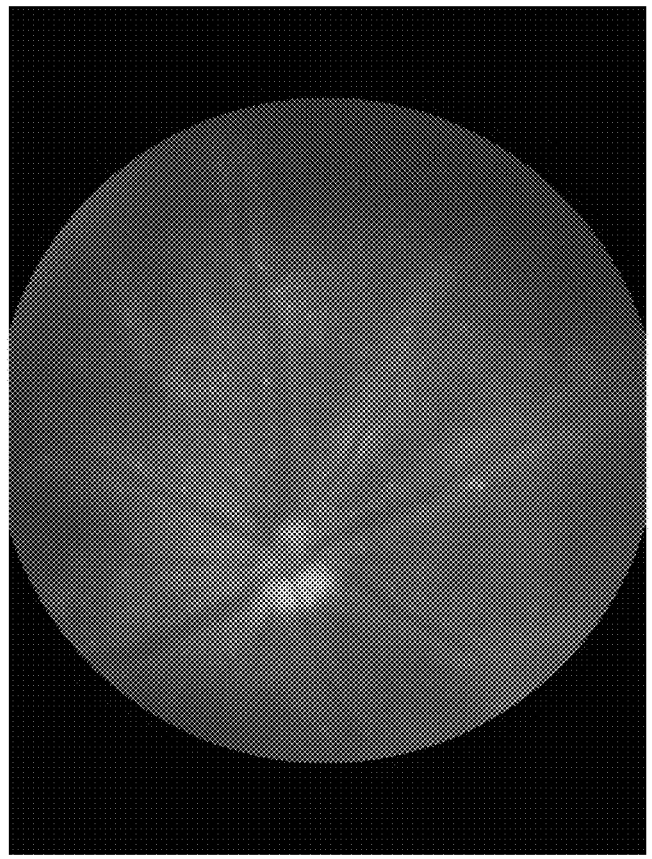
Figures 4, 4A:
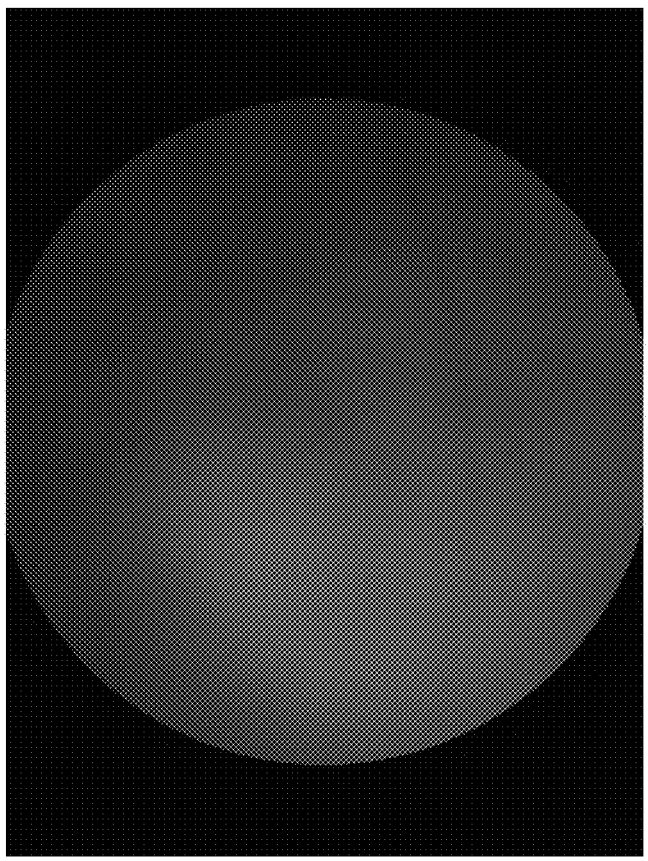
Figures 3, 4A:
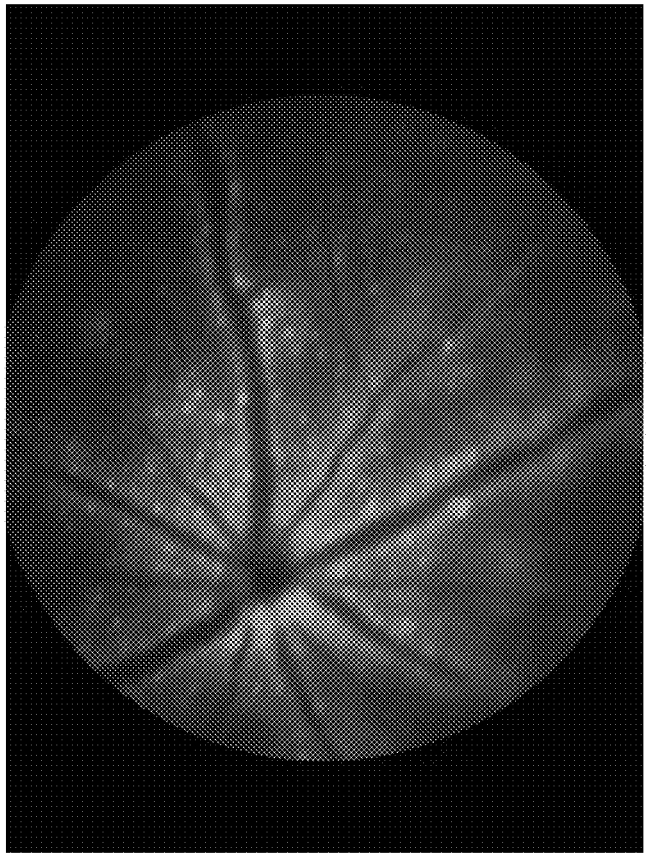
Figures 2, 4B:
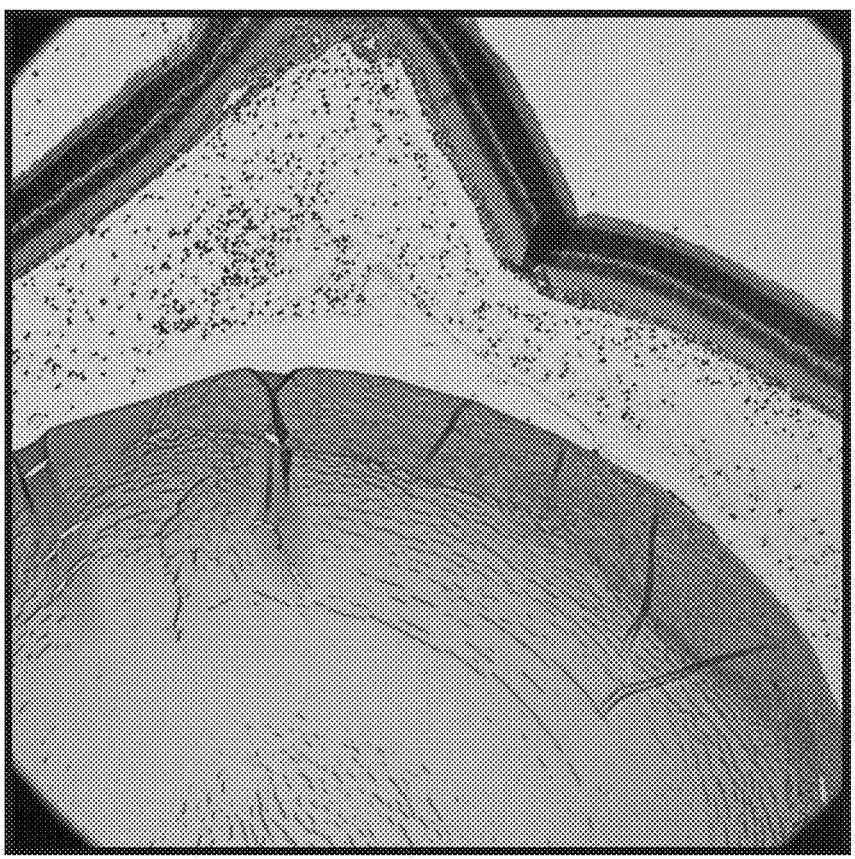
Figures 1, 4B:
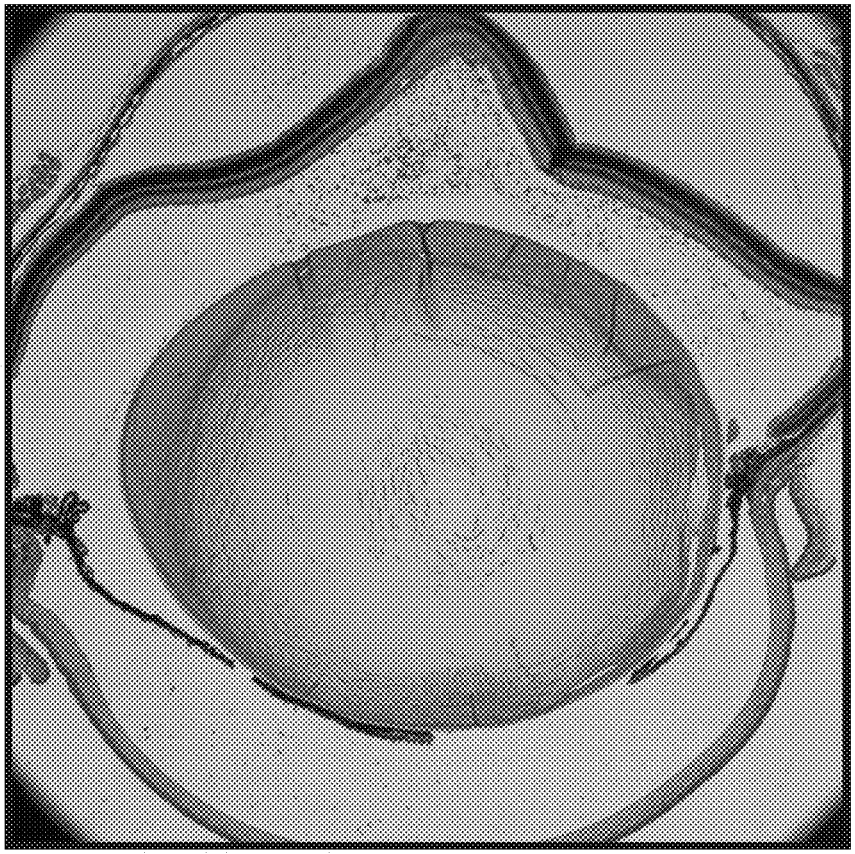
Figures 4, 4B:
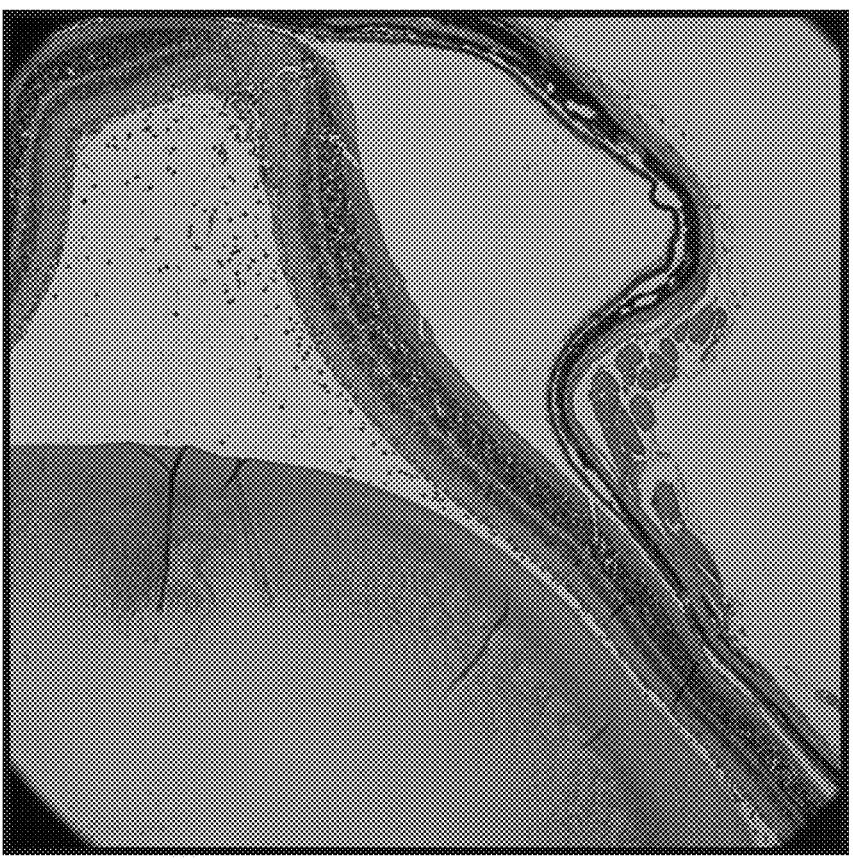
Figures 3, 4B:

To test the biological activity of this AAV vector in a model of acute ocular inflammation, the well-characterized endotoxin-induced uveitis (EIU) mouse model was used (Rosenbaum et al., 1980). Increases in IL-1β and other cytokines have been reported in this model (Shen et al., 2000), making it a suitable in vivo system for testing the efficacy of the viral vectors of the present disclosure. The biological activity of AAV-mediated sGFP-TatM013 was next evaluated by inducing an inflammatory response in the treated eyes by an injection of LPS 5 weeks after AAV injection. Levels of IL-1β in the vitreous body were quantified by subjecting the harvested vitreous to an ELISA. The concentration of IL-1β was significantly lower in the samples from eyes treated with sGFP-TatM013 than in the GFP-treated control eyes (FIG. 4A-1). To quantify the effect of this vector on the recruitment of infiltrating cells, the minimal dose of LPS (25 ng) was used that would induce uveitis, allowing these cells to be counted by light microscopy. To quantify the amount of infiltrating leukocytes in response to LPS challenge, eyes were harvested 24 hr after LPS injection, when inflammatory cell infiltration response peaks in the C57BL/6J strain (Shen et al., 2000), and fixed and embedded in paraffin for sectioning and staining with hematoxylin and eosin (FIG. 4A-2). The average number of immune cells infiltrating the vitreous chamber in AAV-sGFP-TatM013-treated eyes was reduced by nearly 50% relative to eyes treated with control AAV-GFP (FIG. 4A-3). These results indicate that expression of the fusion gene sGFP-TatM013 significantly reduced the infiltrating inflammatory cell response in this widely used model of ocular inflammation. Furthermore, these results indicated that the TatM013 fusion gene had anti-inflammatory activities that could be measured both in cultured cells and in the eyes of test animals.

Inflammation contributes to the pathology of chronic diseases affecting many organ systems and tissues, including the CNS. In the brain, activation of glial cells is thought to play a role in the etiology of Alzheimer disease36 and amyotrophic lateral sclerosis (ALS) (Hall et al., 1998; Chiu et al., 2009). In the retina, chronic inflammation has been implicated in age-related macular degeneration (AMD), but the sources of that inflammation are a matter of conjecture and include such disparate molecules as oxidized lipids, 39 bis-retinoids (Anderson et al., 2013), double-stranded RNA (Tarallo et al., 2012), and amyloid peptides (Cao et al., 2013; Liu et al., 2013). To suppress inflammation that may arise from more than one stimulus affecting a variety of cell types within complex tissues such as the eye, a generalized anti-inflammatory strategy perfected by poxviruses was exploited. The myxoma virus M013 gene is expressed as a small (~19 kDa) cytoplasmic PYD-containing protein that interacts with two important regulatory components of innate immunity: NF-κB/p105 and the ASC of the inflammasomes. Expression of M013 protein thus blocks two important innate immune signaling cascades and reduces the secretion of inflammatory cytokines under their control: for example, IL-1β and IL-18 under inflammasome control and TNF and IL-6 under NF-κB control (Johnston et al., 2005; Rahman, and McFadden, 2011; Rahman et al., 2009). In infections of susceptible hosts (rabbits of the genus *Oryctolagus*), suppression of the immune response by myxoma is so successful that a single infectious virion is sufficient to kill an adult rabbit (Shope, 1932). Viruses deleted for the M013 gene, however, are severely attenuated because of the inability of the mutant virus to inhibit innate immune and inflammatory responses of the host (Johnston et al., 2005; Rahman, and McFadden, 2011). Some of the immunomodulators expressed by this virus act only within this rabbit species, but others, such as M013, inhibit host cell targets in a wide variety of species (Liu et al., 2010; Lucas and McFadden, 2004). Thus, the M013 protein inhibits both NF-κB and inflammasome signaling in human and murine cells, as well as in rabbits (Rahman, and McFadden, 2011).

Although the retinal pigment epithelium (RPE) plays a major role in the secretion of inflammatory cytokines in diseases such as uveitis and AMD, other important sources of proinflammatory molecules include Müller glia, the major resident macroglial cells of the retina, retinal microglia, and vascular endothelial cells. Because there are multiple sources of induced inflammatory pathways, an AAV2-based capsid mutant was constructed that expresses a secretable and cell-penetrating fused version of M013. The N-terminal signal sequence from immunoglobulin κ led to efficient section of a sGFP-TatM013 fusion protein, with the GFP cleaved from TatM013 by furin during the secretion phase. The cell penetration signal derived from HIV tat permitted entry of the TatM013 fusion protein into intact non-transduced cells in the surrounding tissue. Cell culture experiments indicated that this fused TatM013 gene retained the immune suppressive properties of the parental M013 protein. The sGFP-TatM013 fusion protein inhibited the secretion of ligand-induced IL-1β in relevant cell types, the mouse monocyte line RAW 246.7, human myeloid THP-1 cells, and the RPE-like human ARPE-19 line, even after incubation in media from various cells that had secreted M013. When injected in mouse vitreous this capsid mutant of AAV co-expressed recombinant M013 protein and GFP with a pattern of fluorescence consistent with a secreted protein. Furthermore, transduction with this AAV vector also led to a significant decrease in the recruitment of inflammatory cells in the vitreous, when eyes were challenged with LPS 1 month after vector delivery in the EIU mouse model.

The eye presents a particularly useful tissue to test immunomodulatory therapy against chronic inflammatory syndromes, using AAV gene therapy vectors armed with this secreted tat-fusion version of M013. Inflammation in the eye is localized and, because the TatM013 protein is secreted from cells that take up and express the AAV-TatM013 vector, a low dose of vector delivered to the vitreous compartment should protect all layers of the retina from inflammatory signals that arise locally. Indeed, monoclonal antibodies that bind vascular endothelial growth factor (VEGF)-A are delivered directly to the vitreous in order to block neovascularization from the choroid, on the other side of the neural retina (Abedi et al., 2014). Tseng and colleagues demonstrated that activation of the inflammasome could be associated with the low-grade inflammation associated with dry AMD (Tseng et al., 2013). Activation of the NLRP3 inflammasome has also been reported in donor samples and in mouse models of AMD (Tarallo et al., 2012; Kerur et al., 2013). In addition to uveitis, the inventors contemplate that many other diseases of the eye may also be amenable to therapy using one or more of the AAV-TatM013-based vectors and expression systems disclosed herein. For example, a mouse model of geographic atrophy has been developed, based on oxidative stress in the RPE (Seo et al., 2012). A secreted, cell-penetrating M013 peptide, delivered to suitable neighboring cells may be able to protect photoreceptor structure and function in the face of increased oxidative stress.

The expression of the TatM013 fusion protein significantly inhibited the lipopolysaccharide (LPS) induced secretion of IL-1β from THP-1 cells. Stable ARPE-19 cells transduced with either empty lentivirus vector control or TatM013 lentivirus vector were stimulated with 4-HNE at 30 μM for 24 hrs. The levels of secreted IL-1β in the conditioned media were lower in cells expressing the TatM013 construct than in the empty lentivirus, vector control cells. The cellular distribution of sGFP-TatM013 in transfected cells was punctate in contrast to the diffuse cytoplasmic distribution of GFP alone. The fused sGFP-TatM013 construct was detected in transfected cell lysates, whereas the cleaved GFP was detected in the corresponding cell conditioned media. Incubation of either ARPE-19 or Raw 264.7 cells with this conditioned medium significantly decreased both the LPS and the 4-HNE induced secretion of IL-1β. The in vivo effects were determined by intravitreally injecting the sGFP-TatM013 or GFP control vector in C57Bl/6 mice and by inducing intraocular inflammation one month later through an injection of LPS. The sGFP- TatM013 injected eyes had a significantly lower number of infiltrating inflammatory cells when compared to control GFP injected eyes.

The expression of TatM013 inhibited LPS- and 4-HNE-induced secretion of IL-1β. The viral constructs described herein offer a secretable form of the TatM013 protein that is useful in blocking retinal and RPE inflammation, as demonstrated by its effect in the EIU mouse model.

These data provide the first evidence of a virus-derived inhibitor of innate immunity expressed from a gene-therapy vector that demonstrates usefulness for protecting neighboring, non-transduced cells against inflammatory insults, such as those emanating from a specific target tissue.

Example 2

Use of Vector Constructs for n Non-Ocular Indications

In addition to the use of the constructs in treatment of ocular disorders, the disclosed rAAV-tatM013 vectors may also be used to prevent, reduce, treat, and/or ameliorate one or more symptoms of inflammation in mammalian tissues other than those of the eye.

Such conditions include, for example, but not limited to, inflammation of one or more tissues or organs in the mammalian body such as the intestines, the liver, the pancreas, as well as one or more delocalized or diffuse sites within the body (including, for example, the peritoneal cavity) that are amenable to gene transduction by one or more of the disclosed AAV-based genetic constructs.

Example 3

Systemic Administration of Vector Constructs in Immunosuppressive Therapy Modalities Systemic treatment with rAAV-vectored TatM013 therapeutic constructs, such as those described herein may be facilitated by regulating production of the fusion protein with one or more exogenous inducers.

Even without specific regulation of the TatM013 gene, localized AAV-mediated expression of the secreted M013 may also be of significant value for treating one or more chronic autoimmune disorders or other organ-specific inflammatory diseases.

Example 4

Exemplary Secretion Signals for Retinal Expression*

In the practice of the present disclosure, the inventors contemplate the use of vectors comprising a nucleic acid segment that encodes one or more of a number of secretion signals for the preparation of therapeutic expression systems. In addition to the exemplary secretion signal utilized in the previous examples, one or more of the following secretion signal sequences may be employed in particular aspects of the invention wherein expression in the retina is desirable. Such secretion signals include, without limitation:

TABLE 1

SECRETION SIGNAL SEQUENCES FOR RETINAL EXPRESSION

| PROTEIN | UNIPROT NO. | SIGNAL SEQUENCE | SEQ ID NO: XX |
|---------|-------------|-----------------|---------------|
| CNTF | P26992 | MAAPVPWACCAVLAAAAAVVYA | 1 |
| PEDF | P36955 | MQALVLLLCIGALLGHSSC | 2 |
| FGF10 | O15520 | MWKWILTHCASAFPHLPGCCCC CFLLLFLVSSVPVTC | 3 |
| PDGF-A | P04085 | MRTLACLLLLGCGYLAHVLA | 4 |
| Gas6 | Q14393 | MAPSLSPGPAALRRAPQLLLLL LAAECALA | 5 |
| TIMP3 | P35625 | MTPWLGLIVLLGSWSLGDWGAE A | 6 |
| VEGF-A | P15692 | MNFLLSWVHWSLALLLYLHHAK WSQA | 7 |
| TGF-b 1 | P01137 | MPPSGLRLLLLLLPLLWLLVLT PGRPAAG | 8 |
| CFH | P08603 | MRLLAKIICLMLWAICVA | 9 |
| IL-8 | P10145 | MTSKLAVALLAAFLISAALC | 10 |
| MCP-1 | P13500 | MKVSAALLCLLLIAATFIPQGL A | 11 |
| GDNF | P39905 | MKLWDVVAVCLVLLHTASA | 12 |

Example 5

Exemplary Cell Penetrating Peptides

In the practice of the present disclosure, the inventors contemplate the use of vectors comprising a nucleic acid segment that encodes one or more of a number of cell penetrating peptides (CPP) for the preparation of particular therapeutic expression systems. In addition to the use of M013 peptides as shown in the previous examples, one or more of the following amino acid sequences may also find particular usefulness in certain aspects of the invention.

In those embodiments, a vector may be prepared in which the nucleotide sequence of the M013 peptide shown above is replaced with a nucleic acid sequence that encodes one or more of the CPP amino acid sequences including, without limitation:

TABLE 2

EXEMPLARY CELL PENETRATING PEPTIDES

| Peptide Amino Acid Sequence | SEQ ID NO: XX | Origin |
|------------------------------|---------------|--------|
| From Heparan Binding Proteins: | | |
| RKKRRRESRKKRRRES | 13 | DPV3 |
| GRPRESGKKRKRKRLKP | 14 | DPV6 |
| GKRKKKGKLGKKRDP | 15 | DPV7 |
| GKRKKKGKLGKKRPRSR | 16 | DPV7b |
| RKKRRRESRRARRSPRHL | 17 | DPV3/10 |

TABLE 2-continued

EXEMPLARY CELL PENETRATING PEPTIDES

| Peptide Amino Acid Sequence | SEQ ID NO: XX | Origin |
| --- | --- | --- |
| SRRARRSPRESGKKRKRKR | 18 | DPV10/6 |
| VKRGLKLRHVRPRVTRMDV | 19 | DPV1047 |
| SRRARRSPRHLGSG | 20 | DPV10 |
| LRRERQSRLRRERQSR | 21 | DPV15 |
| GAYDLRRRERQSRLRRRERQSR | 22 | DPV15b |
| From RNA Binding Proteins: | | |
| RKKRRQRRR | 23 | HIV-1 Tat |
| RRRRNRTRRNRRRVR | 24 | FHV coat |
| TRQARRNRRRRWRERQR | 25 | HIV-1 Rev |
| TRRQRTRRARRNR | 26 | HTLV-II Rex |
| KMTRAQRRAAARRNRWTAR | 27 | BMV Gag |
| NAKTRRHERRRKLAIER | 28 | P22N |
| MDAQTRRRERRAEKQAQWKAAN | 29 | λN(1-22) |
| TAKTRYKARRAELIAERR | 30 | φ21N(12-29) |
| TRRNKRNRIQEQLNRK | 31 | Yeast PrP6 |
| From DNA Binding Proteins: | | |
| PRRRRSSSRPVRRRRRPRVSRRRRRRGGRRRR | 32 | Protamine 1 |
| RIKAERKRMRNRIAASKSRKRKLERIAR | 33 | Human cJun |
| KRRIRRERNKMAAAKSRNRRRELTDT | 34 | Human cFos |
| KRARNTEAARRSRARKLQRMKQ | 35 | Yeast GCN4 |
| RQIKIWFQNRRMKWKK | 36 | Penetratin |
| RVIRVWFQNKRCKDKK | 37 | Islet-1 |
| SKRTRQTYTRYQTLELEKEFHFNRYITRRRRIDIANALSLSERQIKIWFQNRRMKSKKDR | 38 | Fushi-tarazu |
| SQIKIWFQNKRAKIKK | 39 | Engrailed-2 |
| RQVTIWFQNRRVKEKK | 40 | HoxA-13 |
| KQINNWFINQRKRHWK | 41 | Knotted-1 |
| RHIKIWFQNRRMKWKK | 42 | PDX-1 |
| From Signal Peptides: | | |
| MGLGLHLLVLAAALQGAKKKRKV | 43 | Ig(v) |
| MVKSKIGSWILVLFVAMWSDVGLCKKRPKP | 44 | BPrPp(1-30) |
| MANLGYWLLALFVTMWTDVGLCKKRPKP | 45 | MPrPp(1-28) |
| AAVLLPVLLAAPVQRKRQKLP | 46 | K-FGF + NLS |
| AAVLLPVLLAAP | 47 | K-FGF + NLS |

TABLE 2-continued

EXEMPLARY CELL PENETRATING PEPTIDES

| Peptide Amino Acid Sequence | SEQ ID NO: XX | Origin |
| --- | --- | --- |
| From Antimicrobial Peptides: | | |
| RRIRPRPPRLPRPRPRPLPFPRPG | 48 | Bac7 |
| VDKGSYLPRPTPPRPIYNRN | 49 | Pyrrhocoricin |
| KCFQWQRNMRKVRGPPVSCIKR | 50 | Lactoferrin 19-40 |
| TRSSRAGLQWPVGRVHRLLRK | 51 | Buforin 2 |
| GIGAVLKVLTTGLPALISWIKRKRQQ | 52 | Melittin |
| GIGKWLHSAKKFGKAFVGEIMNS | 53 | Magainin 2 |
| LLGDFFRKSKEKIGKEFKRIVQRIKDFLRNLVPRTESC | 54 | LL-37 |
| RGGRLSYSRRRFSTSTGR | 55 | SynB1 |
| YKQCHKKGGKKGSG | 56 | Crotamine |
| ALWKTLLKKVLKAPKKKRKV | 57 | S4(13)-PV(rev) |
| HARIKPTFRRLKWKYKGKFW | 58 | L-2 |
| From Viral Proteins: | | |
| TKRRITPKDVIDVRSVTTEINT | 59 | E(rns) |
| RQGAARVTSWLGRQLRIAGKRLEGRSK | 60 | VP22 |
| NAATATRGRSAASRPTQRPRAPARSASRPRRPVQ | 61 | HIV-1 VPR 77-92 |
| RHSRIGIIQQRRTRNG | 62 | Ribotoxin2 L3loop |
| KLIKGRTPIKFGKADCDRPPKHSQNGMGK | 63 | PreS2-TLM |
| PLSSIFSRIGDP | 64 | VT5 |
| DPKGDPKGVTVTVTVTGKGDPKPD | 65 | |
| From Natural Proteins: | | |
| RRIPNRRPRR | 66 | HRSV |
| RLRWR | 67 | AIP6 |
| MVRRFLVTLRIRRACGPPRVRV | 68 | ARF (1-22) |
| MVTVLFRRLRIRRACGPPRVRV | 69 | M918 |
| LLIILRRRIRKQAHAHSK | 70 | pVEC |
| LSTAADMQGVVTDGMASG | 71 | Azurin p18 |
| LSTAADMQGVVTDGMASGLDKDYLKPDD | 72 | Azurin p28 |
| KFHTFPQTAIGVGAP | 73 | hCT18-32 |
| VPTLK (PMLKE, VPALR, VSALK, IPALK) | 74 | Bip |
| PFVYLI | 75 | C105Y |
| PIEVCMYREP | 76 | FGF12 |

TABLE 2-continued

EXEMPLARY CELL PENETRATING PEPTIDES

| Peptide Amino Acid Sequence | SEQ ID NO: XX | Origin |
|---|---|---|
| From Peptide Libraries: | | |
| R8, R9, R10, R12 Polyarginine | | |
| KETWWETWWTEWSQPKKRKV | 77 | Pep-1 |
| GLAFLGFLGAAGSTMGAWSQPKKKRKV | 78 | MPG |
| GWTLNSAGYLLGKINLKALAALAKKIL | 79 | Transportan |
| AGYLLGHINLHHLAHLAibHHIL | 80 | TH |
| KLALKALKALKAALKLA | 81 | MAP |
| RRWWRRWRR | 82 | W/R |
| GLWRALWRLLRSLWRLLWRA | 83 | CADY |
| LIRLWSHLIHIWFQNRRLKWKKK | 84 | EB-1 |
| WEAALAEALAEALAEHLAEALAEALEALAA | 85 | GALA |
| LKTLTETLKELTKTLTEL | 86 | MAP12 |
| QLALQLALQALQAALQLA | 87 | MAP17 |
| (PPR) 3, (PPR) 4, (PPR) 5, (PPR) 6 | | (PPR)n |
| (PRR) 3, (PRR) 4, (PRR) 5, (PRR) 6 | | (PRR)n |
| GPSQPTYPGDDAPVRDLIRFYRDLQRYLNVVTRHRY | 88 | aPP4R1 |
| GPSQPTYPGDDAPVRDLIRFYRDLRRYLNVVTRHRY | 89 | aPP5R1 |
| GPSQPTYPGDDAPVRDLRRFYRDLRRYLNVVTRHRY | 90 | aPP6R1 |
| G(PLXX)NP1 | | PoliProline-based |
| VRLPPPVRLPPPVRLPPP | 91 | SAP |
| VELPPPVELPPPVELPPP | 92 | SAP(E) |
| FKIYDKKVRTRVVKH | 93 | SVM1 |
| RASKRDGSWVKKLHRILE | 94 | SVM2 |
| KGTYKKKLMRIPLKGT | 95 | SVM3 |
| LYKKGPAKKGRPPLRGWFH | 96 | SVM4 |
| HSPIIPLGTRFVCHGVT | 97 | SVM5 |
| YTAIAWVKAFIRKLRK | 98 | YTA2 |
| IAWVKAFIRKLRKGPLG | 99 | YTA4 |
| RLSGMNEVLSFRWL | 100 | SG3 |
| SDLWEMMMVSLACQY | 101 | Pep-7 |
| VTWTPQAWFQWV | 102 | |
| GSPWGLQHHPPRT | 103 | 439a |
| GPFHFYQFLFPPV | 104 | 435b |
| TSPLNIHNGQKL | 105 | HN-1 |
| CAYHRLRRC | 106 | |
| RCGRASRCRVRWMRRRRI | 107 | BEN_1079 |
| PYSRPHVQLWYPNRESCRSLIRSLGP | 108 | BEN_0805 |
| PLILLRLLRGQF | 109 | Pept1 |
| PLIYLRLLRGQF | 110 | Pept2 |
| KLWMRWYSPTTRRYG | 111 | IW-14 |

(Adapted from a review by Francesca Milleti, doi:10.1016/j.drudis.2012.03.002; 2012).

REFERENCES

The following references, to the extent that they provide exemplary procedural or other details supplementary to those set forth herein, are specifically incorporated herein in their entirety by express reference thereto:

ABEDI, F et al., "Anti-VEGF treatment in neovascular age-related macular degeneration: a treat-and-extend protocol over 2 years," Retina, 34:1531-1538 (2014).

AMBATI, J et al., "Age-related macular degeneration: etiology, pathogenesis, and therapeutic strategies." Surv. Ophthalmol., 48:257-93 (2003).

ANDERSON, O A et al., "A2E induces IL-1β production in retinal pigment epithelial cells via the NLRP3 inflammasome," PLoS One, 8:e67263 (2013).

ARSENAULT, B J et al., "Regression of atherosclerosis," Curr. Cardiol. Rep., 14:443-449 (2012).

BELTRAN, W A et al., "rAAV2/5 gene-targeting to rods: dose-dependent efficiency and complications associated with different promoters," Gene Ther., 17:1162-1174 (2010).

BRATKE, K A et al., "A survey of host range genes in poxvirus genomes," Infect. Genet. Evol., 14:406-425 (2013).

CAO, L et al., "Aβ-induced senescent retinal pigment epithelial cells create a proinflammatory microenvironment in AMD," Invest. Ophthalmol Vis. Sci., 54:3738-3750 (2013).

CHIU, I M et al., "Activation of innate and humoral immunity in the peripheral nervous system of ALS transgenic mice," Proc. Nat'l. Acad. Sci. USA, 106:20960-20965 (2009).

CORDERO-COMA, M et al., "Serum cytokine profile in adalimumab-treated refractory uveitis patients: decreased IL-22 correlates with clinical responses," Ocul. Immunol. Inflamm., 21:212-219 (2013).

FOSTER, C S and VITALE, A T, eds. Diagnosis and Treatment of Uveitis (W.B. Saunders, Philadelphia, Pa.). pp. 17-23 (2002).

HALL, E D et al., "Relationship of microglial and astrocytic activation to disease onset and progression in a transgenic model of familial ALS," Glia, 23:249-256 (1998).

HAUSWIRTH, W W et al., "Treatment of Leber congenital amaurosis due to RPE65 mutations by ocular subretinal injection of adeno-associated virus gene vector: short-term results of a phase I trial," *Hum. Gene Ther.*, 19:979-990 (2008).

HOLLYFIELD, J G et al., "A hapten generated from an oxidation fragment of docosahexaenoic acid is sufficient to initiate age-related macular degeneration," *Mol. Neurobiol.*, 41:290-298 (2010).

HORI, J "Mechanisms of immune privilege in the anterior segment of the eye: what we learn from corneal transplantation," *J. Ocul. Biol. Dis. Infor.*, 1:94-100 (2008).

JACOBSON, S G et al., "Safety of recombinant adeno-associated virus type 2-RPE65 vector delivered by ocular subretinal injection," *Mol. Ther.*, 13:1074-1084 (2006).

JOHNSTON, J B et al., "A poxvirus-encoded pyrin domain protein interacts with ASC-1 to inhibit host inflammatory and apoptotic responses to infection," *Immunity*, 25(4): 687-698 (October 2006).

KAKIHANA, T et al., "Dynamic regulation of Ero1α and peroxiredoxin 4 localization in the secretory pathway," *J. Biol. Chem.*, 288(41):29586-29594 (October 2013).

KAUPPINEN, A et al., "Oxidative stress activates NLRP3 inflammasomes in ARPE-19 cells—implications for age-related macular degeneration (AMD)," *Immunol. Lett.*, 147(1-2):29-33 (September 2012).

KAY, C N et al., "Targeting photoreceptors via intravitreal delivery using novel, capsid-mutated AAV vectors," *PLoS One*, 8(4):e62097 (April 2013).

KERR, P J, "Myxomatosis in Australia and Europe: a model for emerging infectious diseases," *Antiviral Res.*, 93(3): 387-415 (February 2012).

KERUR, N et al., "TLR-independent and P2X7-dependent signaling mediate Alu RNA-induced NLRP3 inflammasome activation in geographic atrophy," *Invest. Ophthalmol. Vis. Sci.*, 54:7395-7401 (2013).

KOHNO, H, et al., "Photoreceptor proteins initiate microglial activation via Toll-like receptor 4 in retinal degeneration mediated by all-trans-retinal," *J. Biol. Chem.*, 288:15326-15341 (2013).

LAEMMLI, U K, "Cleavage of structural proteins during the assembly of the head of bacteriophage T4," *Nature*, 227:680-685 (1970).

LIU, J et al., "The immunoregulatory properties of oncolytic myxoma virus and their implications in therapeutics," *Microbes Infect.*, 12(14-15):1144-1152 (September 2010).

LIU, L, and CHAN, C, "The role of inflammasome in Alzheimer's disease," *Ageing Res. Rev.*, 15:6-15 (May 2014).

LIU, R T et al., "Inflammatory mediators induced by amyloid-β in the retina and RPE in vivo: implications for inflammasome activation in age-related macular degeneration," *Invest. Ophthalmol. Vis. Sci.*, 54:2225-2237 (2013).

LUCAS, A and MCFADDEN, G., "Secreted immunomodulatory viral proteins as novel biotherapeutics," *J. Immunol.*, 173(8):4765-4774 (October 2004).

MACLAREN, R E et al., "Retinal gene therapy in patients with choroideremia: initial findings from a phase 1/2 clinical trial," *Lancet*, 383:1129-1137 (2014).

MAGUIRE, A M et al., "Safety and efficacy of gene transfer for Leber's congenital amaurosis," *N. Engl. J. Med.*, 358:2240-2248 (2008).

MOCHIZUKI, M et al., "Immunological homeostasis of the eye," *Prog. Retin. Eye Res.*, 33:10-27 (2013).

QIN, S and RODRIGUES, G A, "Differential roles of AMPKα1 and AMPKα2 in regulating 4-HNE-induced RPE cell death and permeability," *Exp. Eye Res.*, 91:818-824 (2010).

RAHMAN, M M and MCFADDEN, G, "Myxoma virus lacking the pyrin-like protein M013 is sensed in human myeloid cells by both NLRP3 and multiple Toll-like receptors, which independently activate the inflammasome and NF-κB innate response pathways," *J. Virol.*, 85:12505-12517 (2011).

RAHMAN, M M et al., "Co-regulation of NF-κB and inflammasome-mediated inflammatory responses by myxoma virus pyrin domain-containing protein M013," *PLoS Pathog.*, 5:e1000635 (2009).

RAHMAN, M M et al., "Myxoma virus protein MO29 is a dual-function immunomodulator that inhibits PKR and also conscripts RHA/DHX9 to promote expanded host tropism and viral replication," *PLoS Pathog.*, 9:e1003465 (2013).

REINHARDT, T A et al., "The $Ca^{2+}/H^+$ antiporter TMEM165 expression, localization in the developing, lactating and involuting mammary gland parallels the secretory pathway $Ca^{2+}$ ATPase (SPCA1)," *Biochem. Biophys. Res. Commun.*, 445(2):417-421 (March 2014).

ROSENBAUM, J T and KIM, H W, "Innate immune signals in autoimmune and autoinflammatory uveitis," *Int. Rev. Immunol.*, 32(1):68-75 (February 2013).

ROSENBAUM, J T et al., "Endotoxin-induced uveitis in rats as a model for human disease," *Nature*, 286:611-613 (August 1980).

SEO, S et al., "Pathological consequences of long-term mitochondrial oxidative stress in the mouse retinal pigment epithelium," *Exp. Eye Res.*, 101:60-71 (June 2012).

SHEN, D F et al., "Cytokine gene expression in different strains of mice with endotoxin-induced uveitis (EIU)," *Ocul. Immunol. Inflamm.*, 8(4):221-225 (December 2000).

SHOPE, R E, "A filtrable virus causing a tumor-like condition in rabbits and its relationship to virus myxomatosum," *J. Exp. Med.*, 56(6):803-822 (November 1932),"

SIMONELLI, F et al., "Gene therapy for Leber's congenital amaurosis is safe and effective through 1.5 years after vector administration," *Mol. Ther.*, 18(3):643-650 (December 2010).

SKEIE, J M et al., "Evisceration of mouse vitreous and retina for proteomic analyses," *J. Vis. Exp.*, 50:2795 (April 2011).

SMITH, G L et al., "Vaccinia virus immune evasion: mechanisms, virulence and immunogenicity," *J. Gen. Virol.*, 94:2367-2392 (September 2013).

STOW, J L and MURRAY, R Z, "Intracellular trafficking and secretion of inflammatory cytokines," *Cytokine Growth Factor Rev.*, 24(3):227-239 (June 2013).

TARALLO, V et al., "DICER1 loss and Alu RNA induce age-related macular degeneration via the NLRP3 inflammasome and MyD88," *Cell*, 149(4):847-859 (April 2012).

TESTA, F et al., "Three-year follow-up after unilateral subretinal delivery of adeno-associated virus in patients with Leber congenital amaurosis type 2," *Ophthalmology*, 120(6):1283-1291 (March 2013).

TSENG, W A et al., "NLRP3 inflammasome activation in retinal pigment epithelial cells by lysosomal destabilization: implications for age-related macular degeneration," *Invest. Ophthalmol. Vis. Sci.*, 54(1):110-120 (January 2013).

VALENTINCIC, N V et al., "Intraocular and serum cytokine profiles in patients with intermediate uveitis," *Mol. Vis.,* 17:2003-2010 (July 2011).

VERMA, A et al., "ACE2 and Ang-(1-7) confer protection against development of diabetic retinopathy," *Mol. Ther. J. Am. Soc. Gene Ther.,* 20(1):28-36 (January 2012).

WEN, R et al., "Injury-induced upregulation of bFGF and CNTF mRNAS in the rat retina," *J. Neurosci.,* 15(11):7377-7385 (November 1995).

ZARBIN, M A, "Current concepts in the pathogenesis of age-related macular degeneration," *Arch. Ophthalmol.,* 122(4):598-614 (April 2004).

ZOLOTUKHIN, S et al., "Production and purification of serotype 1, 2, and 5 recombinant adeno-associated viral vectors," *Methods,* 28(2):158-167 (October 2002).

It should be understood that the examples and embodiments described herein are for illustrative purposes only and that various modifications or changes in light thereof will be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising," "having," "including," or "containing," with reference to an element or elements is intended to provide support for a similar aspect or embodiment of the invention that "consists of," "consists essentially of," or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope, and concept of the invention as defined by the appended claims.

---

What is claimed is:

1. A method of reducing or inhibiting secretion of proinflammatory cytokines from retinal microglia during conditions of inflammation, comprising contacting a population of retinal cells in one or both eyes of a mammalian subject with a composition that comprises an effective amount of a viral particle comprising an AAV vector comprising a polynucleotide that comprises
   (a) a first nucleic acid segment that encodes a virally-derived M013 polypeptide; and
   (b) a second nucleic acid segment encoding a polypeptide comprising a cell penetrating peptide comprising the sequence set forth in SEQ ID NO: 23 and a secretion signal peptide;
   wherein the first and second nucleic acid segments are operably linked to a promoter sequence that expresses the encoded polypeptides in one or more retinal cells transduced with the viral particle;
   wherein the viral particle has a serotype that is AAV2 or AA2-based, and the viral particle comprises an AAV2 (quadY-F+T-V) capsid protein; wherein the composition is contacted to the one or both eyes by intravitreal injection; wherein the population comprises one or more retinal microglia; and wherein the contacting provides a reduction or inhibition in secretion of proinflammatory cytokines from the retinal microglia.

2. A method for treating or ameliorating one or more symptoms of inflammation in a mammal, the method comprising administering to the mammal a composition that comprises a viral particle comprising an AAV vector comprising a polynucleotide that comprises
   (a) a first nucleic acid segment that encodes a virally-derived M013 polypeptide; and
   (b) a second nucleic acid segment encoding a polypeptide comprising a cell penetrating peptide comprising the sequence set forth in SEQ ID NO: 23 and a secretion signal peptide;
   wherein the first and second nucleic acid segments are operably linked to a promoter sequence that expresses the encoded polypeptides in one or more retinal cells transduced with the viral particle; in an amount and for a time sufficient to treat or ameliorate the one or more symptoms of inflammation in the mammal, wherein the AAV vector is administered to one or both eyes of the mammal by intravitreal injection;

wherein the viral particle has a serotype that is AAV2 or AA2-based, and the viral particle comprises an AAV2 (quadY-F+T-V) capsid protein;
wherein the one or both eyes comprises one or more retinal microglia; and wherein the administering provides a reduction or inhibition in secretion of proinflammatory cytokines from the retinal microglia.

3. The method of claim 2, wherein the mammal is a human that has been diagnosed with macular degeneration, age-related macular degeneration (AMD), geographic atrophy, wet AMD, dry AMD, drusen formation, dry eye, diabetic retinopathy, vitreoretinopathy, Best macular dystrophy, Sorsby fundus dystrophy, Mallatia Leventinese and Doyne honeycomb retinal dystrophy, corneal inflammation, uveitis, ocular hypertension, glaucoma, or any combination thereof.

4. The method of claim 2, wherein expression of the encoded polypeptides in the retinal cells: a) treats or ameliorates one or more symptoms of inflammation, b) preserves one or more photoreceptor cells, or c) a combination thereof.

5. The method of claim 2, wherein expression of the encoded polypeptides persists in the retinal cells for a period of at least three months following intravitreal injection of the AAV vector to the one or both eyes of the mammal.

6. The method of claim 2, wherein the intravitreal injection occurs as a single injection, or wherein the intravitreal injection includes sequential injection of the AAV vector to the one or both eyes over a pre-determined treatment period of several weeks to several months.

7. The method of claim 2, wherein expression of the encoded polypeptides persists in the retinal cells for a period of at least six months following intravitreal injection of the AAV vector to the one or both eyes of the mammal.

8. The method of claim 2, wherein the cell penetrating peptide undergoes proteolytic cleavage from the encoded polypeptide expressed by the remainder of the second nucleic acid segment.

9. The method of claim 3, wherein the vector is intravitreally injected in an amount and for a time sufficient to treat or ameliorate symptoms of dry AMD.

10. The method of claim 1, wherein the AAV vector is a self-complementary rAAV (scAAV) vector.

11. The method of claim 2, wherein the AAV vector is a self-complementary rAAV (scAAV) vector.

12. The method of claim 1, wherein the polynucleotide further comprises an enhancer, a post-transcriptional regulatory sequence, a polyadenylation signal, an inverted terminal repeat, a multiple cloning site, or any combination thereof, operably linked to the first and the second nucleic acid segments.

13. The method of claim 2, wherein the polynucleotide further comprises an enhancer, a post-transcriptional regulatory sequence, a polyadenylation signal, an inverted terminal repeat, a multiple cloning site, or any combination thereof, operably linked to the first and the second nucleic acid segments.

14. The method of claim 1, wherein the promoter is an endogenous promoter, an exogenous promoter, a viral-derived promoter, a mammalian-specific promoter, a tissue-specific promoter, a cell-specific promoter, a constitutive promoter, an inducible promoter, a human cell-specific promoter, or any combination thereof.

15. The method of claim 2, wherein the promoter is an endogenous promoter, an exogenous promoter, a viral-derived promoter, a mammalian-specific promoter, a tissue-specific promoter, a cell-specific promoter, a constitutive promoter, an inducible promoter, a human cell-specific promoter, or any combination thereof.

16. The method of claim 1, wherein the polynucleotide further comprises a sequence region that expresses or encodes a first therapeutic molecule, a first diagnostic molecule, or a combination thereof.

17. The method of claim 16, wherein the first therapeutic molecule or the first diagnostic molecule is selected from the group consisting of a polypeptide, a peptide, a ribozyme, a peptide nucleic acid, an siRNA, an RNAi, an antisense oligonucleotide, an antisense polynucleotide, an antibody, an antigen binding fragment, and any combination thereof.

18. The method of claim 2, wherein the polynucleotide further comprises a sequence region that expresses or encodes a first therapeutic molecule, a first diagnostic molecule, or a combination thereof.

19. The method of claim 18, wherein the first therapeutic molecule or the first diagnostic molecule is selected from the group consisting of a polypeptide, a peptide, a ribozyme, a peptide nucleic acid, an siRNA, an RNAi, an antisense oligonucleotide, an antisense polynucleotide, an antibody, an antigen binding fragment, and any combination thereof.

20. The method of claim 1, wherein the secretion signal peptide is selected from the group consisting of an N-terminal mammalian secretion signal peptide selected from the group consisting of an IgK peptide, a glucagon-like peptide, a PEDF peptide, a FGF10 peptide, a PDGF-A peptide, a Gas6 peptide, a CFH peptide, a GDNF peptide, an IL-8 peptide, an MCP-1 peptide, a TIMP3 peptide, a synthetic peptide, a peptide signal sequence as set forth in any one of SEQ ID NOs: 1 to 12, and any combination thereof.

21. The method of claim 2, wherein the secretion signal peptide is selected from the group consisting of an N-terminal mammalian secretion signal peptide selected from the group consisting of an IgK peptide, a glucagon-like peptide, a PEDF peptide, a FGF10 peptide, a PDGF-A peptide, a Gas6 peptide, a CFH peptide, a GDNF peptide, an IL-8 peptide, an MCP-1 peptide, a TIMP3 peptide, a synthetic peptide, a peptide signal sequence as set forth in any one of SEQ ID NOs: 1 to 12, and any combination thereof.

22. The method of claim 1, wherein the proinflammatory cytokines comprise IL-1β.

23. The method of claim 2, wherein the proinflammatory cytokines comprise IL-1β.

24. The method of claim 1, wherein the subject is suspected of having, has been diagnosed with, or is at risk for developing, a disease or abnormal condition that is associated with, or caused by, oxidative stress or inflammation in one or more retinal cells of the subject.

25. The method of claim 24, wherein the disease or abnormal condition is selected from the group consisting of age-related macular degeneration (AMD), wet AMD, dry AMD, geographic atrophy, drusen formation, dry eye, diabetic retinopathy, vitreoretinopathy, corneal inflammation, Best macular dystrophy, Sorsby fundus dystrophy, Mallatia Leventinese and Doyne honeycomb retinal dystrophy, uveitis, ocular hypertension, glaucoma, and combinations thereof.

26. The method of claim 2, wherein the mammal is a human that has been diagnosed with diabetic retinopathy.

27. The method of claim 1, wherein the subject is suspected of having, has been diagnosed with, or is at risk for developing diabetic retinopathy.

* * * * *

UNITED STATES PATENT AND TRADEMARK OFFICE
CERTIFICATE OF CORRECTION

PATENT NO. : 11,685,767 B2
APPLICATION NO. : 15/261599
DATED : June 27, 2023
INVENTOR(S) : Douglas Grant McFadden et al.

It is certified that error appears in the above-identified patent and that said Letters Patent is hereby corrected as shown below:

In the Claims

Claim 1, at Column 83, Line 65:
"AA2-based,"
Should read:
-- AAV2-based, --

Claim 2, at Column 85, Line 2:
"AA2-based,"
Should read:
-- AAV2-based, --

Signed and Sealed this
Twenty-third Day of April, 2024

Katherine Kelly Vidal
*Director of the United States Patent and Trademark Office*

SEQUENCE LISTING

```
<160> NUMBER OF SEQ ID NOS: 111

<210> SEQ ID NO 1
<211> LENGTH: 22
<212> TYPE: PRT
<213> ORGANISM: Artificial Sequence
<220> FEATURE:
<223> OTHER INFORMATION: CNTF Synthetic Peptide Signal Sequence

<400> SEQUENCE: 1

Met Ala Ala Pro Val Pro Trp Ala Cys Cys Ala Val Leu Ala Ala Ala
1               5                   10                  15

Ala Ala Val Val Tyr Ala
            20

<210> SEQ ID NO 2
<211> LENGTH: 19
<212> TYPE: PRT
<213> ORGANISM: Artificial Sequence
<220> FEATURE:
<223> OTHER INFORMATION: PEDF Synthetic Peptide Signal Sequence

<400> SEQUENCE: 2

Met Gln Ala Leu Val Leu Leu Leu Cys Ile Gly Ala Leu Leu Gly His
1               5                   10                  15

Ser Ser Cys

<210> SEQ ID NO 3
<211> LENGTH: 37
<212> TYPE: PRT
<213> ORGANISM: Artificial Sequence
<220> FEATURE:
<223> OTHER INFORMATION: FGF10 Synthetic Peptide Signal Sequence
```

```
<400> SEQUENCE: 3

Met Trp Lys Trp Ile Leu Thr His Cys Ala Ser Ala Phe Pro His Leu
1               5                   10                  15

Pro Gly Cys Cys Cys Cys Cys Phe Leu Leu Leu Phe Leu Val Ser Ser
                20                  25                  30

Val Pro Val Thr Cys
                35

<210> SEQ ID NO 4
<211> LENGTH: 20
<212> TYPE: PRT
<213> ORGANISM: Artificial Sequence
<220> FEATURE:
<223> OTHER INFORMATION: PDGF-A Synthetic Peptide Signal Sequence

<400> SEQUENCE: 4

Met Arg Thr Leu Ala Cys Leu Leu Leu Leu Gly Cys Gly Tyr Leu Ala
1               5                   10                  15

His Val Leu Ala
                20

<210> SEQ ID NO 5
<211> LENGTH: 30
<212> TYPE: PRT
<213> ORGANISM: Artificial Sequence
<220> FEATURE:
<223> OTHER INFORMATION: GAS6 Synthetic Peptide Signal Sequence

<400> SEQUENCE: 5

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala
                20                  25                  30

<210> SEQ ID NO 6
<211> LENGTH: 23
<212> TYPE: PRT
<213> ORGANISM: Artificial Sequence
<220> FEATURE:
<223> OTHER INFORMATION: TIMP3 Synthetic Peptide Signal Sequence

<400> SEQUENCE: 6

Met Thr Pro Trp Leu Gly Leu Ile Val Leu Leu Gly Ser Trp Ser Leu
1               5                   10                  15

Gly Asp Trp Gly Ala Glu Ala
                20

<210> SEQ ID NO 7
<211> LENGTH: 26
<212> TYPE: PRT
<213> ORGANISM: Artificial Sequence
<220> FEATURE:
<223> OTHER INFORMATION: VEGF-A Synthetic Peptide Signal Sequence

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala
                20                  25

<210> SEQ ID NO 8
<211> LENGTH: 29
<212> TYPE: PRT
```

-continued

```
<213> ORGANISM: Artificial Sequence
<220> FEATURE:
<223> OTHER INFORMATION: TGFB1 Synthetic Peptide Signal Sequence

<400> SEQUENCE: 8

Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly
            20                  25

<210> SEQ ID NO 9
<211> LENGTH: 18
<212> TYPE: PRT
<213> ORGANISM: Artificial Sequence
<220> FEATURE:
<223> OTHER INFORMATION: CFH Synthetic Peptide Signal Sequence

<400> SEQUENCE: 9

Met Arg Leu Leu Ala Lys Ile Ile Cys Leu Met Leu Trp Ala Ile Cys
1               5                   10                  15

Val Ala

<210> SEQ ID NO 10
<211> LENGTH: 20
<212> TYPE: PRT
<213> ORGANISM: Artificial Sequence
<220> FEATURE:
<223> OTHER INFORMATION: IL-8 Synthetic Peptide Signal Sequence

<400> SEQUENCE: 10

Met Thr Ser Lys Leu Ala Val Ala Leu Leu Ala Ala Phe Leu Ile Ser
1               5                   10                  15

Ala Ala Leu Cys
            20

<210> SEQ ID NO 11
<211> LENGTH: 23
<212> TYPE: PRT
<213> ORGANISM: Artificial Sequence
<220> FEATURE:
<223> OTHER INFORMATION: MCP-1 Synthetic Peptide Signal Sequence

<400> SEQUENCE: 11

Met Lys Val Ser Ala Ala Leu Leu Cys Leu Leu Leu Ile Ala Ala Thr
1               5                   10                  15

Phe Ile Pro Gln Gly Leu Ala
            20

<210> SEQ ID NO 12
<211> LENGTH: 19
<212> TYPE: PRT
<213> ORGANISM: Artificial Sequence
<220> FEATURE:
<223> OTHER INFORMATION: GDNF Synthetic Peptide Signal Sequence

<400> SEQUENCE: 12

Met Lys Leu Trp Asp Val Val Ala Val Cys Leu Val Leu Leu His Thr
1               5                   10                  15

Ala Ser Ala

<210> SEQ ID NO 13
<211> LENGTH: 16
<212> TYPE: PRT
<213> ORGANISM: Artificial Sequence
```

```
<220> FEATURE:
<223> OTHER INFORMATION: Heparan Binding Protein Cell Penetrating
      Peptide

<400> SEQUENCE: 13

Arg Lys Lys Arg Arg Arg Glu Ser Arg Lys Lys Arg Arg Arg Glu Ser
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 14

Gly Arg Pro Arg Glu Ser Gly Lys Lys Arg Lys Arg Lys Arg Leu Lys
1               5                   10                  15

Pro

<210> SEQ ID NO 15
<211> LENGTH: 15
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 15

Gly Lys Arg Lys Lys Lys Gly Lys Leu Gly Lys Lys Arg Asp Pro
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 16

Gly Lys Arg Lys Lys Lys Gly Lys Leu Gly Lys Lys Arg Pro Arg Ser
1               5                   10                  15

Arg

<210> SEQ ID NO 17
<211> LENGTH: 18
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 17

Arg Lys Lys Arg Arg Arg Glu Ser Arg Arg Ala Arg Arg Ser Pro Arg
1               5                   10                  15

His Leu

<210> SEQ ID NO 18
<211> LENGTH: 19
<212> TYPE: PRT
<213> ORGANISM: Artificial Sequence
<220> FEATURE:
<223> OTHER INFORMATION: Heparan Binding Protein Cell Penetrating
      Peptide
```

<400> SEQUENCE: 18

Ser Arg Arg Ala Arg Arg Ser Pro Arg Glu Ser Gly Lys Lys Arg Lys
1               5                   10                  15

Arg Lys Arg

<210> SEQ ID NO 19
<211> LENGTH: 19
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 19

Val Lys Arg Gly Leu Lys Leu Arg His Val Arg Pro Arg Val Thr Arg
1               5                   10                  15

Met Asp Val

<210> SEQ ID NO 20
<211> LENGTH: 14
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 20

Ser Arg Arg Ala Arg Arg Ser Pro Arg His Leu Gly Ser Gly
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 21

Leu Arg Arg Glu Arg Gln Ser Arg Leu Arg Arg Glu Arg Gln Ser Arg
1               5                   10                  15

<210> SEQ ID NO 22
<211> LENGTH: 22
<212> TYPE: PRT
<213> ORGANISM: Artificial Sequence
<220> FEATURE:
<223> OTHER INFORMATION: Heparan Binding Protein Cell Penetrating
      Peptide

<400> SEQUENCE: 22

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 23
<211> LENGTH: 9
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 23

Arg Lys Lys Arg Arg Gln Arg Arg Arg
1               5

<210> SEQ ID NO 24
<211> LENGTH: 15
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 24

Arg Arg Arg Arg Asn Arg Thr Arg Arg Asn Arg Arg Arg Val Arg
1               5                   10                  15

<210> SEQ ID NO 25
<211> LENGTH: 17
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 25

Thr Arg Gln Ala Arg Arg Asn Arg Arg Arg Arg Trp Arg Glu Arg Gln
1               5                   10                  15

Arg

<210> SEQ ID NO 26
<211> LENGTH: 13
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 26

Thr Arg Arg Gln Arg Thr Arg Arg Ala Arg Arg Asn Arg
1               5                   10

<210> SEQ ID NO 27
<211> LENGTH: 19
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 27

Lys Met Thr Arg Ala Gln Arg Arg Ala Ala Ala Arg Arg Asn Arg Trp
1               5                   10                  15

Thr Ala Arg

<210> SEQ ID NO 28
<211> LENGTH: 17
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 28

Asn Ala Lys Thr Arg Arg His Glu Arg Arg Arg Lys Leu Ala Ile Glu
1               5                   10                  15

Arg

<210> SEQ ID NO 29
<211> LENGTH: 22
<212> TYPE: PRT
<213> ORGANISM: Artificial Sequence

```
<220> FEATURE:
<223> OTHER INFORMATION: RNA Binding Protein Cell Penetrating Peptide

<400> SEQUENCE: 29

Met Asp Ala Gln Thr Arg Arg Glu Arg Arg Ala Glu Lys Gln Ala
1               5                   10                  15

Gln Trp Lys Ala Ala Asn
            20

<210> SEQ ID NO 30
<211> LENGTH: 18
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 30

Thr Ala Lys Thr Arg Tyr Lys Ala Arg Arg Ala Glu Leu Ile Ala Glu
1               5                   10                  15

Arg Arg

<210> SEQ ID NO 31
<211> LENGTH: 16
<212> TYPE: PRT
<213> ORGANISM: Artificial Sequence
<220> FEATURE:
<223> OTHER INFORMATION: RNA Binding Protein Cell Penetrating Peptide

<400> SEQUENCE: 31

Thr Arg Arg Asn Lys Arg Asn Arg Ile Gln Glu Gln Leu Asn Arg Lys
1               5                   10                  15

<210> SEQ ID NO 32
<211> LENGTH: 32
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 32

Pro Arg Arg Arg Arg Ser Ser Ser Arg Pro Val Arg Arg Arg Arg Arg
1               5                   10                  15

Pro Arg Val Ser Arg Arg Arg Arg Arg Gly Gly Arg Arg Arg Arg
            20                  25                  30

<210> SEQ ID NO 33
<211> LENGTH: 28
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 33

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 34
<211> LENGTH: 26
<212> TYPE: PRT
<213> ORGANISM: Artificial Sequence
<220> FEATURE:
<223> OTHER INFORMATION: DNA Binding Protein Cell Penetrating Peptide
```

```
<400> SEQUENCE: 34

Lys Arg Arg Ile Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 35
<211> LENGTH: 22
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 35

Lys Arg Ala Arg Asn Thr Glu Ala Ala Arg Ser Arg Ala Arg Lys
1               5                   10                  15

Leu Gln Arg Met Lys Gln
            20

<210> SEQ ID NO 36
<211> LENGTH: 16
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 36

Arg Gln Ile Lys Ile Trp Phe Gln Asn Arg Arg Met Lys Trp Lys Lys
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 37

Arg Val Ile Arg Val Trp Phe Gln Asn Lys Arg Cys Lys Asp Lys Lys
1               5                   10                  15

<210> SEQ ID NO 38
<211> LENGTH: 60
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 38

Ser Lys Arg Thr Arg Gln Thr Tyr Thr Arg Tyr Gln Thr Leu Glu Leu
1               5                   10                  15

Glu Lys Glu Phe His Phe Asn Arg Tyr Ile Thr Arg Arg Arg Ile
            20                  25                  30

Asp Ile Ala Asn Ala Leu Ser Leu Ser Glu Arg Gln Ile Lys Ile Trp
        35                  40                  45

Phe Gln Asn Arg Arg Met Lys Ser Lys Lys Asp Arg
    50                  55                  60

<210> SEQ ID NO 39
<211> LENGTH: 16
<212> TYPE: PRT
<213> ORGANISM: Artificial Sequence
<220> FEATURE:
<223> OTHER INFORMATION: DNA Binding Protein Cell Penetrating Peptide
```

-continued

```
<400> SEQUENCE: 39

Ser Gln Ile Lys Ile Trp Phe Gln Asn Lys Arg Ala Lys Ile Lys Lys
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 40

Arg Gln Val Thr Ile Trp Phe Gln Asn Arg Arg Val Lys Glu Lys Lys
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 41

Lys Gln Ile Asn Asn Trp Phe Ile Asn Gln Arg Lys Arg His Trp Lys
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: DNA Binding Protein Cell Penetrating Peptide

<400> SEQUENCE: 42

Arg His Ile Lys Ile Trp Phe Gln Asn Arg Arg Met Lys Trp Lys Lys
1               5                   10                  15

<210> SEQ ID NO 43
<211> LENGTH: 23
<212> TYPE: PRT
<213> ORGANISM: Artificial Sequence
<220> FEATURE:
<223> OTHER INFORMATION: Signal Peptide-Derived Cell Penetrating Peptide

<400> SEQUENCE: 43

Met Gly Leu Gly Leu His Leu Leu Val Leu Ala Ala Ala Leu Gln Gly
1               5                   10                  15

Ala Lys Lys Lys Arg Lys Val
            20

<210> SEQ ID NO 44
<211> LENGTH: 30
<212> TYPE: PRT
<213> ORGANISM: Artificial Sequence
<220> FEATURE:
<223> OTHER INFORMATION: Signal Peptide-Derived Cell Penetrating Peptide

<400> SEQUENCE: 44

Met Val Lys Ser Lys Ile Gly Ser Trp Ile Leu Val Leu Phe Val Ala
1               5                   10                  15

Met Trp Ser Asp Val Gly Leu Cys Lys Lys Arg Pro Lys Pro
            20                  25                  30

<210> SEQ ID NO 45
```

```
<211> LENGTH: 28
<212> TYPE: PRT
<213> ORGANISM: Artificial Sequence
<220> FEATURE:
<223> OTHER INFORMATION: Signal Peptide-Derived Cell Penetrating Peptide

<400> SEQUENCE: 45

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 46
<211> LENGTH: 21
<212> TYPE: PRT
<213> ORGANISM: Artificial Sequence
<220> FEATURE:
<223> OTHER INFORMATION: Signal Peptide-Derived Cell Penetrating Peptide

<400> SEQUENCE: 46

Ala Ala Val Leu Leu Pro Val Leu Leu Ala Ala Pro Val Gln Arg Lys
1               5                   10                  15

Arg Gln Lys Leu Pro
            20

<210> SEQ ID NO 47
<211> LENGTH: 12
<212> TYPE: PRT
<213> ORGANISM: Artificial Sequence
<220> FEATURE:
<223> OTHER INFORMATION: Signal Peptide-Derived Cell Penetrating Peptide

<400> SEQUENCE: 47

Ala Ala Val Leu Leu Pro Val Leu Leu Ala Ala Pro
1               5                   10

<210> SEQ ID NO 48
<211> LENGTH: 24
<212> TYPE: PRT
<213> ORGANISM: Artificial Sequence
<220> FEATURE:
<223> OTHER INFORMATION: Antimicrobial Cell Penetrating Peptide

<400> SEQUENCE: 48

Arg Arg Ile Arg Pro Arg Pro Pro Arg Leu Pro Arg Pro Arg Pro Arg
1               5                   10                  15

Pro Leu Pro Phe Pro Arg Pro Gly
            20

<210> SEQ ID NO 49
<211> LENGTH: 20
<212> TYPE: PRT
<213> ORGANISM: Artificial Sequence
<220> FEATURE:
<223> OTHER INFORMATION: Antimicrobial Cell Penetrating Peptide

<400> SEQUENCE: 49

Val Asp Lys Gly Ser Tyr Leu Pro Arg Pro Thr Pro Pro Arg Pro Ile
1               5                   10                  15

Tyr Asn Arg Asn
            20

<210> SEQ ID NO 50
<211> LENGTH: 22
<212> TYPE: PRT
```

```
<213> ORGANISM: Artificial Sequence
<220> FEATURE:
<223> OTHER INFORMATION: Antimicrobial Cell Penetrating Peptide

<400> SEQUENCE: 50

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 51
<211> LENGTH: 21
<212> TYPE: PRT
<213> ORGANISM: Artificial Sequence
<220> FEATURE:
<223> OTHER INFORMATION: Antimicrobial Cell Penetrating Peptide

<400> SEQUENCE: 51

Thr Arg Ser Ser Arg Ala Gly Leu Gln Trp Pro Val Gly Arg Val His
1               5                   10                  15

Arg Leu Leu Arg Lys
            20

<210> SEQ ID NO 52
<211> LENGTH: 26
<212> TYPE: PRT
<213> ORGANISM: Artificial Sequence
<220> FEATURE:
<223> OTHER INFORMATION: Antimicrobial Cell Penetrating Peptide

<400> SEQUENCE: 52

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 53
<211> LENGTH: 23
<212> TYPE: PRT
<213> ORGANISM: Artificial Sequence
<220> FEATURE:
<223> OTHER INFORMATION: Antimicrobial Cell Penetrating Peptide

<400> SEQUENCE: 53

Gly Ile Gly Lys Trp Leu His Ser Ala Lys Lys Phe Gly Lys Ala Phe
1               5                   10                  15

Val Gly Glu Ile Met Asn Ser
            20

<210> SEQ ID NO 54
<211> LENGTH: 38
<212> TYPE: PRT
<213> ORGANISM: Artificial Sequence
<220> FEATURE:
<223> OTHER INFORMATION: Antimicrobial Cell Penetrating Peptide

<400> SEQUENCE: 54

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Cys
        35
```

<210> SEQ ID NO 55
<211> LENGTH: 18
<212> TYPE: PRT
<213> ORGANISM: Artificial Sequence
<220> FEATURE:
<223> OTHER INFORMATION: Antimicrobial Cell Penetrating Peptide

<400> SEQUENCE: 55

Arg Gly Gly Arg Leu Ser Tyr Ser Arg Arg Phe Ser Thr Ser Thr
1               5                   10                  15

Gly Arg

<210> SEQ ID NO 56
<211> LENGTH: 14
<212> TYPE: PRT
<213> ORGANISM: Artificial Sequence
<220> FEATURE:
<223> OTHER INFORMATION: Antimicrobial Cell Penetrating Peptide

<400> SEQUENCE: 56

Tyr Lys Gln Cys His Lys Lys Gly Gly Lys Lys Gly Ser Gly
1               5                   10

<210> SEQ ID NO 57
<211> LENGTH: 20
<212> TYPE: PRT
<213> ORGANISM: Artificial Sequence
<220> FEATURE:
<223> OTHER INFORMATION: Antimicrobial Cell Penetrating Peptide

<400> SEQUENCE: 57

Ala Leu Trp Lys Thr Leu Leu Lys Lys Val Leu Lys Ala Pro Lys Lys
1               5                   10                  15

Lys Arg Lys Val
            20

<210> SEQ ID NO 58
<211> LENGTH: 20
<212> TYPE: PRT
<213> ORGANISM: Artificial Sequence
<220> FEATURE:
<223> OTHER INFORMATION: Antimicrobial Cell Penetrating Peptide

<400> SEQUENCE: 58

His Ala Arg Ile Lys Pro Thr Phe Arg Arg Leu Lys Trp Lys Tyr Lys
1               5                   10                  15

Gly Lys Phe Trp
            20

<210> SEQ ID NO 59
<211> LENGTH: 22
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 59

Thr Lys Arg Arg Ile Thr Pro Lys Asp Val Ile Asp Val Arg Ser Val
1               5                   10                  15

Thr Thr Glu Ile Asn Thr
            20

<210> SEQ ID NO 60
<211> LENGTH: 27

```
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 60

Arg Gln Gly Ala Ala Arg Val Thr Ser Trp Leu Gly Arg Gln Leu Arg
1               5                   10                  15

Ile Ala Gly Lys Arg Leu Glu Gly Arg Ser Lys
            20                  25

<210> SEQ ID NO 61
<211> LENGTH: 34
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 61

Asn Ala Ala Thr Ala Thr Arg Gly Arg Ser Ala Ala Ser Arg Pro Thr
1               5                   10                  15

Gln Arg Pro Arg Ala Pro Ala Arg Ser Ala Ser Arg Pro Arg Arg Pro
            20                  25                  30

Val Gln

<210> SEQ ID NO 62
<211> LENGTH: 16
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 62

Arg His Ser Arg Ile Gly Ile Ile Gln Gln Arg Arg Thr Arg Asn Gly
1               5                   10                  15

<210> SEQ ID NO 63
<211> LENGTH: 29
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 63

Lys Leu Ile Lys Gly Arg Thr Pro Ile Lys Phe Gly Lys Ala Asp Cys
1               5                   10                  15

Asp Arg Pro Pro Lys His Ser Gln Asn Gly Met Gly Lys
            20                  25

<210> SEQ ID NO 64
<211> LENGTH: 12
<212> TYPE: PRT
<213> ORGANISM: Artificial Sequence
<220> FEATURE:
<223> OTHER INFORMATION: Viral Protein-Derived Cell Penetrating Peptide

<400> SEQUENCE: 64

Pro Leu Ser Ser Ile Phe Ser Arg Ile Gly Asp Pro
1               5                   10

<210> SEQ ID NO 65
<211> LENGTH: 26
<212> TYPE: PRT
<213> ORGANISM: Artificial Sequence
<220> FEATURE:
```

-continued

<223> OTHER INFORMATION: Viral Protein-Derived Cell Penetrating Peptide

<400> SEQUENCE: 65

Asp Pro Lys Gly Asp Pro Lys Gly Val Thr Val Thr Val Thr Val Thr
1               5                   10                  15

Val Thr Gly Lys Gly Asp Pro Lys Pro Asp
            20                  25

<210> SEQ ID NO 66
<211> LENGTH: 10
<212> TYPE: PRT
<213> ORGANISM: Artificial Sequence
<220> FEATURE:
<223> OTHER INFORMATION: Cell Penetrating Peptide

<400> SEQUENCE: 66

Arg Arg Ile Pro Asn Arg Arg Pro Arg Arg
1               5                   10

<210> SEQ ID NO 67
<211> LENGTH: 5
<212> TYPE: PRT
<213> ORGANISM: Artificial Sequence
<220> FEATURE:
<223> OTHER INFORMATION: Cell Penetrating Peptide

<400> SEQUENCE: 67

Arg Leu Arg Trp Arg
1               5

<210> SEQ ID NO 68
<211> LENGTH: 22
<212> TYPE: PRT
<213> ORGANISM: Artificial Sequence
<220> FEATURE:
<223> OTHER INFORMATION: Cell Penetrating Peptide

<400> SEQUENCE: 68

Met Val Arg Arg Phe Leu Val Thr Leu Arg Ile Arg Arg Ala Cys Gly
1               5                   10                  15

Pro Pro Arg Val Arg Val
            20

<210> SEQ ID NO 69
<211> LENGTH: 22
<212> TYPE: PRT
<213> ORGANISM: Artificial Sequence
<220> FEATURE:
<223> OTHER INFORMATION: Cell Penetrating Peptide

<400> SEQUENCE: 69

Met Val Thr Val Leu Phe Arg Arg Leu Arg Ile Arg Arg Ala Cys Gly
1               5                   10                  15

Pro Pro Arg Val Arg Val
            20

<210> SEQ ID NO 70
<211> LENGTH: 18
<212> TYPE: PRT
<213> ORGANISM: Artificial Sequence
<220> FEATURE:
<223> OTHER INFORMATION: Cell Penetrating Peptide

<400> SEQUENCE: 70

Leu Leu Ile Ile Leu Arg Arg Arg Ile Arg Lys Gln Ala His Ala His

```
1               5                   10                  15

Ser Lys

<210> SEQ ID NO 71
<211> LENGTH: 18
<212> TYPE: PRT
<213> ORGANISM: Artificial Sequence
<220> FEATURE:
<223> OTHER INFORMATION: Cell Penetrating Peptide

<400> SEQUENCE: 71

Leu Ser Thr Ala Ala Asp Met Gln Gly Val Val Thr Asp Gly Met Ala
1               5                   10                  15

Ser Gly

<210> SEQ ID NO 72
<211> LENGTH: 28
<212> TYPE: PRT
<213> ORGANISM: Artificial Sequence
<220> FEATURE:
<223> OTHER INFORMATION: Cell Penetrating Peptide

<400> SEQUENCE: 72

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 73
<211> LENGTH: 15
<212> TYPE: PRT
<213> ORGANISM: Artificial Sequence
<220> FEATURE:
<223> OTHER INFORMATION: Cell Penetrating Peptide

<400> SEQUENCE: 73

Lys Phe His Thr Phe Pro Gln Thr Ala Ile Gly Val Gly Ala Pro
1               5                   10                  15

<210> SEQ ID NO 74
<211> LENGTH: 5
<212> TYPE: PRT
<213> ORGANISM: Artificial Sequence
<220> FEATURE:
<223> OTHER INFORMATION: Cell Penetrating Peptide

<400> SEQUENCE: 74

Val Pro Thr Leu Lys
1               5

<210> SEQ ID NO 75
<211> LENGTH: 6
<212> TYPE: PRT
<213> ORGANISM: Artificial Sequence
<220> FEATURE:
<223> OTHER INFORMATION: Cell Penetrating Peptide

<400> SEQUENCE: 75

Pro Phe Val Tyr Leu Ile
1               5

<210> SEQ ID NO 76
<211> LENGTH: 10
<212> TYPE: PRT
<213> ORGANISM: Artificial Sequence
```

```
<220> FEATURE:
<223> OTHER INFORMATION: Cell Penetrating Peptide

<400> SEQUENCE: 76

Pro Ile Glu Val Cys Met Tyr Arg Glu Pro
1               5                   10

<210> SEQ ID NO 77
<211> LENGTH: 20
<212> TYPE: PRT
<213> ORGANISM: Artificial Sequence
<220> FEATURE:
<223> OTHER INFORMATION: Synthetic Cell Penetrating Peptide

<400> SEQUENCE: 77

Lys Glu Thr Trp Trp Glu Thr Trp Trp Thr Glu Trp Ser Gln Pro Lys
1               5                   10                  15

Lys Arg Lys Val
            20

<210> SEQ ID NO 78
<211> LENGTH: 27
<212> TYPE: PRT
<213> ORGANISM: Artificial Sequence
<220> FEATURE:
<223> OTHER INFORMATION: Synthetic Cell Penetrating Peptide

<400> SEQUENCE: 78

Gly Leu Ala Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 79
<211> LENGTH: 27
<212> TYPE: PRT
<213> ORGANISM: Artificial Sequence
<220> FEATURE:
<223> OTHER INFORMATION: Synthetic Cell Penetrating Peptide

<400> SEQUENCE: 79

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 80
<211> LENGTH: 23
<212> TYPE: PRT
<213> ORGANISM: Artificial Sequence
<220> FEATURE:
<223> OTHER INFORMATION: Synthetic Cell Penetrating Peptide

<400> SEQUENCE: 80

Ala Gly Tyr Leu Leu Gly His Ile Asn Leu His His Leu Ala His Leu
1               5                   10                  15

Ala Ile Asx His His Ile Leu
            20

<210> SEQ ID NO 81
<211> LENGTH: 17
<212> TYPE: PRT
<213> ORGANISM: Artificial Sequence
<220> FEATURE:
<223> OTHER INFORMATION: Synthetic Cell Penetrating Peptide
```

-continued

```
<400> SEQUENCE: 81

Lys Leu Ala Leu Lys Ala Leu Lys Ala Leu Lys Ala Ala Leu Lys Leu
1               5                   10                  15

Ala

<210> SEQ ID NO 82
<211> LENGTH: 9
<212> TYPE: PRT
<213> ORGANISM: Artificial Sequence
<220> FEATURE:
<223> OTHER INFORMATION: Synthetic Cell Penetrating Peptide

<400> SEQUENCE: 82

Arg Arg Trp Trp Arg Arg Trp Arg Arg
1               5

<210> SEQ ID NO 83
<211> LENGTH: 20
<212> TYPE: PRT
<213> ORGANISM: Artificial Sequence
<220> FEATURE:
<223> OTHER INFORMATION: Synthetic Cell Penetrating Peptide

<400> SEQUENCE: 83

Gly Leu Trp Arg Ala Leu Trp Arg Leu Leu Arg Ser Leu Trp Arg Leu
1               5                   10                  15

Leu Trp Arg Ala
            20

<210> SEQ ID NO 84
<211> LENGTH: 23
<212> TYPE: PRT
<213> ORGANISM: Artificial Sequence
<220> FEATURE:
<223> OTHER INFORMATION: Synthetic Cell Penetrating Peptide

<400> SEQUENCE: 84

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 85
<211> LENGTH: 30
<212> TYPE: PRT
<213> ORGANISM: Artificial Sequence
<220> FEATURE:
<223> OTHER INFORMATION: Synthetic Cell Penetrating Peptide

<400> SEQUENCE: 85

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 86
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 86
```

```
Leu Lys Thr Leu Thr Glu Thr Leu Lys Glu Leu Thr Lys Thr Leu Thr
1               5                   10                  15

Glu Leu

<210> SEQ ID NO 87
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 87

Gln Leu Ala Leu Gln Leu Ala Leu Gln Ala Leu Gln Ala Ala Leu Gln
1               5                   10                  15

Leu Ala

<210> SEQ ID NO 88
<211> LENGTH: 36
<212> TYPE: PRT
<213> ORGANISM: Artificial Sequence
<220> FEATURE:
<223> OTHER INFORMATION: Synthetic Cell Penetrating Peptide

<400> SEQUENCE: 88

Gly Pro Ser Gln Pro Thr Tyr Pro Gly Asp Asp Ala Pro Val Arg Asp
1               5                   10                  15

Leu Ile Arg Phe Tyr Arg Asp Leu Gln Arg Tyr Leu Asn Val Val Thr
                20                  25                  30

Arg His Arg Tyr
            35

<210> SEQ ID NO 89
<211> LENGTH: 36
<212> TYPE: PRT
<213> ORGANISM: Artificial Sequence
<220> FEATURE:
<223> OTHER INFORMATION: Synthetic Cell Penetrating Peptide

<400> SEQUENCE: 89

Gly Pro Ser Gln Pro Thr Tyr Pro Gly Asp Asp Ala Pro Val Arg Asp
1               5                   10                  15

Leu Ile Arg Phe Tyr Arg Asp Leu Arg Arg Tyr Leu Asn Val Val Thr
                20                  25                  30

Arg His Arg Tyr
            35

<210> SEQ ID NO 90
<211> LENGTH: 36
<212> TYPE: PRT
<213> ORGANISM: Artificial Sequence
<220> FEATURE:
<223> OTHER INFORMATION: Synthetic Cell Penetrating Peptide

<400> SEQUENCE: 90

Gly Pro Ser Gln Pro Thr Tyr Pro Gly Asp Asp Ala Pro Val Arg Asp
1               5                   10                  15

Leu Arg Arg Phe Tyr Arg Asp Leu Arg Arg Tyr Leu Asn Val Val Thr
                20                  25                  30

Arg His Arg Tyr
            35

<210> SEQ ID NO 91
```

```
<210> SEQ ID NO 91
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 91

Val Arg Leu Pro Pro Pro Val Arg Leu Pro Pro Pro Val Arg Leu Pro
1               5                   10                  15

Pro Pro

<210> SEQ ID NO 92
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 92

Val Glu Leu Pro Pro Pro Val Glu Leu Pro Pro Pro Val Glu Leu Pro
1               5                   10                  15

Pro Pro

<210> SEQ ID NO 93
<211> LENGTH: 15
<212> TYPE: PRT
<213> ORGANISM: Artificial Sequence
<220> FEATURE:
<223> OTHER INFORMATION: Synthetic Cell Penetrating Peptide

<400> SEQUENCE: 93

Phe Lys Ile Tyr Asp Lys Lys Val Arg Thr Arg Val Val Lys His
1               5                   10                  15

<210> SEQ ID NO 94
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 94

Arg Ala Ser Lys Arg Asp Gly Ser Trp Val Lys Lys Leu His Arg Ile
1               5                   10                  15

Leu Glu

<210> SEQ ID NO 95
<211> LENGTH: 16
<212> TYPE: PRT
<213> ORGANISM: Artificial Sequence
<220> FEATURE:
<223> OTHER INFORMATION: Synthetic Cell Penetrating Peptide

<400> SEQUENCE: 95

Lys Gly Thr Tyr Lys Lys Lys Leu Met Arg Ile Pro Leu Lys Gly Thr
1               5                   10                  15

<210> SEQ ID NO 96
<211> LENGTH: 19
<212> TYPE: PRT
<213> ORGANISM: Artificial Sequence
<220> FEATURE:
<223> OTHER INFORMATION: Synthetic Cell Penetrating Peptide

<400> SEQUENCE: 96
```

```
Leu Tyr Lys Lys Gly Pro Ala Lys Lys Gly Arg Pro Pro Leu Arg Gly
1               5                   10                  15

Trp Phe His

<210> SEQ ID NO 97
<211> LENGTH: 17
<212> TYPE: PRT
<213> ORGANISM: Artificial Sequence
<220> FEATURE:
<223> OTHER INFORMATION: Synthetic Cell Penetrating Peptide

<400> SEQUENCE: 97

His Ser Pro Ile Ile Pro Leu Gly Thr Arg Phe Val Cys His Gly Val
1               5                   10                  15

Thr

<210> SEQ ID NO 98
<211> LENGTH: 16
<212> TYPE: PRT
<213> ORGANISM: Artificial Sequence
<220> FEATURE:
<223> OTHER INFORMATION: Synthetic Cell Penetrating Peptide

<400> SEQUENCE: 98

Tyr Thr Ala Ile Ala Trp Val Lys Ala Phe Ile Arg Lys Leu Arg Lys
1               5                   10                  15

<210> SEQ ID NO 99
<211> LENGTH: 17
<212> TYPE: PRT
<213> ORGANISM: Artificial Sequence
<220> FEATURE:
<223> OTHER INFORMATION: Synthetic Cell Penetrating Peptide

<400> SEQUENCE: 99

Ile Ala Trp Val Lys Ala Phe Ile Arg Lys Leu Arg Lys Gly Pro Leu
1               5                   10                  15

Gly

<210> SEQ ID NO 100
<211> LENGTH: 14
<212> TYPE: PRT
<213> ORGANISM: Artificial Sequence
<220> FEATURE:
<223> OTHER INFORMATION: Synthetic Cell Penetrating Peptide

<400> SEQUENCE: 100

Arg Leu Ser Gly Met Asn Glu Val Leu Ser Phe Arg Trp Leu
1               5                   10

<210> SEQ ID NO 101
<211> LENGTH: 15
<212> TYPE: PRT
<213> ORGANISM: Artificial Sequence
<220> FEATURE:
<223> OTHER INFORMATION: Synthetic Cell Penetrating Peptide

<400> SEQUENCE: 101

Ser Asp Leu Trp Glu Met Met Met Val Ser Leu Ala Cys Gln Tyr
1               5                   10                  15

<210> SEQ ID NO 102
<211> LENGTH: 12
<212> TYPE: PRT
<213> ORGANISM: Artificial Sequence
```

<220> FEATURE:
<223> OTHER INFORMATION: Synthetic Cell Penetrating Peptide

<400> SEQUENCE: 102

Val Thr Trp Thr Pro Gln Ala Trp Phe Gln Trp Val
1               5                   10

<210> SEQ ID NO 103
<211> LENGTH: 13
<212> TYPE: PRT
<213> ORGANISM: Artificial Sequence
<220> FEATURE:
<223> OTHER INFORMATION: Synthetic Cell Penetrating Peptide

<400> SEQUENCE: 103

Gly Ser Pro Trp Gly Leu Gln His His Pro Pro Arg Thr
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic Cell Penetrating Peptide

<400> SEQUENCE: 104

Gly Pro Phe His Phe Tyr Gln Phe Leu Phe Pro Pro Val
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Synthetic Cell Penetrating Peptide

<400> SEQUENCE: 105

Thr Ser Pro Leu Asn Ile His Asn Gly Gln Lys Leu
1               5                   10

<210> SEQ ID NO 106
<211> LENGTH: 9
<212> TYPE: PRT
<213> ORGANISM: Artificial Sequence
<220> FEATURE:
<223> OTHER INFORMATION: Synthetic Cell Penetrating Peptide

<400> SEQUENCE: 106

Cys Ala Tyr His Arg Leu Arg Arg Cys
1               5

<210> SEQ ID NO 107
<211> LENGTH: 18
<212> TYPE: PRT
<213> ORGANISM: Artificial Sequence
<220> FEATURE:
<223> OTHER INFORMATION: Synthetic Cell Penetrating Peptide

<400> SEQUENCE: 107

Arg Cys Gly Arg Ala Ser Arg Cys Arg Val Arg Trp Met Arg Arg
1               5                   10                  15

Arg Ile

<210> SEQ ID NO 108
<211> LENGTH: 26
<212> TYPE: PRT

```
<213> ORGANISM: Artificial Sequence
<220> FEATURE:
<223> OTHER INFORMATION: Synthetic Cell Penetrating Peptide

<400> SEQUENCE: 108

Pro Tyr Ser Arg Pro His Val Gln Leu Trp Tyr Pro Asn Arg Glu Ser
1               5                   10                  15

Cys Arg Ser Leu Ile Arg Ser Leu Gly Pro
            20                  25

<210> SEQ ID NO 109
<211> LENGTH: 12
<212> TYPE: PRT
<213> ORGANISM: Artificial Sequence
<220> FEATURE:
<223> OTHER INFORMATION: Synthetic Cell Penetrating Peptide

<400> SEQUENCE: 109

Pro Leu Ile Leu Leu Arg Leu Leu Arg Gly Gln Phe
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Synthetic Cell Penetrating Peptide

<400> SEQUENCE: 110

Pro Leu Ile Tyr Leu Arg Leu Leu Arg Gly Gln Phe
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Synthetic Cell Penetrating Peptide

<400> SEQUENCE: 111

Lys Leu Trp Met Arg Trp Tyr Ser Pro Thr Thr Arg Arg Tyr Gly
1               5                   10                  15
```